(12) United States Patent
Hocek et al.

(10) Patent No.: US 9,586,986 B2
(45) Date of Patent: Mar. 7, 2017

(54) SUBSTITUTED 7-DEAZAPURINE RIBONUCLEOSIDES FOR THERAPEUTIC USES

(71) Applicants: Institute of Organic Chemistry and Biochemistry ASCR, v.v.i., Prague (CZ); Palacky University in Olomouc, Olomouc (CZ)

(72) Inventors: Michal Hocek, Prague (CZ); Petr Naus, Prague (CZ); Olga Caletkova, Bratislava (SK); Marian Hajduch, Moravsky Beroun (CZ); Petr Dzubak, Brodek u Prerova (CZ)

(73) Assignees: INSTITUTE OF ORGANIC CHEMISTRY AND BIOCHEMISTRY ASCR, V.V.I., Prague (CZ); PALACKY UNIVERSITY IN OLOMOUC, Olomouc (CZ)

( * ) Notice: Subject to any disclaimer, the term of this patent is extended or adjusted under 35 U.S.C. 154(b) by 0 days.

(21) Appl. No.: 14/562,090

(22) Filed: Dec. 5, 2014

(65) Prior Publication Data

US 2016/0159844 A1 Jun. 9, 2016

(51) Int. Cl.
*C07H 19/14* (2006.01)
(52) U.S. Cl.
CPC .................... *C07H 19/14* (2013.01)
(58) Field of Classification Search
None
See application file for complete search history.

(56) References Cited

U.S. PATENT DOCUMENTS 5,646,128 A * 7/1997 Firestein ................ A61K 31/00
514/45

OTHER PUBLICATIONS

Ugarkar et al.—Journal of Medicinal Chemistry—2000, 43(15), pp. 2883-2893.*
Pudlo et al.—Journal of Medicinal Chemistry, 1988, 31(11), pp. 2086-2092.*
Naus et al.—Journal of Medicinal Chemistry, 2014, 57(3) pp. 1097-1110—published Jan. 7, 2014.*
Paul et al.—Journal of Medicinal Chemistry, 1975, vol. 18(10), pp. 968-973.*
Srikanth et al., Bioorganic and Medicinal Chemistry Letters, vol. 12, 2002, pp. 899-902.*
Caballero et al., Bioorganic & Medicinal Chemistry, 2008, vol. 16(9), pp. 5103-5108.*
Naus, P., et al, Systhesis Cytostatic, Antimicrobial, and Anti-HCV Activity of 6-Substituted 7-(Het)aryl-7deazapurine Ribonucleosides, J.Med.Chem 2014, 57, 1097-1110, ACS Publicatications.

Gerster, J., et al, Pyrrolopyrimidine Nucleosides. 1 The Synthesis of 4-Substituted 7-(β-D-Ribofuranosyl)pyrollo[2,3-d]pyrimidines from Tubercidin, Dept. Chem., 1967 University of Utah, Salt Lake City, Utah.
Varaprasad, C., et al, Synthesis of pyrrolo[2,3-d]pyrimidine nucleoside derivatives as potential anti-HCV agents, Bioorganic Chemistry 35, 2007 25-34 Costa Mesa, California.
Wu, R., et al, Synthesis of a 6-Methyl-7-deaza Analogue of Adenosine That Potently Inhibits Replication of Polio and Dengue Viruses, J.Med. Chem, 2010, 53, 7958-7966, ASC Publications.
Zhang, L., et al, Study on the Synthesis and PKA-I Binding Activities of 5-Alkynykl Tubercidin Analogues, Bioorganic & Medicinal Chemistry 10, 2002, 907-912, National Research Laboratory of Natural and Biomimetic Drugs, School of Pharmaceutical Sciences, Peking University, Beijing, China, 2001, Elsevier Science Ltd.
Krasovskiy, A., et al, A LiCl-Mediated Br/Mg Exchange Reaction for the Preparation of Functionalized Aryl- and Heteroarylmagnesium Compounds from Organic Bromides, Angewandte Chemie, 2004, Wiley-VCH, Verlag GmbH & Co. KGaA, Weinheim.
Bruckl, T., et al, Efficient Synthesis of Deazaguanosine-Derived tRNA Nucleosides PreQo, PreQ1, and Archaeosine Using the Turbo-Grignard Method, Eur.J. Org. Chem. 2010, 6517-6519, Wiley-VCH Verlag GmbH & Co. KGaA, Weinheim.
Western, E., Efficient One-Step Suzuki Arylation of Unprotected Halonucleosides, Using Water-Soluble Palladium Catalysts, J.Org. Chem, 2003, 6767-6774, ACS Publications.
Capek, P., et al, Cross-coupling reactions of unprotected halopurine bases, nucleosides, nucleotides and nucleoside triphosphates with 4-boronophenylalanine in water. Synthesis of (purin-8-yl)- and (purin-6-yl)phenylalanines, Organic & Biomolecular Chemistry, 2006, 4, 2278-2284, The Royal Society of Chemistry, Ustav Oranicke AV.
Seela, F., et al, 7-Functionalized 7-deazapurine β-D and β-L-ribonucleoside related to tubercidin and 7-deazainosine: glycosylation of pyrrolo [2,3-d]pyrimidines with 1-0-acetyl-2,3,5-tri-O-benzoyl-β-D or β-L-ribofuranose, Science Direct, Tetrahedron 63, 2007, 9850-9861, Elsevier Ltd.
Scudiero, D., et al, Evaluation of a Soluble Tetrazolium/Formazan Assay for Cell Growth and Drug Sensitivity in Culture Using Human and Other Tumor Cell Lines, Cancer Research, 48, 4827-4833, 1988, American Association for Cancer.
Stuyver, L, et al, Ribonucleoside Analogue that Blocks Replication of Bovine Viral Diarrhea and Hepatitis C Viruses in Culture, Antimicrobial Agents and Chemotherapy, 2003, 244-254, American Society for Microbiology.
Gottesman, M., et al, Multidrug Resistance in Cancer: Role of ATP-Dependent Transporters, 2002, Macmillan Magazines Ltd.
Muller, P., et al., p53 mutations in cancer, Nature Cell Biology v15, Jan. 2013 Macmillan Publlshers Limited.

(Continued)

*Primary Examiner* — Traviss C McIntosh, III

(74) *Attorney, Agent, or Firm* — Notaro, Michalos & Zaccaria P.C.

(57) ABSTRACT

Compounds of Formula I and a pharmaceutically acceptable salt thereof, an optical isomer thereof, or a mixture of optical isomers thereof, as well as compositions which include such compounds and therapeutic methods that utilize such compounds and/or compositions.

15 Claims, No Drawings

(56) References Cited

OTHER PUBLICATIONS

Denizot, F., et al., Rapid Colorimetric Assay for Cell Growth and Survival Modifcations to the Tetrazolium Dye Proceedure Giving Improved Sensitivity and Reliability, Journal of Immunological Methods, 89, 271-277, 1986, Elsevier Science Publishers B.V.

Noskova, V., et al., In vitro Chemoresistance Profile and Expression/Function of MDR Associated Proteins in Resistant Cell Lines Derived from CCRF-CEM, K562, A549 and MDA MP 231 Parental Cells, Neoplasma, 49, 6, 2002, In Vitro Chemoresistance Profile.

Bhutoria, Savita, Deciphering ligand dependent degree of binding site closure and its implication in inhibitor design: A modeling study on human adenosine kinase, Journal of Molecular Graphics and Modelling, Dec. 2009, p. 577-591, vol. 28.

\* cited by examiner

SUBSTITUTED 7-DEAZAPURINE RIBONUCLEOSIDES FOR THERAPEUTIC USES

FIELD AND BACKGROUND OF THE INVENTION

Field of the Invention

The present invention relates to a new class of anti-cancer compounds and their therapeutic uses.

Background of the Invention

Despite the existence of tens of approved antiproliferation drugs, the treatment of many kinds of leukemia and other cancers is still not very successful. Thus the development of new type of compounds with anti-cancer properties is in demand.

Recently the present inventors discovered a new class of cytostatic compounds, 7-(het)aryl-7-deazaadenosines, of formula A. (See Bourderioux, A.; Nauš, P.; Hocek, M., U.S. 61/171,656 (2009), PCT/CZ2010/000050, WO2010121576 A2; Bourderioux, A.; Nauš, P.; Perlíková, P.; Pohl, R.; Pichová, I.; Votruba, I.; Džubák, P.; Konečný, P.; Hajdúch, M.; Stray, K. M.; Wang, T.; Ray, A. S.; Feng, J. Y.; Birkus, G.; Cihlar, T.; Hocek, M. Synthesis and significant cytostatic activity of 7-hetaryl-7-deazaadenosines. *J. Med. Chem.* 2011, 54, 5498-5507).

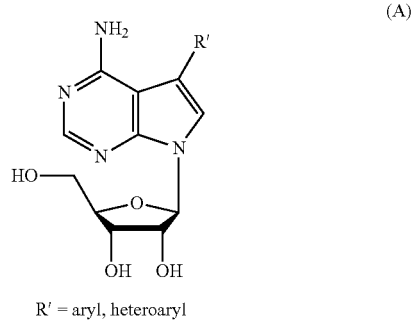

(A)

R' = aryl, heteroaryl

These compounds exhibited nanomolar cytostatic and cytotoxic effect against a broad spectrum of leukemia and solid tumors. These compounds of formula A contained amino group in the position 6 of 7-deazapurine moiety, which can act as hydrogen donor in the formation of hydrogen bonds with target biological structures and thus mimics the bonding of natural nucleoside adenosine (Figure 1).

Weak cytostatic properties of 6-substituted 7-deazapurine ribonucleosides unsubstituted in position 7 were reported. (See Gerster, J. F.; Carpenter, B.; Robins, R. K.; Townsend, L. B. Pyrrolopyrimidine Nucleosides. I. The Synthesis of 4-Substituted 7-(-β-D-Ribofuranosyl) pyrrolo[2,3-d]pyrimidines from Tubercidin. *J. Med. Chem.* 1967, 10, 326-331). In the present document these compounds were used as reference compounds in SAR studies. Analogous 6-substituted 7-deazapurine ribonucleosides bearing cyano group in position 7 were prepared and displayed antiviral properties against HCV (See Varaprasad, C. V. N. S.; Ramasamy, K. S.; Girardet, J. -L.; Gunic, E.; Lai, V.; Zhong, W.; An, H.; Hong, Z., *Bioorg. Chem.* 2007, 35, 25-34). Antiviral activity of 6-methyl-7-deazapurine ribonucleoside was also recently reported (See Wu, R.; Smidansky, E. D.; Oh, H. S.; Takhampunya, R.; Padmanabhan, R.; Cameron, C. E.; Peterson, B. R. Synthesis of a 6-Methyl-7-deaza Analogue of Adenosine That Potently Inhibits Replication of Polio and Dengue Viruses. *J. Med. Chem.* 2010, 53, 7958-7966). This compound was used by the present inventors as reference compound in SAR studies. A series of 7-halogen substituted 6-methoxy-7-deazapurine ribonucleosides was prepared by Seela, but their biological properties were not tested (See Seela, F.; Ming, X. 7-Functionalized 7-deazapurine β-D and β-L-ribonucleosides related to tubercidin and 7-deazainosine: glycosylation of pyrrolo[2,3-d]pyrimidines with 1-O-acetyl-2,3,5-tri-O-benzoyl-β-D or β-L-ribofuranose. *Tetrahedron* 2007, 63, 9850-9861; Zhang, L.; Zhang, Y.; Li, X.; Zhang, L. Study on the Synthesis and PKA-I Binding Activities of 5-Alkynyl Tubercidin Analogues. *Bioorg. Med. Chem.* 2002, 10, 907-912). 5-iodo-4-methoxy-7-(β-D-ribofuranosyl)-7H-pyrrolo[2,3-d]pyrimidine was used by the present inventors either as a starting material or as a reference compound is SAR studies.

SUMMARY OF THE INVENTION

Present invention provides new 6-substituted 7-(het)aryl-7-deazapurine ribonucleosides exhibiting strong cytostatic and cytotoxic effects on cell lines preferentially of tumor origin and on broad spectrum of cancers of various histogenetic origin.

Compounds of the present invention differ substantially from those 7-(het)aryl-7-deazaadenosines of formula A by the nature of substituent in position 6 of 7-deazapurine. The amino group (H-bond donor) is replaced by H-bond acceptors (methoxy, methylsulfanyl, dimethylamino), methylamino group (which can serve as either a donor or acceptor) or isosteric but non-polar methyl group (Figure 2). Thus different type of interaction with target biological system can be anticipated for compounds of the present invention compared to 7-deazaadenosines of formula A.

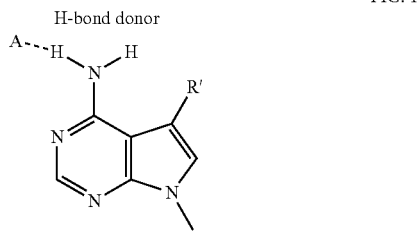

FIG. 1

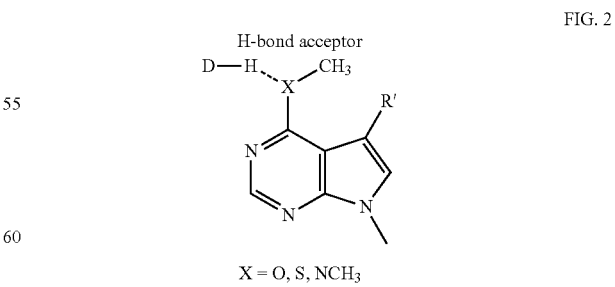

FIG. 2

X = O, S, NCH₃

This invention provides substituted 7-deazapurine ribonucleosides. Accordingly, in one embodiment the invention provides a compound of the invention, which is a compound of formula I:

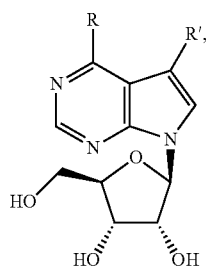

(I)

wherein,
R is methylsulfanyl, methoxy, methylamino, dimethylamino or methyl;
R' is furan-2-yl, furan-3-yl, thiophen-2-yl, thiophen-3-yl, phenyl, benzofuran-2-yl, ethynyl, iodine or bromine; or
a pharmaceutically acceptable salt thereof; or an optical isomer thereof; or a mixture of optical isomers;
with the proviso that if R' is iodine or bromine, R is not methoxy.

In a preferred embodiment, the present invention provides following compounds of formula I:
5-(Furan-2-yl)-4-methoxy-7-(β-D-ribofuranosyl)-7H-pyrrolo[2,3-d]pyrimidine
5-(Furan-3-yl)-4-methoxy-7-(β-D-ribofuranosyl)-7H-pyrrolo[2,3-d]pyrimidine
4-Methoxy-7-(β-D-ribofuranosyl)-5-(thiophen-2-yl)-7H-pyrrolo[2,3-d]pyrimidine
4-Methoxy-7-(β-D-ribofuranosyl)-5-(thiophen-3-yl)-7H-pyrrolo[2,3-d]pyrimidine
4-Methoxy-5-phenyl-7-(β-D-ribofuranosyl)-7H-pyrrolo[2,3-d]pyrimidine
5-(Benzofuran-2-yl)-4-methoxy-7-(β-D-ribofuranosyl)-7H-pyrrolo[2,3-d]pyrimidine
5-Ethynyl-4-methoxy-7-(β-D-ribofuranosyl)-7H-pyrrolo[2,3-d]pyrimidine
5-Iodo-4-methylsulfanyl-7-(β-D-ribofuranosyl)-7H-pyrrolo[2,3-d]pyrimidine
5-(Furan-2-yl)-4-methylsulfanyl-7-(β-D-ribofuranosyl)-7H-pyrrolo[2,3-d]pyrimidine
5-(Furan-3-yl)-4-methylsulfanyl-7-(β-D-ribofuranosyl)-7H-pyrrolo[2,3-d]pyrimidine
4-Methylsulfanyl-7-(β-D-ribofuranosyl)-5-(thiophen-2-yl)-7H-pyrrolo[2,3-d]pyrimidine
4-Methylsulfanyl-7-(β-D-ribofuranosyl)-5-(thiophen-3-yl)-7H-pyrrolo[2,3-d]pyrimidine
4-Methylsulfanyl-5-phenyl-7-(β-D-ribofuranosyl)-7H-pyrrolo[2,3-d]pyrimidine
5-(Benzofuran-2-yl)-4-methylsulfanyl-7-(β-D-ribofuranosyl)-7H-pyrrolo[2,3-d]pyrimidine
5-Ethynyl-4-methylsulfanyl-7-(β-D-ribofuranosyl)-7H-pyrrolo[2,3-d]pyrimidine
5-Iodo-4-methylamino-7-(β-D-ribofuranosyl)-7H-pyrrolo[2,3-d]pyrimidine
5-(Furan-2-yl)-4-methylamino-7-(β-D-ribofuranosyl)-7H-pyrrolo[2,3-d]pyrimidine
5-(Furan-3-yl)-4-methylamino-7-(β-D-ribofuranosyl)-7H-pyrrolo[2,3-d]pyrimidine
4-Methylamino-7-(β-D-ribofuranosyl)-5-(thiophen-2-yl)-7H-pyrrolo[2,3-d]pyrimidine
4-Methylamino-7-(β-D-ribofuranosyl)-5-(thiophen-3-yl)-7H-pyrrolo[2,3-d]pyrimidine
4-Methylamino-5-phenyl-7-(β-D-ribofuranosyl)-7H-pyrrolo[2,3-d]pyrimidine
5-(Benzofuran-2-yl)-4-methylamino-7-(β-D-ribofuranosyl)-7H-pyrrolo[2,3-d]pyrimidine
5-Ethynyl-4-methylamino-7-(β-D-ribofuranosyl)-7H-pyrrolo[2,3-d]pyrimidine
4-Dimethylamino-5-iodo-7-(β-D-ribofuranosyl)-7H-pyrrolo[2,3-d]pyrimidine
4-Dimethylamino-5-(furan-2-yl)-7-(β-D-ribofuranosyl)-7H-pyrrolo[2,3-d]pyrimidine
4-Dimethylamino-5-(furan-3-yl)-7-(β-D-ribofuranosyl)-7H-pyrrolo[2,3-d]pyrimidine
4-Dimethylamino-7-(β-D-ribofuranosyl)-5-(thiophen-2-yl)-7H-pyrrolo[2,3-d]pyrimidine
4-Dimethylamino-7-(β-D-ribofuranosyl)-5-(thiophen-3-yl)-7H-pyrrolo[2,3-d]pyrimidine
4-Dimethylamino-5-phenyl-7-(β-D-ribofuranosyl)-7H-pyrrolo[2,3-d]pyrimidine
5-(Benzofuran-2-yl)-4-dimethylamino-7-(β-D-ribofuranosyl)-7H-pyrrolo[2,3-d]pyrimidine
4-Dimethylamino-5-ethynyl-7-(β-D-ribofuranosyl)-7H-pyrrolo[2,3-d]pyrimidine
5-Iodo-4-methyl-7-(β-D-ribofuranosyl)-7H-pyrrolo[2,3-d]pyrimidine
5-Bromo-4-methyl-7-(β-D-ribofuranosyl)-7H-pyrrolo[2,3-d]pyrimidine
5-(Furan-2-yl)-4-methyl-7-(β-D-ribofuranosyl)-7H-pyrrolo[2,3-d]pyrimidine
5-(Furan-3-yl)-4-methyl-7-(β-D-ribofuranosyl)-7H-pyrrolo[2,3-d]pyrimidine
4-Methyl-7-(β-D-ribofuranosyl)-5-(thiophen-2-yl)-7H-pyrrolo[2,3-d]pyrimidine
4-Methyl-7-(β-D-ribofuranosyl)-5-(thiophen-3-yl)-7H-pyrrolo[2,3-d]pyrimidine
4-Methyl-5-phenyl-7-(β-D-ribofuranosyl)-7H-pyrrolo[2,3-d]pyrimidine
5-(Benzofuran-2-yl)-4-methyl-7-(β-D-ribofuranosyl)-7H-pyrrolo[2,3-d]pyrimidine
5-Ethynyl-4-methyl-7-(β-D-ribofuranosyl)-7H-pyrrolo[2,3-d]pyrimidine Additionally, the present invention provides a compound of formula I for use as a medicament.

Present invention provides a compound of formula I for inhibition of pathological cell proliferation of tumor/non-tumor/cancer origin and for treatment of tumor/non-tumor/cancer disease associated with cell hyperproliferation.

Present invention provides a compound of formula I for the preparation of a medicament for treatment of tumor/cancer diseases, covering e.g. epithelial, mesenchymal and neuroectoderm origin tumors.

The invention also provides a method of inhibiting tumor/cancer growth or cell proliferation in tumor/cancer cells in vitro or in vivo comprising contacting a subject with a compound of formula I, or a pharmaceutically acceptable salt thereof.

The invention also provides a method of treating a neoplastic disease or cellular proliferation disease in a subject comprising administering to the subject a therapeutically effective amount of a compound of formula 1.

The invention also provides a method of treating a tumor or cellular in a subject comprising administering to the subject a therapeutically effective amount of a compound of formula 1.

The invention also provides the use of a compound of formula I, or a pharmaceutically acceptable salt thereof, to prepare a medicament for inhibiting tumor/cancer cell growth or cell proliferation in tumor/cancer cells, slowing down cell cycle progression in tumor/cancer cells, and for treating cancer in a subject.

The present invention provides a pharmaceutical composition comprising a therapeutically effective amount of a compound of formula I and one or more pharmaceutically acceptable carriers/excipients.

The invention also provides the use of a pharmaceutical composition mentioned above for inhibition of pathological cell proliferation of tumor/non-tumor/cancer origin and/or for treatment of tumor/non tumor/cancer disease associated with cell hyperproliferation.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto (e.g., phenol or hydroxyamic acid). Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in Remington's Pharmaceutical Sciences, 20th ed., Mack Publishing Company, Easton, Pa., (1985), which is herein incorporated by reference.

The term "therapeutically effective amount" of a compound of the present invention refers to an amount of the compound of the present invention that will elicit the biological or medical response of a subject, or ameliorate symptoms, slow or delay disease progression, or prevent a disease, etc. In a preferred embodiment, the "effective amount" refers to the amount that inhibits or reduces proliferation of cancer cells, or inhibiting or reducing tumor/cancer growth in vitro or in vivo, or inhibiting or reducing a neoplastic disease in a subject such as a mammal. In another preferred embodiment, it also refers to the amount that reduces the primary tumor/cancer size, inhibits cancer cell infiltration into peripheral organs, slows or stops tumor metastasis, or relieves at least to some extent one or more symptoms associated with tumor or cancer, etc.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "a disorder" or "a disease" refers to any derangement or abnormality of function; a morbid physical or mental state. See Dorland's Illustrated Medical Dictionary, (W.B. Saunders Co. 27th ed. 1988).

As used herein, the term "inhibition" or "inhibiting" refers to the reduction or suppression of a given condition, symptom, or disease, or a significant decrease in the baseline activity of a biological activity or process. In one embodiment, it refers to ability to cause reduction of a tumor or cancer growth, or reduction of the tumor or cancer size.

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

As used herein, the term "pharmaceutically acceptable carrier/excipient" includes any and all solvents, dispersion media, coatings, surfactants, antioxidants, preservatives (e.g., antibacterial agents, antifungal agents), isotonic agents, absorption delaying agents, salts, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except in so far as any conventional carrier is incompatible with the active ingredient, its use in the therapeutic or pharmaceutical compositions is contemplated.

In one embodiment, the present invention provides a compound of formula I as a prodrug or in other suitable form, which releases active compound in vivo.

DETAILED DESCRIPTION OF THE INVENTION

Compounds of present invention can be prepared as follows:

Numbering of Compounds

Following numbering of compounds is used:

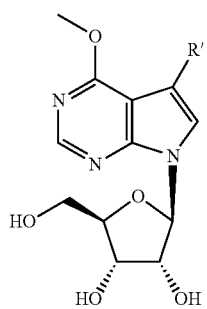
1a-h

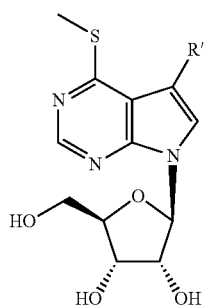
2a-h

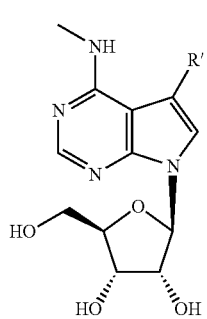
3a-h

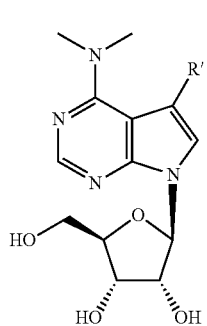
4a-h

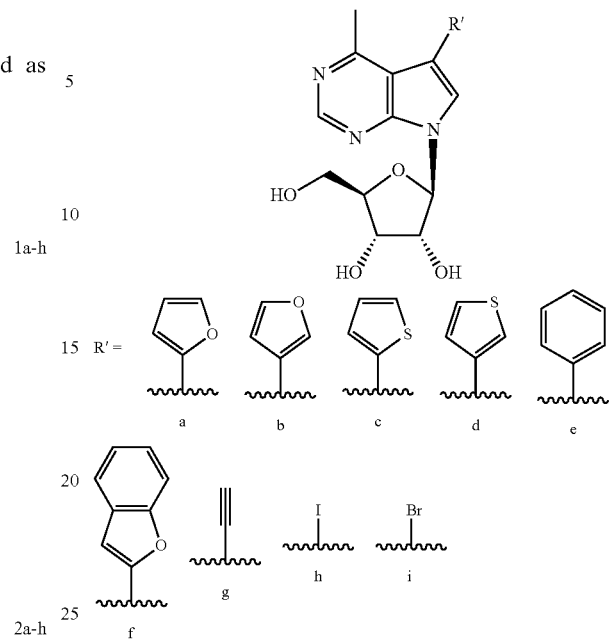
5a-i

Synthesis of Compounds

The synthetic strategy for preparation of 6-monosubstituted 7-(hetaryl)-7-deazapurine ribonucleosides 1-5 was based on aqueous-phase Suzuki cross-coupling reactions of the corresponding 6-substituted 7-iodo-7-deazapurine ribonucleosides 1h-4h and bromo analogue 5i. Key starting 6-substituted 7-iodo-7-deazapurine ribonucleosides 1h-4h were prepared by the reactions of 4-chloro-5-iodo-7-(2,3,5-tri-O-benzoyl-β-D-ribofuranosyl)-7H-pyrrolo[2,3-d]pyrimidine 6 (Seela, F.; Ming, X. *Tetrahedron* 2007, 63, 9850-9861) with corresponding nucleophilic reagents (Scheme 1). Concomitant nucleophilic debenzoylation of the sugar proceeded in all cases under the reaction conditions, affording directly free nucleosides.

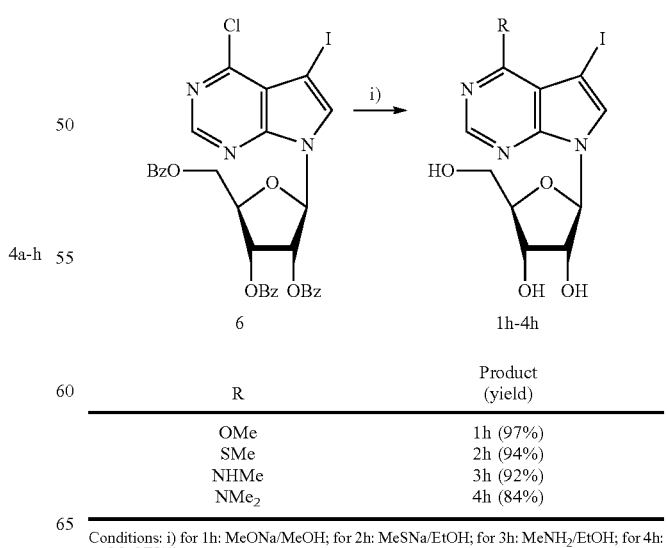

Scheme 1.

| R | Product (yield) |
|---|---|
| OMe | 1h (97%) |
| SMe | 2h (94%) |
| NHMe | 3h (92%) |
| NMe$_2$ | 4h (84%) |

Conditions: i) for 1h: MeONa/MeOH; for 2h: MeSNa/EtOH; for 3h: MeNH$_2$/EtOH; for 4h: aq Me$_2$NH/dioxane.

The synthesis of 7-halogenated 6-methyl-7-deazapurine ribonucleosides was more complicated due to the need for cross-coupling methylation at position 6, which on 6-chloro-7-iodo-7-deazapurine nucleoside 6 would not proceed chemoselectively. Thus we decided to first selectively hydrodeiodinate 6 followed by C-6 methylation and re-introduction of the halogen at position 7 (Scheme 2). De-iodination of 6 was achieved by iodine-magnesium exchange reaction using Knochel's Turbo-Grignard reagent (iPrMgCl.LiCl) (Ref.: (a) Krasovskiy, A.; Knochel, P. A LiCl-Mediated Br/Mg Exchange Reaction for the Preparation of Functionalized Aryl- and Heteroarylmagnesium Compounds from Organic Bromides. *Angew. Chem., Int. Ed.* 2004, 43, 3333-3336. (b) Brückl, T; Thoma, I.; Wagner, A. J.; Knochel, P.; Carell, T. Efficient Synthesis of Deazaguanosine-Derived tRNA Nucleosides PreQ$_0$, PreQ$_1$, and Archaeosine Using the Turbo-Grignard Method. *Eur. J. Org. Chem.* 2010, 6517-6519) and subsequent hydrolysis of magnesium intermediate to give 6-chloro-7-deazapurine riboside 7 (Tolman, R. L.; Tolman, G. L.; Robins, R. K.; Townsend, L. B. Pyrrolopyrimidine Nucleosides. VI. Synthesis of 1,3 and 7-β-D-Ribofuranosylpyrrolo[2,3-d]pyrimidines via Silylated Intermediates. *J. Heterocycl. Chem.* 1970, 7, 799-806) in almost quantitative yield without need for purification. The 6-chloro-7-deazapurine riboside 7 was converted to 6-methyl derivative 8 by palladium catalyzed reaction with trimethylaluminum in 92% yield, and the follow-up Zemplén deprotection furnished free 6-methyl-7-deazapurine ribonucleoside 9 (Wu, R.; Smidansky, E. D.; Oh, H. S.; Takhampunya, R.; Padmanabhan, R.; Cameron, C. E.; Peterson, B. R. Synthesis of a 6-Methyl-7-deaza Analogue of Adenosine That Potently Inhibits Replication of Polio and Dengue Viruses. *J. Med. Chem.* 2010, 53, 7958-7966) in 97% yield. Compound 9 was then brominated by N-bromosuccinimide (NBS) in DMF to give 7-bromo derivative 5i in 66% yield. Analogous 7-iodo derivative 5 h was prepared by treatment with N-iodosuccinimide (NIS) but the reaction was more sluggish giving 5 h in 58% yield with 18% recovery of unreacted 9.

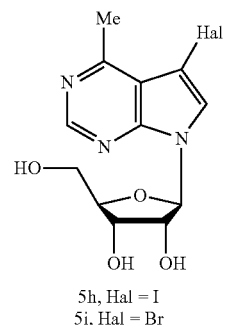

5h, Hal = I
5i, Hal = Br

Conditions: (i) 1. iPrMgCl•LiCl, THF, -10° C. 2. aq work-up (quant); (ii) AlMe$_3$, Pd(PPh$_3$)$_4$, THF, 100° C. (92%); (iii) MeONa, MeOH, rt (97%); (iv) for 5h: NIS, DMF, rt (58%); for 5i: NBS, DMF, rt (66%).

The halogenated nucleoside intermediates 1h-4h and 5i served as starting points for the synthesis of the target 7-(het)aryl 7-deazapurine ribonucleosides via the Suzuki-Miyaura reactions with (het)aryl boronic acids (Scheme 3). The Pd-catalyzed reactions were conducted under aqueous conditions in presence of TPPTS and sodium carbonate (ref.: (a) Western, E. C.; Daft, J. R.; Johnson, E. M.; Gannett, P. M.; Shaughnessy, K. H. Efficient One-Step Suzuki Arylation of Unprotected Halonucleosides, Using Water-Soluble palladium catalysts. *J. Org. Chem.* 2003, 68, 6767-6774. (b) Čapek, P.; Pohl, R.; Hocek, M. Cross-coupling Reactions of Unprotected Halopurine Bases, Nucleosides, Nucleotides and Nucleoside Triphosphates with 4-Boronophenylalanine in Water. Synthesis of (Purin-8-yl)- and (Purin-6-yl)phenylalanines. *Org. Biomol. Chem.* 2006, 4, 2278-2284). The reactions in a water/acetonitrile 2:1 mixture at 100° C. proceeded smoothly within 3 h to give the desired library of 30 (5×6) 7-(het)aryl derivatives 1-5a-f in moderate to good yields. In most cases, except for methylaminoderivatives 3a-f, the reaction mixtures also contained minor by-products of concomitant reductive deiodination, which were easily removed by chromatography. For methylsulfanyl derivatives 2a, 2c and 2f, the cross-coupling reactions didn't reach full conversions of starting iodide 2h and separation from the products required crystallization.

Scheme 2.

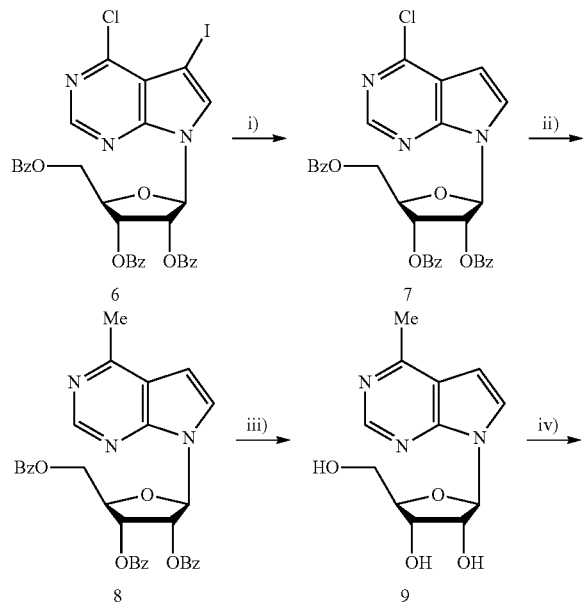

Scheme 3. Suzuki cross-coupling reactions of 1h-4h or 5i

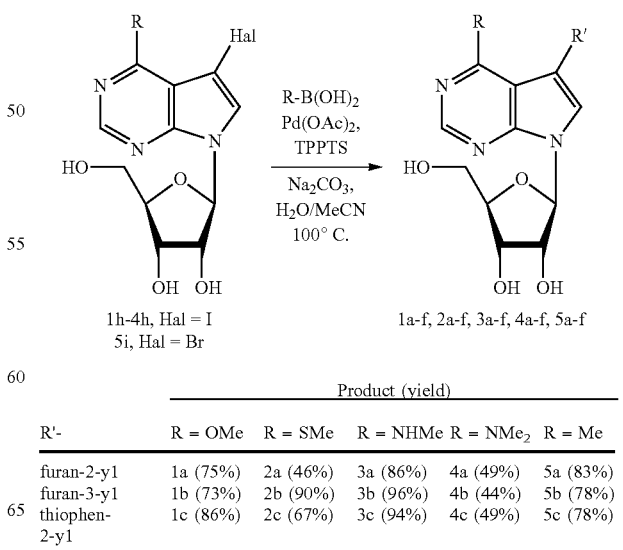

1h-4h, Hal = I
5i, Hal = Br 1a-f, 2a-f, 3a-f, 4a-f, 5a-f

| R'- | R = OMe | R = SMe | R = NHMe | R = NMe$_2$ | R = Me |
|---|---|---|---|---|---|
| furan-2-yl | 1a (75%) | 2a (46%) | 3a (86%) | 4a (49%) | 5a (83%) |
| furan-3-yl | 1b (73%) | 2b (90%) | 3b (96%) | 4b (44%) | 5b (78%) |
| thiophen-2-yl | 1c (86%) | 2c (67%) | 3c (94%) | 4c (49%) | 5c (78%) |

Scheme 3. Suzuki cross-coupling reactions of 1h-4h or 5i

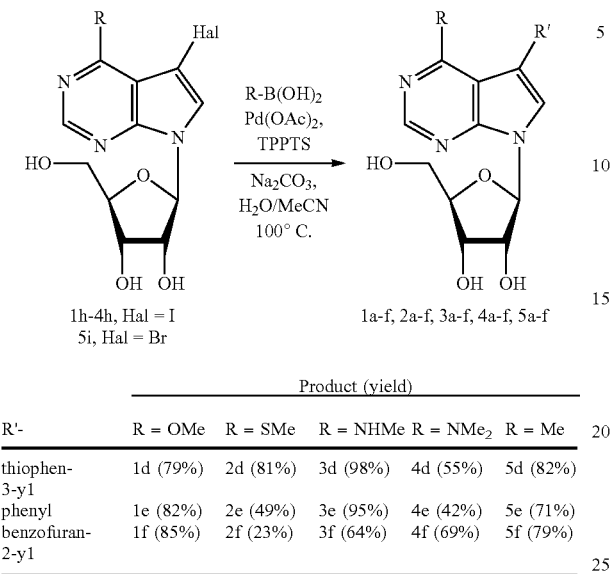

1h-4h, Hal = I
5i, Hal = Br 1a-f, 2a-f, 3a-f, 4a-f, 5a-f

| R'- | Product (yield) | | | | |
|---|---|---|---|---|---|
| | R = OMe | R = SMe | R = NHMe | R = NMe₂ | R = Me |
| thiophen-3-yl | 1d (79%) | 2d (81%) | 3d (98%) | 4d (55%) | 5d (82%) |
| phenyl | 1e (82%) | 2e (49%) | 3e (95%) | 4e (42%) | 5e (71%) |
| benzofuran-2-yl | 1f (85%) | 2f (23%) | 3f (64%) | 4f (69%) | 5f (79%) |

Ethynyl derivatives 1g-5g were prepared from the corresponding iododeazapurines 1h-5h by Sonogashira reaction with (trimethylsilyl)acetylene followed by cleavage of the trimethylsilyl group by treatment with $K_2CO_3$ in methanol (Scheme 4). It is noteworthy that methyl derivative 5g had to be synthesized from a more reactive iododeazapurine 5h because the bromo-derivative 5i failed to react under these conditions.

Scheme 4.

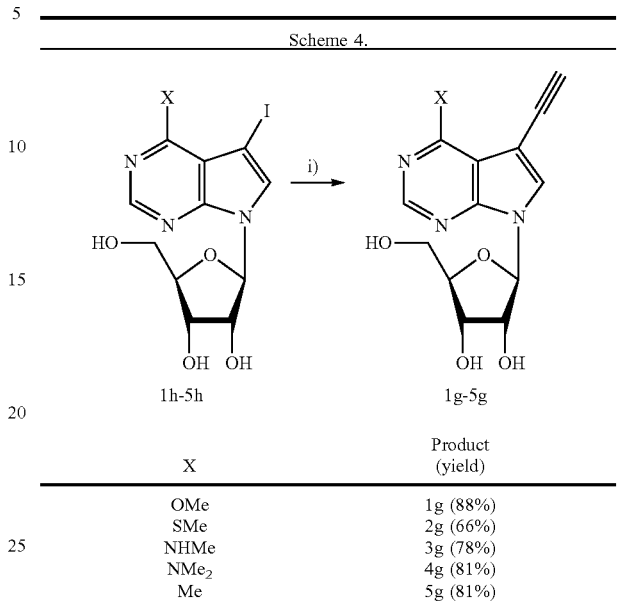

1h-5h 1g-5g

| X | Product (yield) |
|---|---|
| OMe | 1g (88%) |
| SMe | 2g (66%) |
| NHMe | 3g (78%) |
| NMe₂ | 4g (81%) |
| Me | 5g (81%) |

Conditions: i) 1. trimethylsilylacetylene, $PdCl_2(PPh_3)_2$, CuI, $NEt_3$, DMF, rt. 2. $K_2CO_3$, MeOH, rt. The yields are given as overall isolated yields over the two steps.

Survey of Compounds in Examples:

| Example No | Compound number | Structure | Systematic Name |
|---|---|---|---|
| 1 | 1a | 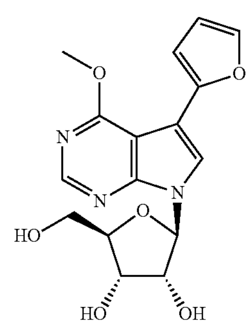 [SMILES: COc1ncnc2c1c(-c1ccco1)cn2[C@@H]1O[C@H](CO)[C@@H](O)[C@H]1O] | 5-(Furan-2-yl)-4-methoxy-7-(β-D-ribofuranosyl)-7H-pyrrolo[2,3-d]pyrimidine |
| 2 | 1b | 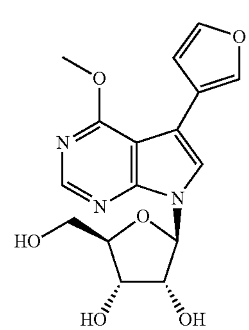 [SMILES: COc1ncnc2c1c(-c1ccoc1)cn2[C@@H]1O[C@H](CO)[C@@H](O)[C@H]1O] | 5-(Furan-3-yl)-4-methoxy-7-(β-D-ribofuranosyl)-7H-pyrrolo[2,3-d]pyrimidine |

-continued

| Example No | Compound number | Structure | Systematic Name |
|---|---|---|---|
| 3 | 1c | 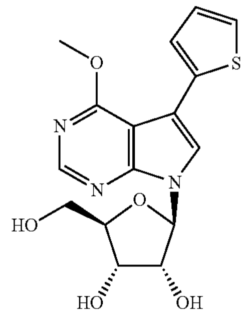 [SMILES: COc1ncnc2c1c(-c1cccs1)cn2[C@@H]1O[C@H](CO)[C@@H](O)[C@H]1O] | 4-Methoxy-7-(β-D-ribofuranosyl)-5-(thiophen-2-yl)-7H-pyrrolo[2,3-d]pyrimidine |
| 4 | 1d | 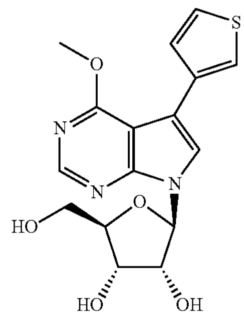 [SMILES: COc1ncnc2c1c(-c1ccsc1)cn2[C@@H]1O[C@H](CO)[C@@H](O)[C@H]1O] | 4-Methoxy-7-(β-D-ribofuranosyl)-5-(thiophen-3-yl)-7H-pyrrolo[2,3-d]pyrimidine |
| 5 | 1e | 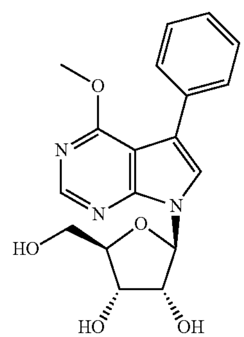 [SMILES: COc1ncnc2c1c(-c1ccccc1)cn2[C@@H]1O[C@H](CO)[C@@H](O)[C@H]1O] | 4-Methoxy-5-phenyl-7-(β-D-ribofuranosyl)-7H-pyrrolo[2,3-d]pyrimidine |
| 6 | 1f | 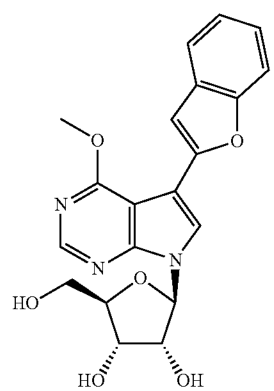 | 5-(Benzofuran-2-yl)-4-methoxy-7-(β-D-ribofuranosyl)-7H-pyrrolo[2,3-d]pyrimidine |

-continued

| Example No | Compound number | Structure | Systematic Name |
|---|---|---|---|
| 7 | 1g | 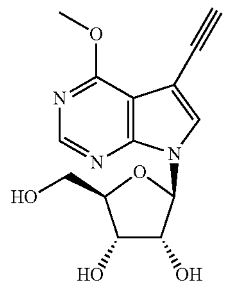 | 5-Ethynyl-4-methoxy-7-(β-D-ribofuranosyl)-7H-pyrrolo[2,3-d]pyrimidine |
| 8 | 2h | 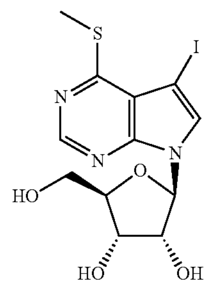 [SMILES: CSc1ncnc2c1c(I)cn2[C@@H]1O[C@H](CO)[C@@H](O)[C@H]1O] | 5-Iodo-4-methylsulfanyl-7-(β-D-ribofuranosyl)-7H-pyrrolo[2,3-d]pyrimidine |
| 9 | 2a | 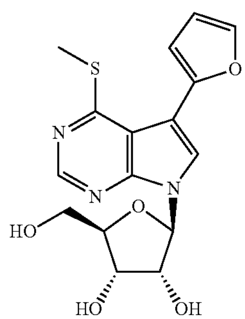 [SMILES: CSc1ncnc2c1c(-c1ccco1)cn2[C@@H]1O[C@H](CO)[C@@H](O)[C@H]1O] | 5-(Furan-2-yl)-4-methylsulfanyl-7-(β-D-ribofuranosyl)-7H-pyrrolo[2,3-d]pyrimidine |
| 10 | 2b | 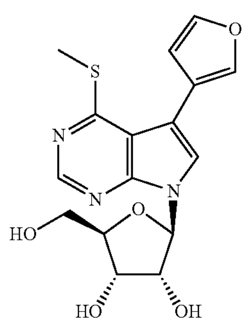 [SMILES: CSc1ncnc2c1c(-c1ccoc1)cn2[C@@H]1O[C@H](CO)[C@@H](O)[C@H]1O] | 5-(Furan-3-yl)-4-methylsulfanyl-7-(β-D-ribofuranosyl)-7H-pyrrolo[2,3-d]pyrimidine |
| 11 | 2c | 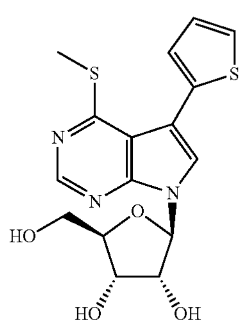 [SMILES: CSc1ncnc2c1c(-c1cccs1)cn2[C@@H]1O[C@H](CO)[C@@H](O)[C@H]1O] | 4-Methylsulfanyl-7-(β-D-ribofuranosyl)-5-(thiophen-2-yl)-7H-pyrrolo[2,3-d]pyrimidine |

| Example No | Compound number | Structure | Systematic Name |
|---|---|---|---|
| 12 | 2d | 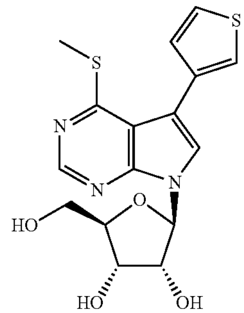 [SMILES: CSc1ncnc2c1c(-c1ccsc1)cn2[C@@H]1O[C@H](CO)[C@@H](O)[C@H]1O] | 4-Methylsulfanyl-7-(β-D-ribofuranosyl)-5-(thiophen-3-yl)-7H-pyrrolo[2,3-d]pyrimidine |
| 13 | 2e | 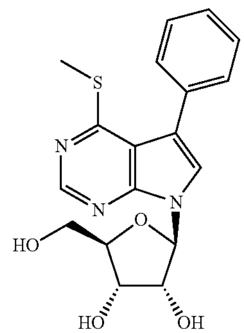 [SMILES: CSc1ncnc2c1c(-c1ccccc1)cn2[C@@H]1O[C@H](CO)[C@@H](O)[C@H]1O] | 4-Methylsulfanyl-5-phenyl-7-(β-D-ribofuranosyl)-7H-pyrrolo[2,3-d]pyrimidine |
| 14 | 2f | 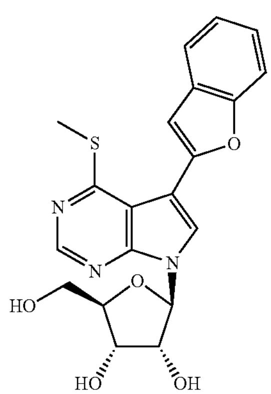 [SMILES: CSc1ncnc2c1c(-c1cc3ccccc3o1)cn2[C@@H]1O[C@H](CO)[C@@H](O)[C@H]1O] | 5-(Benzofuran-2-yl)-4-methylsulfanyl-7-(β-D-ribofuranosyl)-7H-pyrrolo[2,3-d]pyrimidine |
| 15 | 2g | 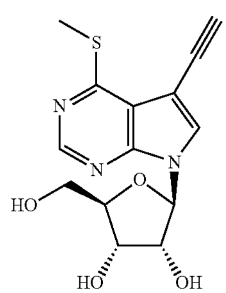 | 5-Ethynyl-4-methylsulfanyl-7-(β-D-ribofuranosyl)-7H-pyrrolo[2,3-d]pyrimidine |

-continued

| Example No | Compound number | Structure | Systematic Name |
|---|---|---|---|
| 16 | 3h | 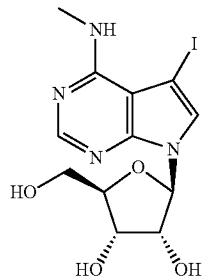 [SMILES: CNc1ncnc2c1c(I)cn2[C@@H]1O[C@H](CO)[C@@H](O)[C@H]1O] | 5-Iodo-4-methylamino-7-(β-D-ribofuranosyl)-7H-pyrrolo[2,3-d]pyrimidine |
| 17 | 3a | 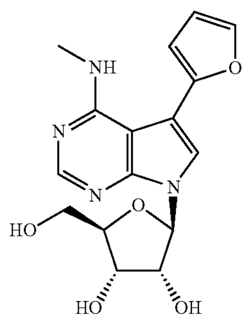 [SMILES: CNc1ncnc2c1c(-c1ccco1)cn2[C@@H]1O[C@H](CO)[C@@H](O)[C@H]1O] | 5-(Furan-2-yl)-4-methylamino-7-(β-D-ribofuranosyl)-7H-pyrrolo[2,3-d]pyrimidine |
| 18 | 3b | 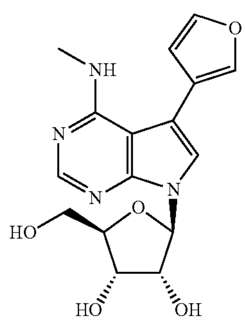 [SMILES: CNc1ncnc2c1c(-c1ccoc1)cn2[C@@H]1O[C@H](CO)[C@@H](O)[C@H]1O] | 5-(Furan-3-yl)-4-methylamino-7-(β-D-ribofuranosyl)-7H-pyrrolo[2,3-d]pyrimidine |
| 19 | 3c | 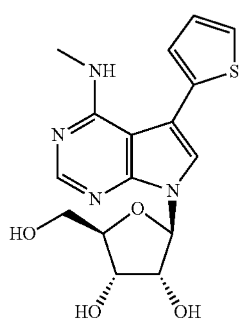 [SMILES: CNc1ncnc2c1c(-c1cccs1)cn2[C@@H]1O[C@H](CO)[C@@H](O)[C@H]1O] | 4-Methylamino-7-(β-D-ribofuranosyl)-5-(thiophen-2-yl)-7H-pyrrolo[2,3-d]pyrimidine |
| 20 | 3d | 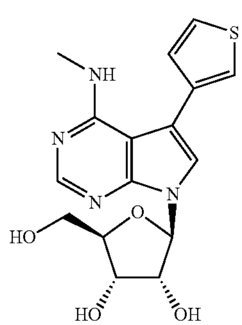 [SMILES: CNc1ncnc2c1c(-c1ccsc1)cn2[C@@H]1O[C@H](CO)[C@@H](O)[C@H]1O] | 4-Methylamino-7-(β-D-ribofuranosyl)-5-(thiophen-3-yl)-7H-pyrrolo[2,3-d]pyrimidine |

-continued

| Example No | Compound number | Structure | Systematic Name |
|---|---|---|---|
| 21 | 3e | 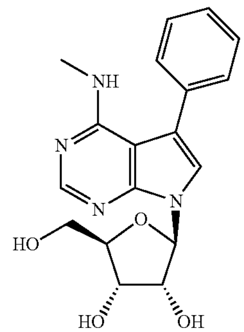 [SMILES: CNc1ncnc2c1c(-c1ccccc1)cn2[C@@H]1O[C@H](CO)[C@@H](O)[C@H]1O] | 4-Methylamino-5-phenyl-7-(β-D-ribofuranosyl)-7H-pyrrolo[2,3-d]pyrimidine |
| 22 | 3f | 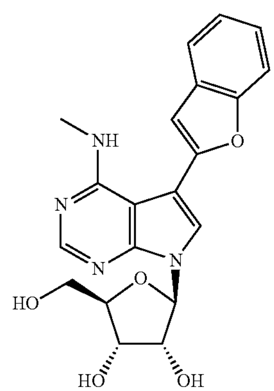 [SMILES: CNc1ncnc2c1c(-c1cc3ccccc3o1)cn2[C@@H]1O[C@H](CO)[C@@H](O)[C@H]1O] | 5-(Benzofuran-2-yl)-4-methylamino-7-(β-D-ribofuranosyl)-7H-pyrrolo[2,3-d]pyrimidine |
| 23 | 3g | 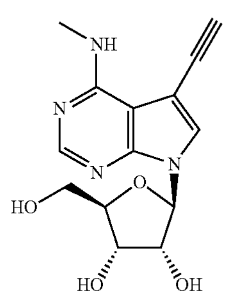 [SMILES: C#Cc1cn([C@@H]2O[C@H](CO)[C@@H](O)[C@H]2O)c2ncnc(NC)c12] | 5-Ethynyl-4-methylamino-7-(β-D-ribofuranosyl)-7H-pyrrolo[2,3-d]pyrimidine |
| 24 | 4h | 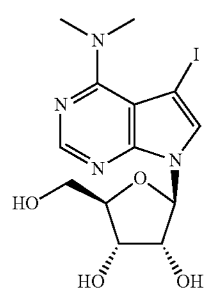 [SMILES: CN(C)c1ncnc2c1c(I)cn2[C@@H]1O[C@H](CO)[C@@H](O)[C@H]1O] | 4-Dimethylamino-5-iodo-7-(β-D-ribofuranosyl)-7H-pyrrolo[2,3-d]pyrimidine |

-continued

| Example No | Compound number | Structure | Systematic Name |
|---|---|---|---|
| 25 | 4a | 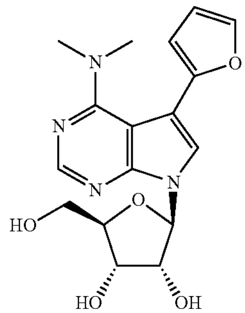 [SMILES: CN(C)c1ncnc2c1c(-c1ccco1)cn2[C@@H]1O[C@H](CO)[C@@H](O)[C@H]1O] | 4-Dimethylamino-5-(furan-2-yl)-7-(β-D-ribofuranosyl)-7H-pyrrolo[2,3-d]pyrimidine |
| 26 | 4b | 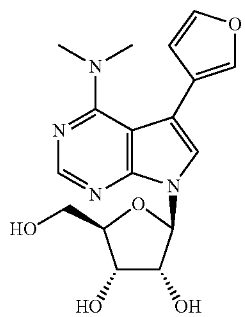 [SMILES: CN(C)c1ncnc2c1c(-c1ccoc1)cn2[C@@H]1O[C@H](CO)[C@@H](O)[C@H]1O] | 4-Dimethylamino-5-(furan-3-yl)-7-(β-D-ribofuranosyl)-7H-pyrrolo[2,3-d]pyrimidine |
| 27 | 4c | 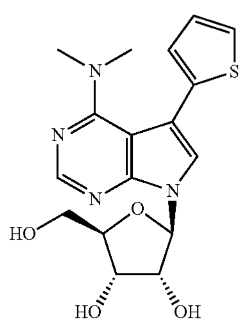 [SMILES: CN(C)c1ncnc2c1c(-c1cccs1)cn2[C@@H]1O[C@H](CO)[C@@H](O)[C@H]1O] | 4-Dimethylamino-7-(β-D-ribofuranosyl)-5-(thiophen-2-yl)-7H-pyrrolo[2,3-d]pyrimidine |
| 28 | 4d | 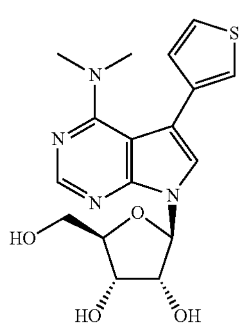 [SMILES: CN(C)c1ncnc2c1c(-c1ccsc1)cn2[C@@H]1O[C@H](CO)[C@@H](O)[C@H]1O] | 4-Dimethylamino-7-(β-D-ribofuranosyl)-5-(thiophen-2-yl)-7H-pyrrolo[2,3-c]pyrimidine |

-continued

| Example No | Compound number | Structure | Systematic Name |
|---|---|---|---|
| 29 | 4e | 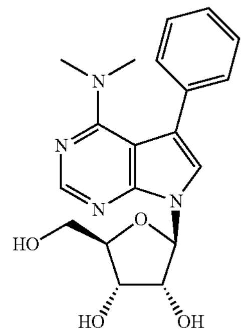 [SMILES: CN(C)c1ncnc2c1c(-c1ccccc1)cn2[C@@H]1O[C@H](CO)[C@@H](O)[C@H]1O] | 4-Dimethylamino-5-phenyl-7-(β-D-ribofuranosyl)-7H-pyrrolo[2,3-d]pyrimidine |
| 30 | 4f | 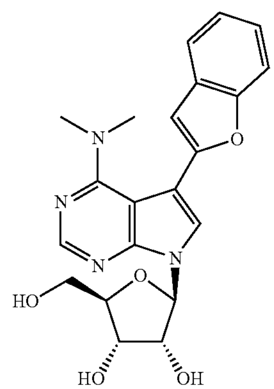 [SMILES: CN(C)c1ncnc2c1c(-c1cc3ccccc3o1)cn2[C@@H]1O[C@H](CO)[C@@H](O)[C@H]1O] | 5-(Benzofuran-2-yl)-4-dimethylamino-7-(β-D-ribofuranosyl)-7H-pyrrolo[2,3-d]pyrimidine |
| 31 | 4g | 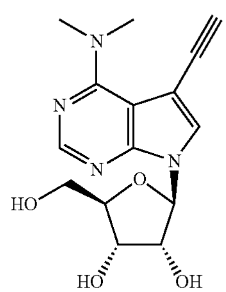 [SMILES: C#Cc1cn([C@@H]2O[C@H](CO)[C@@H](O)[C@H]2O)c2ncnc(N(C)C)c12] | 4-Dimethylamino-5-ethynyl-7-(β-D-ribofuranosyl)-7H-pyrrolo[2,3 d]pyrimidine |
| 32 | 5h | 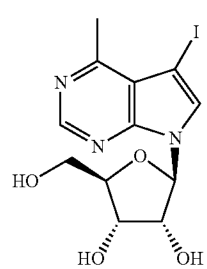 [SMILES: Cc1ncnc2c1c(I)cn2[C@@H]1O[C@H](CO)[C@@H](O)[C@H]1O] | 5-Iodo-4-methyl-7-(β-D-ribofuranosyl)-7H-pyrrolo[2,3-d]pyrimidine |

-continued

| Example No | Compound number | Structure | Systematic Name |
|---|---|---|---|
| Intermediate 1 | 7 | 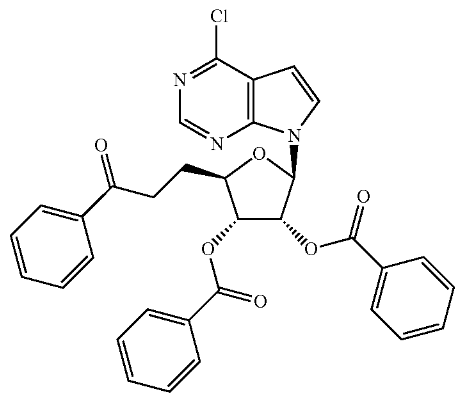 [SMILES: O=C(CC[C@H]1O[C@@H](n2ccc3c(Cl)ncnc32)[C@H](OC(=O)c2ccccc2)[C@@H]1OC(=O)c1ccccc1)c1ccccc1] | 4-Chloro-7-(2,3,5-tri-O-benzoyl-(β-D-ribofuranosyl)-7H-pyrrolo[2,3-d]pyrimidine |
| Intermediate 2 | 8 | 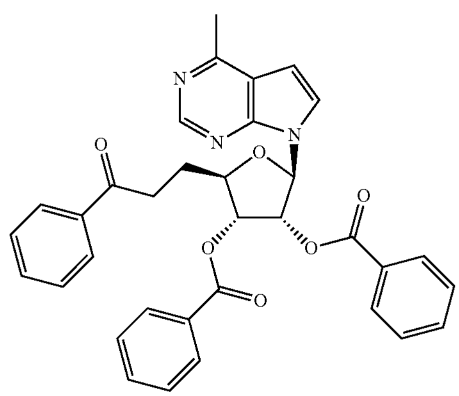 [SMILES: Cc1ncnc2c1ccn2[C@@H]1O[C@H](CCC(=O)c2ccccc2)[C@@H](OC(=O)c2ccccc2)[C@H]1OC(=O)c1ccccc1] | 4-Methyl-7-(2,3,5-tri-O-benzoyl-(β-D-ribofuranosyl)-7H-pyrrolo[2,3-d]pyrimidine |
| Intermediate 3 | 9 | 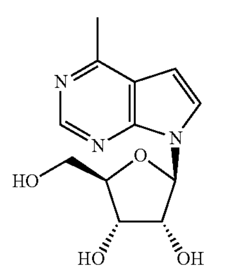 [SMILES: Cc1ncnc2c1ccn2[C@@H]1O[C@H](CO)[C@@H](O)[C@H]1O] | 4-Methyl-7-(β-D-ribofuranosyl)-7H-pyrrolo[2,3-d]pyrimidine |
| 33 | 5i | 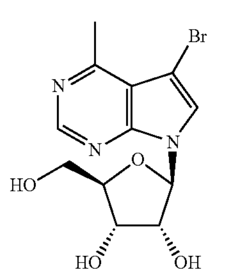 [SMILES: Cc1ncnc2c1c(Br)cn2[C@@H]1O[C@H](CO)[C@@H](O)[C@H]1O] | 5-Bromo-4-methyl-7-(β-D-ribofuranosyl)-7H-pyrrolo[2,3-d]pyrimidine |

-continued

| Example No | Compound number | Structure | Systematic Name |
|---|---|---|---|
| 34 | 5a | 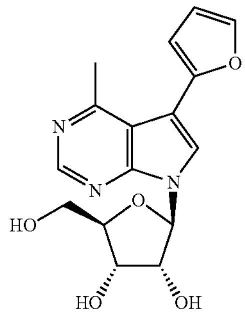 [SMILES: Cc1ncnc2c1c(-c1ccco1)cn2[C@@H]1O[C@H](CO)[C@@H](O)[C@H]1O] | 5-(Furan-2-yl)-4-methyl-7-(β-D-ribofuranosyl)-7H-pyrrolo[2,3-d]pyrimidine |
| 35 | 5b | 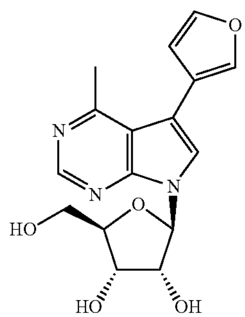 [SMILES: Cc1ncnc2c1c(-c1ccoc1)cn2[C@@H]1O[C@H](CO)[C@@H](O)[C@H]1O] | 5-(Furan-3-yl)-4-methyl-7-(β-D-ribofuranosyl)-7H-pyrrolo[2,3-d]pyrimidine |
| 36 | 5c | 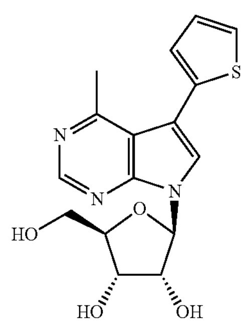 [SMILES: Cc1ncnc2c1c(-c1cccs1)cn2[C@@H]1O[C@H](CO)[C@@H](O)[C@H]1O] | 4-Methyl-7-(β-D-ribofuranosyl)-5-(thiophen-2-yl)-7H-pyrrolo[2,3-d]pyrimidine |
| 37 | 5d | 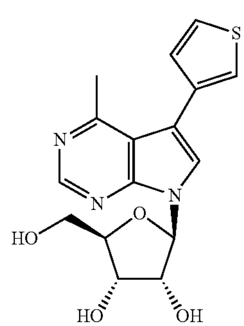 [SMILES: Cc1ncnc2c1c(-c1ccsc1)cn2[C@@H]1O[C@H](CO)[C@@H](O)[C@H]1O] | 4-Methyl-7-(β-D-ribofuranosyl)-5-(thiophen-3-yl)-7H-pyrrolo[2,3-d]pyrimidine |

| Example No | Compound number | Structure | Systematic Name |
|---|---|---|---|
| 38 | 5e | 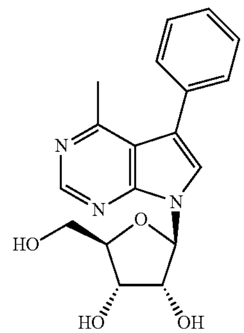 [SMILES: Cc1ncnc2c1c(-c1ccccc1)cn2[C@@H]1O[C@H](CO)[C@@H](O)[C@H]1O] | 4-Methyl-5-phenyl-7-(β-D-ribofuranosyl)-7H-pyrrolo[2,3-d]pyrimidine |
| 39 | 5f | 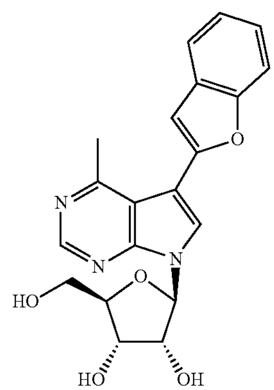 [SMILES: Cc1ncnc2c1c(-c1cc3ccccc3o1)cn2[C@@H]1O[C@H](CO)[C@@H](O)[C@H]1O] | 5-(Benzofuran-2-yl)-4-methyl-7-(β-D-ribofuranosyl)-7H-pyrrolo[2,3-d]pyrimidine |
| 40 | 5g | 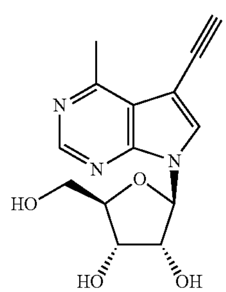 [SMILES: C#Cc1cn([C@@H]2O[C@H](CO)[C@@H](O)[C@H]2O)c2ncnc(C)c12] | 5-Ethynyl-4-methyl-7-(β-D-ribofuranosyl)-7H-pyrrolo[2,3-d]pyrimidine |

ABBREVIATIONS

Anal Combustion analysis
ATR Attenuated total reflectance
aq aqueous
bd broad doublet
bq broad quartet
BrdU 5-bromo-2'-deoxyuridine
BrU 5-bromouridine
bs road singlet
bt broad triplet
btd broad triplet of doublets
Bz benzoyl
C-18 C-18 reverse phase as stationary phase
calcd calculated
d doublet
dd doublet of doublets
ddd doublet of doublet of doublets
dm doublet of multiplets
DMF dimethylformamide
DMSO dimethylsulfoxide
dt doublet of triplets
ESI electrospray ionization
Et ethyl
FT Fourier transform
gem geminal
HPFC high performance flash chromatography
HR high resolution
i ipso
iPr isopropyl
IR infrared spectroscopy
m multiplet
m meta
Me methyl
MeCN acetonitrile
MeOH methanol
MeONa sodium methoxide
MeSNa sodium thiomethoxide
mp melting point
MS mass spectrometry
MTT 3-(4,5-dimethylthiazol-2-yl)-2,5-diphenyltetrazolium bromide v wave number
naphth naphthalenyl
NMR nuclear magnetic resonance
o ortho
p para
Ph phenyl
PPh$_3$ triphenylphosphine
q quartet
rt room temperature
s singlet
SiO$_2$ silicagel as stationary phase
t triplet
td triplet of doublets
TPPTS Tris(3-sulfophenyl)phosphine trisodium salt
XTT 2,3-bis-(2-methoxy-4-nitro-5-sulfophenyl)-2H-tetrazolium-5-carboxanilide.

General Experimental Part

NMR spectra were recorded on a 400 MHz ($^1$H at 400 MHz, $^{13}$C at 100.6 MHz), a 500 MHz ($^1$H at 500 MHz, $^{13}$C at 125.7 MHz), or a 600 MHz ($^1$H at 600 MHz, $^{13}$C at 150.9 MHz) spectrometer. Melting points were determined on a Kofler block and are uncorrected. Optical rotations were measured at 25° C., and $[\alpha]_D^{20}$ values are given in $10^{-1}$ deg cm$^2$ g$^{-1}$. High resolution mass spectra were measured using electrospray ionization. Reverse-phase high performance flash chromatography (HPFC) was performed on KP-C18-HS columns with Biotage SP1 system, and the sample was loaded as a solution in pure water or in water/DMSO (5:1) mixture. FT IR spectra were measured on Bruker Alpha spectrometer using ATR technique. The purity of all tested compounds was confirmed by HPLC analysis and was >95%.

EXAMPLE 1

5-(Furan-2-yl)-4-methoxy-7-((β-D-ribofuranosyl)-7H-pyrrolo[2,3-d]pyrimidine (1a)

An argon-purged mixture of 5-iodo-4-methoxy-7-(β-D-ribofuranosyl)-7H-pyrrolo[2,3-d]pyrimidine 1h (ref.: Seela, F.; Ming, X., *Tetrahedron* 2007, 63, 9850-9861) (794 mg, 1.95 mmol), furan-2-boronic acid (328 mg, 2.93 mmol), Na$_2$CO$_3$ (620 mg, 5.85 mmol), Pd(OAc)$_2$ (22 mg, 98 μmol) and TPPTS (136 mg, 0.24 mmol) in water/MeCN (2:1, 10 mL) was stirred at 100° C. for 3 h. After cooling, the mixture was neutralized using aq HCl (1 M), concentrated to dryness in vacuo and the residue purified by reverse phase HPFC (C-18, 0→100% MeOH in water). Re-purification by column chromatography (SiO$_2$, 2.5% MeOH in chloroform) furnished 1a (507 mg, 75%) as beige solid, which was crystallized from water/MeOH. Mp 155-157° C. $[\alpha]_D$ −78.2 (c 0.317, DMSO). $^1$H NMR (500 MHz, DMSO-d$_6$): 3.58 (dd, 1H, J$_{gem}$=11.9 Hz, J$_{5'a,4'}$=3.6 Hz, H-5'a); 3.65 (dd, 1H, J$_{gem}$=11.9 Hz, J$_{5'b,4'}$=3.7 Hz, H-5'b); 3.94 (bq, 1H, J$_{4',5'a}$=J$_{4',5'b}$=J$_{4',3'}$=3.5 Hz, H-4'); 4.11 (s, 3H, CH$_3$O); 4.13 (dd, 1H, J$_{3',2'}$=5.0 Hz, J$_{3',4'}$=3.2 Hz, H-3'); 4.44 (bt, 1H, J$_{2',1'}$=J$_{2',3'}$=5.6 Hz, H-2'); 5.14 (bs, 1H, OH-5'); 5.18 (bs, 1H, OH-3'); 5.38 (bs, 1H, OH-2'); 6.22 (d, 1H, J$_{1',2'}$=6.2 Hz, H-1'); 6.57 (dd, 1H, J$_{4,3}$=3.3 Hz, J$_{4,5}$=1.9 Hz, H-4-furyl); 6.93 (dd, 1H, J$_{3,4}$=3.3 Hz, J$_{3,5}$=0.9 Hz, H-3-furyl); 7.67 (dd, 1H, J$_{5,4}$=1.9 Hz, J$_{5,3}$=0.9 Hz, H-5-furyl); 7.98 (s, 1H, H-6); 8.47 (s, 1H, H-2). $^{13}$C NMR (125.7 MHz, DMSO-d$_6$): 54.05 (CH$_3$O); 61.65 (CH$_2$-5'); 70.79 (CH-3'); 74.41 (CH-2'); 85.51 (CH-4'); 87.08 (CH-1'); 101.50 (C-4a); 107.17 (C-5); 107.42 (CH-3-furyl); 111.92 (CH-4-furyl); 121.09 (CH-6); 141.81 (CH-5-furyl); 148.27 (CH-2-furyl); 151.52 (CH-2); 152.54 (C-7a); 162.76 (C-4). IR (ATR): ν 1590, 1563, 1120, 1080, 1063, 1012, 795, 744 cm$^{-1}$. MS (ESI) m/z 348 (M+H), 370 (M+Na). HRMS (ESI) for C$_{16}$H$_{18}$N$_3$O$_6$ [M+H] calcd: 348.11901. found: 348.11899. Anal. Calcd for C$_{16}$H$_{17}$N$_3$O$_6$·¼H$_2$O: C, 54.62; H, 5.01; N, 11.94. Found: C, 54.46; H, 4.92; N, 11.77.

EXAMPLE 2

5-(Furan-3-yl)-4-methoxy-7-(β-D-ribofuranosyl)-7H-pyrrolo[2,3-d]pyrimidine (1b)

Compound 1b was prepared as described for 1a in Example 1 from 1h (794 mg, 1.95 mmol) and furan-3-boronic acid as a beige solid (492 mg, 73%), which was crystallized from water/MeOH. Mp 190-192° C. $[\alpha]_D$ −66.8 (c 0.265, DMSO). $^1$H NMR (500 MHz, DMSO-d$_6$): 3.56 (dd, 1H, J$_{gem}$=11.9 Hz, J$_{5'a,4'}$=4.2 Hz, H-5'a); 3.67 (dd, 1H, J$_{gem}$=11.9 Hz, J$_{5'b,4'}$=4.2 Hz, H-5'b); 3.92 (btd, 1H, J$_{4',5'a}$=J$_{4',5'b}$=4.2 Hz, J$_{4',3'}$=3.4 Hz, H-4'); 4.10 (s, 3H, CH$_3$O); 4.13 (m, 1H, H-3'); 4.44 (m, 1H, H-2'); 5.10 (bs, 1H, OH-5'); 5.18 (bs, 1H, OH-3'); 5.39 (m, 1H, OH-2'); 6.19 (d, 1H, J$_{1',2'}$=6.2 Hz, H-1'); 6.93 (dd, 1H, J$_{4,5}$=1.9 Hz, J$_{4,2}$=0.9 Hz, H-4-furyl); 7.72 (t, 1H, J$_{5,4}$=J$_{5,2}$=1.7 Hz, H-5-furyl); 7.94 (s, 1H, H-6); 8.11 (bdd, 1H, J$_{2,5}$=1.5 Hz, J$_{2,4}$=0.9 Hz, H-2-furyl); 8.45 (s, 1H, H-2). $^{13}$C NMR (125.7 MHz, DMSO-d$_6$): 53.93 (CH$_3$O); 61.77 (CH$_2$-5'); 70.64 (CH-3'); 74.02 (CH-2'); 85.32 (CH-4'); 86.96 (CH-1'); 102.72 (C-4a); 107.24 (C-5); 110.25 (CH-4-furyl); 118.51 (C-3-furyl); 121.97 (CH-6); 140.05 (CH-2-furyl); 143.50 (CH-5-furyl); 151.18 (CH-2); 152.71 (C-7a); 162.74 (C-4). IR (ATR): ν 1591, 1566, 1160, 1063, 1003, 897, 775, 614, 592 cm$^{-1}$. MS (ESI) m/z 348 (M+H), 370 (M+Na). HRMS (ESI) for C$_{16}$H$_{18}$N$_3$O$_6$ [M+H] calcd: 348.11901. found: 348.11897. Anal. Calcd for C$_{16}$H$_{17}$N$_3$O$_6$: C, 55.33; H, 4.93; N, 12.10. Found: C, 55.37; H, 4.85; N, 11.89.

EXAMPLE 3

4-Methoxy-7-(β-D-ribofuranosyl)-5-(thiophen-2-yl)-7H-pyrrolo[2,3-d]pyrimidine (1c)

Compound 1c was prepared as described for 1a in Example 1 from 1h (797 mg, 1.96 mmol) and thiophene-2-boronic acid as a greyish solid (615 mg, 86%), which was crystallized from water/MeOH. Mp 140-143° C. $[\alpha]_D$ −67.8 (c 0.283, DMSO). $^1$H NMR (500 MHz, DMSO-d$_6$): 3.57 (ddd, 1H, J$_{gem}$=12.0 Hz, J$_{5'a,OH}$=5.8 Hz, J$_{5'a,4'}$=3.7 Hz, H-5'a); 3.67 (ddd, 1H, J$_{gem}$=12.0 Hz, J$_{5'b,OH}$=5.2 Hz, J$_{5'b,4'}$=3.8 Hz, H-5'b); 3.93 (bq, 1H, J$_{4',5'a}$=J$_{4',5'b}$=J$_{4',3'}$=3.6 Hz, H-4'); 4.07 (s, 3H, CH$_3$O); 4.13 (td, 1H, J$_{3',2'}$=J$_{3',OH}$=5.0 Hz, J$_{3',4'}$=3.3 Hz, H-3'); 4.44 (td, 1H, J$_{2',1'}$=J$_{2',OH}$=6.2 Hz, J$_{2',3'}$=5.1 Hz, H-2'); 5.14 (t, 1H, J$_{OH,5'a}$=J$_{OH,5'b}$=5.5 Hz, OH-5'); 5.18 (d, 1H, J$_{OH,3'}$=4.7 Hz, OH-3'); 5.40 (d, 1H, J$_{OH,2'}$=6.4 Hz, OH-2'); 6.21 (d, 1H, J$_{1',2'}$=6.1 Hz, H-1'); 7.11 (dd, 1H, J$_{4,5}$=5.1 Hz, J$_{4,3}$=3.7 Hz, H-4-thienyl); 7.45 (dd, 1H, J$_{3,4}$=3.7 Hz, J$_{3,5}$=1.1 Hz, H-3-thienyl); 7.46 (dd, 1H, J$_{5,4}$=5.1 Hz, J$_{5,3}$=1.1 Hz, H-5-thienyl); 7.96 (s, 1H, H-6); 8.48 (s, 1H, H-2). $^{13}$C NMR (125.7 MHz, DMSO-d$_6$): 53.88 (CH$_3$O); 61.59 (CH$_2$-5'); 70.64 (CH-3'); 74.28 (CH-2'); 85.45 (CH-4'); 87.13 (CH-1'); 102.59 (C-4a); 109.89 (C-5); 122.52 (CH-6); 124.77 (CH-5-thienyl); 125.99 (CH-3-thienyl); 127.88 (CH-4-thienyl); 135.63 (C-2-thienyl); 151.32 (CH-2); 152.50 (C-7a); 162.81 (C-4). IR (ATR): ν 1577, 1553, 1326, 1302, 1120, 1062, 1051, 1010, 786, 683 cm$^{-1}$. MS (ESI) m/z 364 (M+H), 386 (M+Na). HRMS (ESI) for C$_{16}$H$_{18}$N$_3$O$_5$S [M+H] calcd: 364.0962. found: 364.09608.

Anal. Calcd for $C_{16}H_{17}N_3O_5S.\frac{3}{4}H_2O$: C, 50.99; H, 4.95; N, 11.15. Found: C, 50.89; H, 4.85; N, 10.95.

EXAMPLE 4

4-Methoxy-7-(β-D-ribofuranosyl)-5-(thiophen-3-yl)-7H-pyrrolo[2,3-d]pyrimidine (1d)

Compound 1d was prepared as described for 1a in Example 1 from 1h (794 mg, 1.95 mmol) and thiophene-3-boronic acid as a white solid (561 mg, 79%), which was crystallized from water/MeOH. Mp 169-171° C. $[\alpha]_D$ −62.6 (c 0.254, DMSO). $^1$H NMR (500 MHz, DMSO-d$_6$): 3.57 (ddd, 1H, $J_{gem}$=11.9 Hz, $J_{5'a,OH}$=5.8 Hz, $J_{5'a,4'}$=4.1 Hz, H-5'a); 3.67 (ddd, 1H, $J_{gem}$=11.9 Hz, $J_{5'b,OH}$=5.3 Hz, $J_{5'b,4'}$=4.1 Hz, H-5'b); 3.93 (bq, 1H, $J_{4'5'a}$=$J_{4',5'b}$=$J_{4',3'}$=3.8 Hz, H-4'); 4.09 (s, 3H, CH$_3$O); 4.14 (td, 1H, $J_{3',2'}$=$J_{3',OH}$=5.0 Hz, $J_{3',4'}$=3.4 Hz, H-3'); 4.45 (btd, 1H, $J_{2',1'}$=$J_{2',OH}$=6.2 Hz, $J_{2',3'}$=5.2 Hz, H-2'); 5.11 (t, 1H, $J_{OH,5'a}$=$J_{OH,5'b}$=5.6 Hz, OH-5'); 5.18 (d, 1H, $J_{OH,3'}$=4.9 Hz, OH-3'); 5.39 (d, 1H, $J_{OH,2'}$=6.4 Hz, OH-2'); 6.21 (d, 1H, $J_{1',2'}$=6.1 Hz, H-1'); 7.52 (dd, 1H, $J_{4,5}$=5.0 Hz, $J_{4,2}$=1.3 Hz, H-4-thienyl); 7.59 (dd, 1H, $J_{5,4}$=5.0 Hz, $J_{5,2}$=3.0 Hz, H-5-thienyl); 7.84 (dd, 1H, $J_{2,5}$=3.0 Hz, $J_{2,4}$=1.3 Hz, H-2-thienyl); 7.99 (s, 1H, H-6); 8.46 (s, 1H, H-2). $^{13}$C NMR (125.7 MHz, DMSO-d$_6$): 53.93 (CH$_3$O); 61.72 (CH$_2$-5'); 70.64 (CH-3'); 74.13 (CH-2'); 85.35 (CH-4'); 87.06 (CH-1'); 102.80 (C-4a); 111.67 (C-5); 121.53 (CH-2-thienyl); 122.65 (CH-6); 125.96 (CH-5-thienyl); 128.09 (CH-4-thienyl); 134.12 (C-3-thienyl); 151.04 (CH-2); 152.62 (C-7a); 162.81 (C-4). IR (ATR): v 1579, 1556, 1476, 1328, 1303, 1123, 1062, 1051, 1020, 775 cm$^{-1}$. MS (ESI) m/z 364 (M+H), 386 (M+Na). HRMS (ESI) for $C_{16}H_{18}N_3O_5S$ [M+H] calcd: 364.0962. found: 364.09609. Anal. Calcd for $C_{16}H_{17}N_3O_5S.H_2O$: C, 50.39; H, 5.02; N, 11.02. Found: C, 50.54; H, 4.97; N, 10.82.

EXAMPLE 5

4-Methoxy-5-phenyl-7-(β-D-ribofuranosyl)-7H-pyrrolo[2,3-d]pyrimidine (1e)

Compound 1e was prepared as described for 1a in Example 1 from 1h (794 mg, 1.95 mmol) and phenylboronic acid as a white solid (573 mg, 82%), which was crystallized from water. Mp 117-120° C. $[\alpha]_D$ −63.2 (c 0.275, DMSO). $^1$H NMR (500 MHz, DMSO-d$_6$): 3.56 (ddd, 1H, $J_{gem}$=12.0 Hz, $J_{5'a,OH}$=5.8 Hz, $J_{5'a,4'}$=4.0 Hz, H-5'a); 3.66 (ddd, 1H, $J_{gem}$=12.0 Hz, $J_{5'b,OH}$=5.3 Hz, $J_{5'b,4'}$=4.0 Hz, H-5b); 3.93 (btd, 1H, $J_{4',5'a}$=$J_{4',5'b}$=4.0 Hz, $J_{4',3'}$=3.4 Hz, H-4'); 4.02 (s, 3H, CH$_3$O); 4.14 (btd, 1H, $J_{3',2'}$=$J_{3',OH}$=5.0 Hz, $J_{3',4'}$=3.4 Hz, H-3'); 4.47 (td, 1H, =$J_{2',OH}$=6.2 Hz, $J_{2',3'}$=5.1 Hz, H-2'); 5.11 (t, 1H, $J_{OH,5'a}$=$J_{OH,5'b}$=5.5 Hz, OH-5'); 5.18 (d, 1H, $J_{OH,3'}$=4.9 Hz, OH-3'); 5.40 (d, 1H, $J_{OH,2'}$=6.4 Hz, OH-2'); 6.24 (d, 1H, $J_{1',2'}$=6.1 Hz, H-1'); 7.30 (m, 1H, H-p-Ph); 7.42 (m, 2H, H-m-Ph); 7.66 (m, 2H, H-o-Ph); 7.88 (s, 1H, H-6); 8.48 (s, 1H, H-2). $^{13}$C NMR (125.7 MHz, DMSO-d$_6$): 53.86 (CH$_3$O); 61.71 (CH$_2$-5'); 70.72 (CH-3'); 74.24 (CH-2'); 85.40 (CH-4'); 87.14 (CH-1'); 103.01 (C-4a); 116.62 (C-5); 122.93 (CH-6); 126.68 (CH-p-Ph); 128.38 (CH-m-Ph); 128.68 (CH-o-Ph); 133.95 (C-i-Ph); 150.96 (CH-2); 152.79 (C-7a); 162.90 (C-4). IR (ATR): v 1590, 1567, 1484, 1364, 1346, 1305, 1173, 1099, 1072, 1044, 761, 698 cm$^{-1}$. MS (ESI) m/z 358 (M+H), 380 (M+Na). HRMS (ESI) for $C_{18}H_{20}N_3O_5$ [M+H] calcd: 358.1397. found: 358.1394 and for $C_{18}H_{19}N_3O_5Na$ [M+Na] calcd: 380.12169. found: 380.12168. Anal. Calcd for $C_{18}H_{19}N_3O_5.H_2O$: C, 57.59; H, 5.64; N, 11.19. Found: C, 57.55; H, 5.56; N, 10.97.

EXAMPLE 6

5-(Benzofuran-2-yl)-4-methoxy-7-(β-D-ribofuranosyl)-7H-pyrrolo[2,3-d]pyrimidine (1f)

An argon-purged mixture of 1h (794 mg, 1.95 mmol), benzofuran-2-boronic acid (475 mg, 2.93 mmol), Na$_2$CO$_3$ (620 mg, 5.85 mmol), Pd(OAc)$_2$ (22 mg, 97.5 μmol) and TPPTS (136 mg, 0.24 mmol) in water/MeCN (2:1, 10 mL) was stirred at 100° C. for 3 h. After cooling, the solidified mixture was suspended by addition of water (40 mL) and shaking. The pH of the mixture was adjusted to 5 using aq HCl (1 M), formed precipitate was filtered off and washed with water. After drying, the precipitate was loaded on silica by co-evaporation from chloroform/MeOH solution and chromatographed (SiO$_2$, 2.5% MeOH in chloroform) to give 1f (659 mg, 85%) as a white solid, which was crystallized from MeOH to give white needles. Mp 250-251° C. $[\alpha]_D$ −88.9 (c 0.262, DMSO). $^1$H NMR (500 MHz, DMSO-d$_6$): 3.61 (ddd, 1H, $J_{gem}$=12.0 Hz, $J_{5'a,OH}$=5.7 Hz, $J_{5'a,4'}$=3.8 Hz, H-5'a); 3.69 (ddd, 1H, $J_{gem}$=12.0 Hz, $J_{5'b,OH}$=5.2 Hz, $J_{5'b,4'}$=3.7 Hz, H-5'b); 3.97 (btd, 1H, $J_{4',5'a}$=$J_{4',5'b}$=3.7 Hz, $J_{4',3'}$=3.3 Hz, H-4'); 4.16 (td, 1H, $J_{3',2'}$=$J_{3',OH}$=5.1 Hz, $J_{3',4'}$=3.2 Hz, H-3'); 4.20 (s, 3H, CH$_3$O); 4.50 (td, 1H, $J_{2',1'}$=$J_{2'}$, OH=6.3 Hz, $J_{2',3'}$=5.1 Hz, H-2'); 5.18 (t, 1H, $J_{OH,5'a}$=$J_{OH,5'b}$=5.4 Hz, OH-5'); 5.22 (d, 1H, $J_{OH,3'}$=4.8 Hz, OH-3'); 5.43 (d, 1H, $J_{OH,2'}$=6.4 Hz, OH-2'); 6.26 (d, 1H, $J_{1',2'}$=6.3 Hz, H-1'); 7.24 (btd, 1H, $J_{5,6}$=$J_{5,4}$=7.4 Hz, $J_{5,7}$=1.1 Hz, H-5-benzofuryl); 7.29 (bddd, 1H, $J_{6,7}$=8.1 Hz, $J_{6,5}$=7.3 Hz, $J_{6,4}$=1.5 Hz, H-6-benzofuryl); 7.44 (d, 1H, $J_{3,7}$=1.0 Hz, H-3-benzofuryl); 7.56 (dq, 1H, $J_{7,6}$=8.1 Hz, $J_{7,5}$=$J_{7,4}$=$J_{7,3}$=1.0 Hz, H-7-benzofuryl); 7.66 (ddd, 1H, $J_{4,5}$=7.6 Hz, $J_{4,6}$=1.4 Hz, $J_{4,7}$=0.7 Hz, H-4-benzofuryl); 8.25 (s, 1H, H-6); 8.54 (s, 1H, H-2). $^{13}$C NMR (125.7 MHz, DMSO-d$_6$): 54.28 (CH$_3$O); 61.64 (CH$_2$-5'); 70.74 (CH-3'); 74.38 (CH-2'); 85.64 (CH-4'); 87.13 (CH-1'); 101.85 (C-4a); 103.44 (CH-3-benzofuryl); 106.54 (C-5); 110.75 (CH-7-benzofuryl); 121.11 (CH-4-benzofuryl); 123.14 and 123.22 (CH-6,CH-5-benzofuryl); 124.31 (CH-6-benzofuryl); 129.44 (C-3a-benzofuryl); 150.67 (C-2-benzofuryl); 151.89 (CH-2); 153.00 (C-7a); 153.83 (C-7a-benzofuryl); 162.81 (C-4). IR (ATR): v 1593, 1564, 1476, 1383,1330, 1260, 1127, 1099, 1060, 1033, 991, 939, 797, 739, 672 cm$^{-1}$. MS (ESI) m/z 398 (M+H), 420 (M+Na). HRMS (ESI) for $C_{20}H_{19}N_3O_6Na$ [M+Na] calcd: 420.1166. found: 420.1165. Anal. Calcd for $C_{24}H_{19}N_3O_6.0.35H_2O$: C, 59.51; H, 4.92; N, 10.41. Found: C, 59.64; H, 4.72; N, 10.19.

EXAMPLE 7

5-Ethynyl-4-methoxy-7-(β-D-ribofuranosyl)-7H-pyrrolo[2,3-d]pyrimidine (1g)

An argon-purged mixture of 1h (407 mg, 1 mmol), PdCl$_2$(PPh$_3$)$_2$ (35 mg, 0.05 mmol), CuI (19 mg, 0.1 mmol), trimethylsilylacetylene (1.4 mL, 10 mmol) and triethylamine (0.5 mL) was stirred in DMF (2 mL) at rt for 16 h. The volatiles were removed in vacuo and the residue was several times co-evaporated with EtOH/toluene and loaded on silica by co-evaporation. Column chromatography (SiO$_2$, 0→1.5% MeOH in CHCl$_3$) afforded trimethylsilylethynyl derivative contaminated by triethylammonium iodide. This material was directly deprotected by treatment with K$_2$CO$_3$ (207 mg, 1.5 mmol) in MeOH (5 mL) at rt for 5 h, followed by co-evaporation with silica and final column chromatography (SiO$_2$, 2.5% MeOH in CHCl$_3$) afforded 2g (268 mg, 88% in two steps), which was crystallized from MeOH. Mp 205-207° C. [α]$_D$ −78.4 (c 0.333, DMSO). $^1$H NMR (500 MHz, DMSO-d$_6$): 3.56 (ddd, 1H, J$_{gem}$=11.9 Hz, J$_{5'a,OH}$=5.7 Hz, J$_{5'a,4}$=3.7 Hz, H-5'a); 3.65 (ddd, 1H, J$_{gem}$=11.9 Hz, J$_{5'b,OH}$=5.3 Hz, J$_{5'b,4}$=3.9 Hz, H-5'b); 3.92 (td, 1H, J$_{4',5'a}$=J$_{4',5'b}$=3.8 Hz, J$_{4',3}$=3.5 Hz, H-4'); 4.06 (s, 3H, CH$_3$O); 4.10 (td, 1H, J$_{3',2'}$=J$_{3',OH}$=5.0 Hz, J$_{3',4}$=3.4 Hz, H-3'); 4.11 (d, 1H, J$_{CH,6}$=0.4 Hz, C≡CH); 4.38 (td, 1H, J$_{2',1'}$=J$_{2',OH}$=6.2 Hz, J$_{2',3}$=5.0 Hz, H-2'); 5.12 (t, 1H, J$_{OH,5'a}$=J$_{OH,5'b}$=5.5 Hz, OH-5'); 5.18 (d, 1H, J$_{OH,3}$=4.9 Hz, OH-3'); 5.41 (d, 1H, J$_{OH,2}$=6.3 Hz, OH-2'); 6.14 (d, 1H, J$_{1',2}$=6.0 Hz, H-1'); 8.05 (s, 1H, H-6); 8.47 (s, 1H, H-2). $^{13}$C NMR (125.7 MHz, DMSO-d$_6$): 54.04 (CH$_3$O); 61.55 (CH$_2$-5'); 70.63 (CH-3'); 74.45 (CH-2'); 77.17 (C≡CH); 81.80 (C≡CH); 85.56 (CH-4'); 87.31 (CH-1'); 94.82 (C-5); 105.16 (C-4a); 130.01 (CH-6); 151.43 (C-7a); 151.93 (CH-2); 162.95 (C-4). IR (ATR): ν 1596, 1574, 1061, 1005, 653, 604, 535 cm$^{-1}$. MS (ESI) m/z 306 (M+H), 328 (M+Na). HRMS (ESI) for C$_{14}$H$_{15}$N$_3$O$_5$Na [M+Na] calcd: 328.0904. found: 328.0892. Anal. Calcd for C$_{14}$H$_{15}$N$_3$O$_5$·¼H$_2$O: C, 54.28; H, 5.04; N, 13.56. Found: C, 54.40; H, 4.92; N, 13.45.

EXAMPLE 8

5-Iodo-4-methylsulfanyl-7-(β-D-ribofuranosyl)-7H-pyrrolo[2,3-d]pyrimidine (2h)

A mixture of 4-chloro-5-iodo-7-(2,3,5-tri-O-benzoyl-(β-D-ribofuranosyl)-7H-pyrrolo[2,3-d]pyrimidine 6 (ref.: Seela, F.; Ming, X., *Tetrahedron* 2007, 63, 9850-9861) (5.37 g, 7.42 mmol) and sodium thiomethoxide (1.1 g, 15.7 mmol) in EtOH (150 mL) was stirred at rt for 4 h. The volatiles were removed in vacuo, the residue was co-evaporated several times with water and crystallized from water to furnish 2h (2.94 g, 94%) as white solid. Mp 217-219° C. [α]$^{20}_D$ −69.8 (c 0.242, DMSO). $^1$H NMR (500 MHz, DMSO-d$_6$): 2.63 (s, 3H, CH$_3$S); 3.55 (ddd, 1H, J$_{gem}$=12.0 Hz, J$_{5'a,OH}$=5.5 Hz, J$_{5'a,4}$=4.0 Hz, H-5'a); 3.63 (ddd, 1H, J$_{gem}$=12.0 Hz, J$_{5'b,OH}$=5.2 Hz, J$_{5'b,4}$=4.0 Hz, H-5'b); 3.91 (bq, 1H, J$_{4',5'a}$=J$_{4',5'b}$=3.6 Hz, H-4'); 4.09 (m, 1H, H-3'); 4.36 (m, 1H, H-2'); 5.09 (bt, 1H, J$_{OH,5'a}$=J$_{OH,5'b}$=5.4 Hz, OH-5'); 5.18 (bd, 1H, J$_{OH,3}$=3.9 Hz, OH-3'); 5.40 (bs, 1H, OH-2'); 6.15 (d, 1H, J$_{1',2}$=6.2 Hz, H-1'); 7.99 (s, 1H, H-6); 8.62 (s, 1H, H-2). $^{13}$C NMR (125.7 MHz, DMSO-d$_6$): 12.13 (CH$_3$S); 53.17 (C-5); 61.56 (CH$_2$-5'); 70.62 (CH-3'); 74.38 (CH-2'); 85.54 (CH-4'); 86.77 (CH-1'); 117.20 (C-4a); 130.87 (CH-6); 148.74 (C-7a); 150.86 (CH-2); 161.82 (C-4). IR (ATR): ν 3386, 3132, 1556, 1449, 1220, 1113, 1066, 954, 492 cm$^{-1}$. MS (ESI) m/z 424 (M+H), 446 (M+Na). HRMS (ESI) for C$_{12}$H$_{15}$IN$_3$O$_4$S [M+H] calcd: 423.98279. found: 423.98216. Anal. Calcd for C$_{12}$H$_{14}$IN$_3$O$_4$S·¾H$_2$O: C, 33.00; H, 3.58; N, 9.62. Found: C, 33.28; H, 3.36; N, 9.40.

EXAMPLE 9

5-(Furan-2-yl)-4-methylsulfanyl-7-(β-D-ribofuranosyl)-7H-pyrrolo[2,3-d]pyrimidine (2a)

An argon-purged mixture of 2h (313 mg, 0.74 mmol), furan-2-boronic acid (124 mg, 1.11 mmol), Na$_2$CO$_3$ (235 mg, 2.22 mmol), Pd(OAc)$_2$ (8 mg, 36 μmol) and TPPTS (53 mg, 0.093 mmol) in water/MeCN (2:1, 4 mL) was stirred at 100° C. for 1 h. After cooling the mixture was neutralized using aq HCl (1 M) and concentrated by evaporation. The residue was co-evaporated with silica and purified by column chromatography (SiO$_2$, 1→3% MeOH in CHCl$_3$). Re-purification by reverse-phase HPFC (C-18, 0→100% MeOH in water) and crystallization from water/MeOH afforded 2a (123 mg, 46%) as a yellowish solid. Mp 150-152° C. [α]$^{20}_D$ −70.5 (c 0.237, DMSO). $^1$H NMR (500 MHz, DMSO-d$_6$): 2.59 (s, 3H, CH$_3$S); 3.56 (ddd, 1H, J$_{gem}$=12.0 Hz, J$_{5'a,OH}$=5.6 Hz, J$_{5'a,4}$=3.8 Hz, H-5'a); 3.65 (ddd, 1H, J$_{gem}$=12.0 Hz, J$_{5'b,OH}$=5.3 Hz, J$_{5'b,4}$=3.9 Hz, H-5'b); 3.93 (bq, 1H, J$_{4',5'a}$=J$_{4',5'b}$=J$_{4',3}$=3.6 Hz, H-4'); 4.12 (td, 1H, J$_{3',2}$=J$_{3',OH}$=5.0 Hz, J$_{3',4}$=3.3 Hz, H-3'); 4.42 (td, 1H, J$_{2'1'}$=J$_{2',OH}$=6.2 Hz, J$_{2',3}$=5.1 Hz, H-2'); 5.10 (t, 1H, J$_{OH,5'a}$=J$_{OH,5'b}$=5.4 Hz, OH-5'); 5.19 (d, 1H, J$_{OH,3}$=4.8 Hz, OH-3'); 5.42 (d, 1H, J$_{OH,2}$=6.3 Hz, OH-2'); 6.23 (d, 1H, J$_{1',2}$=6.1 Hz, H-1'); 6.60 (dd, 1H, J$_{4,3}$=3.3 Hz, J$_{4,5}$=1.9 Hz, H-4-furyl); 6.71 (dd, 1H, J$_{3,4}$=3.3 Hz, J$_{3,5}$=0.9 Hz, H-3-furyl); 7.78 (dd, 1H, J$_{5,4}$=1.9 Hz, J$_{5,3}$=0.9 Hz, H-5-furyl); 8.01 (s, 1H, H-6); 8.68 (s, 1H, H-2). $^{13}$C NMR (125.7 MHz, DMSO-d$_6$): 12.21 (CH$_3$S); 61.58 (CH$_2$-5'); 70.68 (CH-3'); 74.42 (CH-2'); 85.54 (CH-4'); 86.92 (CH-1'); 106.61 (C-5); 109.18 (CH-3-furyl); 111.68 (CH-4-furyl); 113.63 (C-4a); 125.13 (CH-6); 142.90 (CH-5-furyl); 146.82 (C-2-furyl); 148.92 (C-7a); 150.91 (CH-2); 161.69 (C-4). IR (ATR): ν 3166, 2937, 2903, 1547, 1446, 1062, 1029, 976, 594 cm$^{-1}$. MS (ESI) m/z 364 (M+H), 386 (M+Na). HRMS (ESI) for C$_{16}$H$_{18}$N$_3$O$_5$S [M+H] calcd: 364.09672. found: 364.09609.

EXAMPLE 10

5-(Furan-3-yl)-4-methylsulfanyl-7-(β-D-ribofuranosyl)-7H-pyrrolo[2,3-d]pyrimidine (2b)

Compound 2b was prepared as described for 2a in Example 9 from 2h (313 mg, 0.74 mmol) and furan-3-boronic acid. After column chromatography (SiO$_2$), the product was re-purified by crystallization from water/MeOH to afford 2b (242 mg, 90%) as a white solid. Mp 121-124° C. [α]$^{20}_D$ −57.3 (c 0.218, DMSO). $^1$H NMR (500 MHz, DMSO-d$_6$): 2.58 (s, 3H, CH$_3$); 3.55 (ddd, 1H, J$_{gem}$=11.9 Hz, J$_{5'a,OH}$=5.7 Hz, J$_{5'a,4}$=3.9 Hz, H-5'a); 3.64 (ddd, 1H, J$_{gem}$=11.9 Hz, J$_{5'b,OH}$=5.4 Hz, J$_{5'b,4}$=3.9 Hz, H-5'b); 3.92 (bq, 1H, J$_{4',5'a}$=J$_{4',5'b}$=J$_{4',3}$=3.7 Hz, H-4'); 4.12 (td, 1H, J$_{3',2}$=J$_{3',OH}$=5.0 Hz, J$_{3',4}$=3.3 Hz, H-3'); 4.42 (td, 1H, J$_{2'1'}$=J$_{2',OH}$=6.3 Hz, J$_{2',3}$=5.1 Hz, H-2'); 5.07 (t, 1H, J$_{OH,5'a}$=J$_{OH,5'b}$=5.5 Hz, OH-5'); 5.18 (d, 1H, J$_{OH,3}$=4.9 Hz, OH-3'); 5.39 (d, 1H, J$_{OH,2}$=6.4 Hz, OH-2'); 6.22 (d, 1H, J$_{1',2}$=6.2 Hz, H-1'); 6.73 (dd, 1H, J$_{4,5}$=1.8 Hz, J$_{4,2}$=0.9 Hz, H-4-furyl); 7.77 (t, 1H, J$_{5,4}$=J$_{5,2}$=1.7 Hz, H-5-furyl); 7.80 (s, 1H, H-6); 7.87 (dd, 1H, J$_{2,5}$=1.6 Hz, J$_{2,4}$=0.9 Hz, H-2-furyl); 8.65 (s, 1H, H-2). $^{13}$C NMR (125.7 MHz, DMSO-d$_6$): 12.05 (CH$_3$S); 61.68 (CH$_2$-5'); 70.70 (CH-3'); 74.27 (CH-2'); 85.43 (CH-4'); 86.79 (CH-1'); 107.03 (C-5); 113.13 (CH-4-furyl); 114.57 (C-4a); 117.72 (C-3-furyl); 124.47 (CH-6); 140.97 (CH-2-furyl); 143.27 (CH-5-furyl); 148.99 (C-7a); 150.61 (CH-2); 161.37 (C-4). IR (ATR): ν 3347, 3156, 2960, 2861, 1555, 1459, 1133, 1063, 784 cm$^{-1}$. MS (ESI) m/z 364 (M+H), 386 (M+Na). HRMS (ESI) for C$_{16}$H$_{18}$N$_3$O$_5$S [M+H] calcd: 364.09672. found: 364.09611.

EXAMPLE 11

4-Methylsulfanyl-7-(β-D-ribofuranosyl)-5-(thiophen-2-yl)-7H-pyrrolo[2,3-d]pyrimidine (2c)

Compound 2c was prepared as described for 2a in Example 9 from 2h (180 mg, 0.43 mmol) and thiophene-2-boronic acid. The product after purification by chromatographies (SiO$_2$, then C-18) was re-purified by crystallization from water/MeOH to give 2c (109 mg, 67%) as a white powder. Mp 164-167° C. $[\alpha]^{20}_D$ −57.2 (c 0.180, DMSO). $^1$H NMR (500 MHz, DMSO-d$_6$): 2.55 (s, 3H, CH$_3$); 3.55 (ddd, 1H, $J_{gem}$=12.0 Hz, $J_{5'a,OH}$=5.6 Hz, $J_{5'a,4'}$=3.8 Hz, H-5'a); 3.64 (ddd, 1H, $J_{gem}$=12.0 Hz, $J_{5'b,OH}$=5.3 Hz, $J_{5'b,4'}$=3.9 Hz, H-5'b); 3.93 (bq, 1H, $J_{4',5'a}$=$J_{4',5'b}$=$J_{4',3'}$=3.5 Hz, H-4'); 4.11 (td, 1H, $J_{3',2'}$=$J_{3',OH}$=5.0 Hz, $J_{3',4'}$=3.3 Hz, H-3'); 4.43 (td, 1H, $J_{2',1'}$=$J_{2',OH}$=6.3 Hz, $J_{2',3'}$=5.1 Hz, H-2'); 5.09 (t, 1H, $J_{OH,5'a}$=$J_{OH,5'b}$=5.4 Hz, OH-5'); 5.18 (d, 1H, $J_{OH,3'}$=4.8 Hz, OH-3'); 5.41 (d, 1H, $J_{OH,2'}$=6.4 Hz, OH-2'); 6.23 (d, 1H, $J_{1',2'}$=6.2 Hz, H-1'); 7.16 (dd, 1H, $J_{4,5}$=5.2 Hz, $J_{4,3}$=3.5 Hz, H-4-thienyl); 7.22 (dd, 1H, $J_{3,4}$=3.5 Hz, $J_{3,5}$=1.2 Hz, H-3-thienyl); 7.59 (dd, 1H, $J_{5,4}$=5.2 Hz, $J_{5,3}$=1.2 Hz, H-5-thienyl); 7.91 (s, 1H, H-6); 8.67 (s, 1H, H-2). $^{13}$C NMR (125.7 MHz, DMSO-d$_6$): 12.05 (CH$_3$S); 61.58 (CH$_2$-5'); 70.68 (CH-3'); 74.36 (CH-2'); 85.53 (CH-4'); 86.87 (CH-1'); 108.95 (C-5); 114.51 (C-4a); 125.60 (CH-6); 126.52 (C-5-thienyl); 127.64 (CH-4-thienyl); 128.84 (CH-3-thienyl); 133.93 (C-2-thienyl); 148.75 (C-7a); 150.81 (CH-2); 161.61 (C-4). IR (ATR): v 3399, 2931, 1540, 1332, 1100, 1036, 1024, 711 cm$^1$. MS (ESI) m/z 380 (M+H), 402 (M+Na). HRMS (ESI) for C$_{16}$H$_{18}$N$_3$O$_4$S$_2$ [M+H] calcd: 380.07387. found: 380.07324.

EXAMPLE 12

4-Methylsulfanyl-7-(β-D-ribofuranosyl)-5-(thiophen-3-yl)-7H-pyrrolo[2,3-d]pyrimidine (2d)

Compound 2d was prepared as described for 2a in Example 9 from 2h (313 mg, 0.74 mmol) and thiophene-3-boronic acid. Purification by column chromatography (SiO$_2$) provided pure 2d (228 mg, 81%) as a white powder, which was crystallized from water/MeOH. Mp 192-193° C. $[\alpha]^{20}_D$ −54.7 (c 0.225, DMSO). $^1$H NMR (500 MHz, DMSO-d$_6$): 2.56 (s, 3H, CH$_3$S); 3.56 (ddd, 1H, $J_{gem}$=12.0 Hz, $J_{5'a,OH}$=5.7 Hz, $J_{5'a,4'}$=4.0 Hz, H-5'a); 3.64 (ddd, 1H, $J_{gem}$=12.0 Hz, $J_{5'b,OH}$=5.4 Hz, $J_{5'b,4'}$=4.0 Hz, H-5'b); 3.92 (bq, 1H, $J_{4',5'a}$=$J_{4',5'b}$=$J_{4',3'}$=3.7 Hz, H-4'); 4.12 (td, 1H, $J_{3',2'}$=$J_{3',OH}$=5.0 Hz, $J_{3',4'}$=3.3 Hz, H-3'); 4.43 (td, 1H, $J_{2',1'}$=$J_{2',OH}$=6.3 Hz, $J_{2',3'}$=5.1 Hz, H-2'); 5.07 (t, 1H, $J_{OH,5'a}$=$J_{OH,5'b}$=5.5 Hz, OH-5'); 5.18 (d, 1H, $J_{OH,3'}$=4.9 Hz, OH-3'); 5.39 (d, 1H, $J_{OH,2'}$=6.4 Hz, OH-2'); 6.23 (d, 1H, $J_{1',2'}$=6.2 Hz, H-1'); 7.29 (dd, 1H, $J_{4,5}$=4.9 Hz, $J_{4,2}$=1.3 Hz, H-4-thienyl); 7.57 (dd, 1H, $J_{2,5}$=3.0 Hz, $J_{2,4}$=1.3 Hz, H-2-thienyl); 7.63 (dd, 1H, $J_{5,4}$=4.9 Hz, $J_{5,2}$=3.0 Hz, H-5-thienyl); 7.82 (s, 1H, H-6); 8.66 (s, 1H, H-2). $^{13}$C NMR (125.7 MHz, DMSO-d$_6$): 12.10 (CH$_3$S); 61.66 (CH$_2$-5'); 70.71 (CH-3'); 74.29 (CH-2'); 85.43 (CH-4'); 86.81 (CH-1'); 111.64 (C-5); 114.44 (C-4a); 124.08 (CH-2-thienyl); 124.47 (CH-6); 124.47 (CH-5-thienyl); 125.73 (CH-4-thienyl); 133.59 (C-3-thienyl); 148.79 (C-7a); 150.55 (CH-2); 161.37 (C-4). IR (ATR): v 3320, 3093, 2932, 1542, 1113, 1031, 988, 786 cm$^1$. MS (ESI) m/z 380 (M+H), 402 (M+Na). HRMS (ESI) for C$_{16}$H$_{18}$N$_3$O$_4$S$_2$ [M+H] calcd: 380.07387. found: 380.07330. Anal. Calcd for C$_{16}$H$_{17}$N$_3$O$_4$S$_2$.¼H$_2$O: C, 50.05; H, 4.59; N, 10.94. Found: C, 50.40; H, 4.34; N, 10.63.

EXAMPLE 13

4-Methylsulfanyl-5-phenyl-7-(β-D-ribofuranosyl)-7H-pyrrolo[2,3-d]pyrimidine (2e)

Compound 2e was prepared as described for 2a in Example 9 from 2h (313 mg, 0.74 mmol) and phenylboronic acid as a white solid (135 mg, 49%) after final re-purification by crystallization from water/MeOH. Mp 169-170° C. $[\alpha]^{20}_D$ −49.1 (c 0.330, DMSO). $^1$H NMR (500 MHz, DMSO-d$_6$): 2.54 (s, 3H, CH$_3$S); 3.55 (ddd, 1H, $J_{gem}$=12.0 Hz, $J_{5'a,OH}$=5.7 Hz, $J_{5'a,4'}$=3.9 Hz, H-5'a); 3.64 (ddd, 1H, $J_{gem}$=11.9 Hz, $J_{5'b,OH}$=5.4 Hz, $J_{5'b,4'}$=4.0 Hz, H-5'b); 3.93 (bq, 1H, $J_{4',5'a}$=$J_{4',5'b}$=$J_{4',3'}$=3.6 Hz, H-4'); 4.12 (td, 1H, $J_{3',2'}$=$J_{3',OH}$=5.0 Hz, $J_{3',4'}$=3.3 Hz, H-3'); 4.46 (td, 1H, $J_{2',1'}$=$J_{2',OH}$=6.3 Hz, $J_{2',3'}$=5.1 Hz, H-2'); 5.06 (t, 1H, $J_{O'a}$=$J_{OH,5'b}$=5.5 Hz, OH-5'); 5.18 (d, 1H, $J_{OH,3'}$=4.9 Hz, OH-3'); 5.40 (d, 1H, $J_{OH,2'}$=6.4 Hz, OH-2'); 6.25 (d, 1H, $J_{1',2'}$=6.2 Hz, H-1'); 7.38 (m, 1H, H-p-Ph); 7.44 (m, 2H, H-m-Ph); 7.51 (m, 2H, H-o-Ph); 7.81 (s, 1H, H-6); 8.67 (s, 1H, H-2). $^{13}$C NMR (125.7 MHz, DMSO-d$_6$): 12.16 (CH$_3$S); 61.67 (CH$_2$-5'); 70.73 (CH-3'); 74.30 (CH-2'); 85.44 (CH-4'); 86.88 (CH-1'); 114.30 (C-4a); 117.01 (C-5); 124.43 (CH-6); 127.45 (CH-p-Ph); 128.15 (CH-m-Ph); 130.19 (CH-o-Ph); 133.73 (C-i-Ph); 148.94 (C-7a); 150.52 (CH-2); 161.37 (C-4). IR (ATR): v 3394, 2933, 1552, 1460, 1207, 1109, 1061, 699 cm$^1$. MS (ESI) m/z 374 (M+H), 396 (M+Na). HRMS (ESI) for C$_{18}$H$_{20}$N$_3$O$_4$S [M+H] calcd: 374.11745. found: 374.11688.

EXAMPLE 14

5-(Benzofuran-2-yl)-4-methylsulfanyl-7-(β-D-ribofuranosyl)-7H-pyrrolo[2,3-d]pyrimidine (2f)

Compound 2f was prepared as described for 2a in Example 9 from 2h (313 mg, 0.74 mmol) and benzofuran-2-boronic acid. The product after column chromatography (SiO$_2$, 3% MeOH in CHCl$_3$) was contaminated by unreacted 2h and was re-purified by crystallization from water/DMSO (5:1, 6 mL) and washing with MeOH to obtain 2f (70 mg, 23%) as a yellow powder. Mp 218-222° C. $[\alpha]^{20}_D$ −65.9 (c 0.317, DMSO). $^1$H NMR (500 MHz, DMSO-d$_6$): 2.62 (s, 3H, CH$_3$S); 3.58 (ddd, 1H, $J_{gem}$=12.0 Hz, $J_{5'a,OH}$=5.6 Hz, $J_{5'a,4'}$=3.8 Hz, H-5'a); 3.67 (ddd, 1H, $J_{gem}$=12.0 Hz, $J_{5'b,OH}$=5.3 Hz, $J_{5'b,4'}$=3.8 Hz, H-5'b); 3.96 (bq, 1H, $J_{4',5'a}$=$J_{4',5'b}$=$J_{4',3'}$=3.6 Hz, H-4'); 4.14 (td, 1H, $J_{3',2'}$=$J_{3',OH}$=5.0 Hz, $J_{3',4'}$=3.3 Hz, H-3'); 4.47 (td, 1H, $J_{2',1'}$=$J_{2',OH}$=6.2 Hz, $J_{2',3'}$=5.1 Hz, H-2'); 5.12 (t, 1H, $J_{OH,5'a}$=$J_{OH,5'b}$=5.4 Hz, OH-5'); 5.22 (d, 1H, $J_{OH,3'}$=4.9 Hz, OH-3'); 5.46 (d, 1H, $J_{OH,2'}$=6.3 Hz, OH-2'); 6.27 (d, 1H, $J_{1',2'}$=6.1 Hz, H-1'); 7.23 (d, 1H, $J_{3,7}$=1.0 Hz, H-3-benzofuryl); 7.24-7.35 (m, 2H, H-5,6-benzofuryl); 7.62 (dq, 1H, $J_{7,6}$=8.1 Hz, $J_{7,5}$=$J_{7,4}$=$J_{7,3}$=0.9 Hz, H-7-benzofuryl); 7.69 (ddd, 1H, $J_{4,5}$=7.7 Hz, $J_{4,6}$=1.4 Hz, $J_{4,7}$=0.7 Hz, H-4-benzofuryl); 8.27 (s, 1H, H-6); 8.73 (s, 1H, H-2). $^{13}$C NMR (125.7 MHz, DMSO-d$_6$): 12.41 (CH$_3$S); 61.54 (CH$_2$-5'); 70.63 (CH-3'); 74.47 (CH-2'); 85.61 (CH-4'); 87.05 (CH-1'); 105.21 (CH-3-benzofuryl); 106.09 (C-5); 111.16 (CH-7-benzofuryl); 113.55 (C-4a); 121.17 (CH-4-benzofuryl); 123.28 (CH-5-benzofuryl); 124.46 (CH-6-benzofuryl); 126.43 (CH-6); 128.94 (C-3a-benzofuryl); 149.22 (C-7a); 149.71 (C-2-benzofuryl); 151.13 (CH-2); 154.31 (C-7a-benzofuryl); 161.90 (C-4). IR (ATR): v 3401, 3223, 1547, 1439, 1258, 1034, 980, 786, 745 cm$^{-1}$. MS (ESI) m/z 414 (M+H), 436 (M+Na). HRMS (ESI) for C$_{20}$H$_{20}$N$_3$O$_5$S [M+H] calcd: 414.11237. found: 414.11176.

EXAMPLE 15

5-Ethynyl-4-methylsulfanyl-7-(β-D-ribofuranosyl)-7H-pyrrolo[2,3-d]pyrimidine (2g)

An argon-purged mixture of 2h (423 mg, 1 mmol), PdCl$_2$(PPh$_3$)$_2$ (35 mg, 0.05 mmol), CuI (19 mg, 0.1 mmol), trimethylsilylacetylene (1.4 ml, 10 mmol) and triethylamine (0.4 mL) was stirred in DMF (1.6 mL) at rt for 16 h. The volatiles were removed in vacuo and the residue was several times co-evaporated with EtOH/toluene and loaded on silica by co-evaporation. Column chromatography (SiO$_2$, 0→3% MeOH in CHCl$_3$) afforded trimethylsilylethynyl derivative contaminated by triethylammonium iodide. This material was directly deprotected by treatment with K$_2$CO$_3$ (207 mg, 1.5 mmol) in MeOH (5 mL) at rt for 2 h, followed by the co-evaporation with silica and final column chromatography (3% MeOH in CHCl$_3$) afforded 2g (212 mg, 66% in two steps), which was recrystallized from MeOH. Mp 139-143° C. $[\alpha]^{20}{}_D$ −78.5 (c 0.223, DMSO). $^1$H NMR (500 MHz, DMSO-d$_6$): 2.62 (s, 3H, CH$_3$S); 3.56 (ddd, 1H, J$_{gem}$=12.0 Hz, J$_{5'a,OH}$=5.6 Hz, J$_{5'a,4'}$=3.8 Hz, H-5'a); 3.65 (ddd, 1H, J$_{gem}$=12.0 Hz, J$_{5'b,OH}$=5.3 Hz, J$_{5'b,4}$=3.9 Hz, H-5'b); 3.92 (bq, 1H, J$_{4',5'a}$=J$_{4',5'b}$=J$_{4',3'}$=3.7 Hz, H-4'); 4.10 (td, 1H, J$_{3',2'}$=J$_{3',OH}$=5.0 Hz, J$_{3',4}$=3.4 Hz, H-3'); 4.27 (s, 1H, C≡CH); 4.37 (td, 1H, J$_{2',1'}$=J$_{2',OH}$=6.0 Hz, J$_{2',3}$=5.1 Hz, H-2'); 5.12 (t, 1H, J$_{OH,5'a}$=J$_{OH,5'b}$=5.5 Hz, OH-5'); 5.19 (d, 1H, J$_{OH,3'}$=4.9 Hz, OH-3'); 5.43 (d, 1H, J$_{OH,2'}$=6.2 Hz, OH-2'); 6.15 (d, 1H, J$_{1',2}$=5.9 Hz, H-1'); 8.13 (s, 1H, H-6); 8.65 (s, 1H, H-2). $^{13}$C NMR (125.7 MHz, DMSO-d$_6$): 11.66 (CH$_3$S); 61.49 (CH$_2$-5'); 70.58 (CH-3'); 74.52 (CH-2'); 77.01 (C≡CH); 83.58 (C≡CH); 85.59 (CH-4'); 87.15 (CH-1'); 95.34 (C-5); 115.78 (C-4a); 130.94 (CH-6); 147.85 (C-7a); 151.59 (CH-2); 162.53 (C-4). IR (ATR): v 3273, 2933, 1558, 1451, 1236, 1031, 612 cm$^{-1}$. MS (ESI) m/z 322 (M+H), 344 (M+Na). HRMS (ESI) for C$_{14}$H$_{16}$N$_3$O$_4$S [M+H] calcd: 322.08615. found: 322.08560.

EXAMPLE 16

5-Iodo-4-methylamino-7-(β-D-ribofuranosyl)-7H-pyrrolo[2,3-d]pyrimidine (3h)

A mixture of 4-chloro-5-iodo-7-(2,3,5-tri-O-benzoyl-β-D-ribofuranosyl)-7H-pyrrolo[2,3-d]pyrimidine 6 (ref.: Seela, F.; Ming, X., *Tetrahedron* 2007, 63, 9850-9861) (2.4 g, 3.31 mmol) in methylamine (33 wt. % in absolute EtOH, 25 mL) was stirred in a pressure tube at 100° C. for 5 h. After cooling the mixture was evaporated to dryness and purified by column chromatography (SiO$_2$, 3% MeOH in chloroform) to afford 3h (1.24 g, 92%) as a white solid. Crystallization from MeOH afforded colorless needles. Mp 218-223° C. $[\alpha]^{20}{}_D$ −61.3 (c 0.419, DMSO). $^1$H NMR (500 MHz, DMSO-d$_6$): 3.02 (d, 3H, J$_{CH3,NH}$=4.7 Hz, CH$_3$); 3.52 (ddd, 1H, J$_{gem}$=12.0 Hz, J$_{5'a,OH}$=6.1 Hz, J$_{5'a,4}$=3.8 Hz, H-5'a); 3.61 (ddd, 1H, J$_{gem}$=12.0 Hz, J$_{5'b,OH}$=5.1 Hz, J$_{5'b,4}$=3.8 Hz, H-5'b); 3.88 (bq, 1H, J$_{4',5'a}$=J$_{4',5'b}$=J$_{4',3'}$=3.5 Hz, H-4'); 4.06 (td, 1H, J$_{3',2'}$=J$_{3',OH}$=4.9 Hz, J$_{3',4}$=3.1 Hz, H-3'); 4.35 (td, 1H, J$_{2',1'}$=J$_{2',OH}$=6.4 Hz, J$_{2',3}$=5.1 Hz, H-2'); 5.12 (d, 1H, J$_{OH,3'}$=4.7 Hz, OH-3'); 5.16 (dd, 1H, J$_{OH,5'a}$=6.1 Hz, J$_{OH,5'b}$=5.1 Hz, OH-5'); 5.31 (d, 1H, J$_{OH,2'}$=6.5 Hz, OH-2'); 6.03 (d, 1H, J$_{1',2}$=6.3 Hz, H-1'); 6.44 (q, 1H, J$_{NH,CH3}$=4.7 Hz, NH); 7.66 (s, 1H, H-6); 8.19 (s, 1H, H-2). $^{13}$C NMR (125.7 MHz, DMSO-d$_6$): 27.90 (CH$_3$NH); 51.25 (C-5); 61.74 (CH$_2$-5'); 70.70 (CH-3'); 74.10 (CH-2'); 85.37 (CH-4'); 86.99 (CH-1'); 103.73 (C-4a); 127.17 (CH-6); 149.70 (C-7a); 152.07 (CH-2); 156.62 (C-4). IR (ATR): v 3387, 3323, 1603, 1550, 1305, 1090, 866, 596 cm$^{-1}$. MS (ESI) m/z 407 (M+H), 429 (M+Na). HRMS (ESI) for C$_{12}$H$_{16}$IN$_4$O$_4$ [M+H] calcd: 407.02162. found: 407.02111. Anal. Calcd for C$_{12}$H$_{15}$IN$_4$O$_4$: C, 35.48; H, 3.72; N, 13.79. Found: C, 35.42; H, 3.62; N, 13.42.

EXAMPLE 17

5-(Furan-2-yl)-4-methylamino-7-(β-D-ribofuranosyl)-7H-pyrrolo[2,3-d]pyrimidine (3a)

An argon-purged mixture of 3h (300 mg, 0.74 mmol), furan-2-boronic acid (124 mg, 1.11 mmol), Na$_2$CO$_3$ (235 mg, 2.22 mmol), Pd(OAc)$_2$ (8 mg, 36 µmol) and TPPTS (53 mg, 0.093 mmol) in water/MeCN (2:1, 4 mL) was stirred at 100° C. for 1 h. After cooling the mixture was neutralized using aq HCl (1 M) and concentrated to dryness. The residue was co-evaporated with silica and purified by column chromatography (SiO$_2$, 1→3% MeOH in CHCl$_3$) to afford product 3a (220 mg, 86%) as a white solid, which was crystallized from water/MeOH. Mp 114-117° C. $[\alpha]^{20}{}_D$ −70.6 (c 0.299, DMSO). $^1$H NMR (500 MHz, DMSO-d$_6$): 3.04 (d, 3H, J$_{CH3,NH}$=4.8 Hz, CH$_3$); 3.54 (dm, 1H, J$_{gem}$=12.0 Hz, H-5'a); 3.64 (dm, 1H, J$_{gem}$=11.9 Hz, H-5'b); 3.91 (q, 1H, J$_{4',5'a}$=J$_{4',5'b}$=J$_{4',3'}$=3.6 Hz, H-4'); 4.10 (td, 1H, J$_{3',2'}$=J$_{3',OH}$=4.9 Hz, J$_{3',4}$=3.3 Hz, H-3'); 4.41 (td, 1H, J$_{2',1'}$=J$_{2',OH}$=6.3 Hz, J$_{2',3}$=5.2 Hz, H-2'); 5.18 (d, 1H, J$_{OH,3}$=4.8 Hz, OH-3'); 5.25 (m, 1H, OH-5'); 5.37 (d, 1H, J$_{OH,2}$=6.4 Hz, OH-2'); 6.09 (d, 1H, J$_{1',2}$=6.2 Hz, H-1'); 6.61 (dd, 1H, J$_{4,3}$=3.3 Hz, J$_{4,5}$=1.9 Hz, H-4-furyl); 6.66 (dd, 1H, J$_{3,4}$=3.3 Hz, J$_{3,5}$=0.8 Hz, H-3-furyl); 6.85 (q, 1H, J$_{NH,CH3}$=4.8 Hz, NH); 7.76 (dd, 1H, J$_{5,4}$=1.9 Hz, J$_{5,3}$=0.8 Hz, H-5-furyl); 7.82 (s, 1H, H-6); 8.22 (s, 1H, H-2). $^{13}$C NMR (125.7 MHz, DMSO-d$_6$): 28.24 (CH$_3$NH); 61.92 (CH$_2$-5'); 70.81 (CH-3'); 74.12 (CH-2'); 85.45 (CH-4'); 87.31 (CH-1'); 100.03 (C-4a); 105.59 (CH-3-furyl); 106.35 (C-5); 112.20 (CH-4-furyl); 120.52 (CH-6); 142.39 (CH-5-furyl); 148.79 (C-2-furyl); 150.34 (C-7a); 152.27 (CH-2); 156.84 (C-4). IR (ATR): v 3649, 2934, 1624, 1319, 1021, 585, 564 cm$^{-1}$. MS (ESI) m/z 347 (M+H), 369 (M+Na). HRMS (ESI) for C$_{16}$H$_{19}$N$_4$O$_5$ [M+H] calcd: 347.13554. found: 347.13496.

EXAMPLE 18

5-(Furan-3-yl)-4-methylamino-7-(β-D-ribofuranosyl)-7H-pyrrolo[2,3-d]pyrimidine (3b)

Compound 3b was prepared as described for 3a in Example 17 from 3h (300 mg, 0.74 mmol) and furan-3-boronic acid as a yellowish foam (245 mg, 96%). Mp 90-97° C. $[\alpha]^{20}{}_D$ −56.5 (c 0.354, DMSO). $^1$H NMR (500 MHz, DMSO-d$_6$): 2.95 (d, 3H, J$_{CH3,NH}$=4.7 Hz, CH$_3$); 3.53 (ddd, 1H, J$_{gem}$=12.0 Hz, J$_{5'a,OH}$=6.3 Hz, J$_{5'a,4}$=3.9 Hz, H-5'a); 3.62 (ddd, 1H, J$_{gem}$=12.0 Hz, J$_{5'b,OH}$=5.0 Hz, J$_{5'b,4}$=3.8 Hz, H-5'b); 3.89 (bq, 1H, J$_{4',5'a}$=J$_{4',5'b}$=J$_{4',3'}$=3.6 Hz, H-4'); 4.09 (td, 1H, J$_{3',2'}$=J$_{3',OH}$=5.0 Hz, J$_{3',4}$=3.2 Hz, H-3'); 4.42 (td, 1H, J$_{2',1'}$=J$_{2',OH}$=6.4 Hz, J$_{2',3}$=5.1 Hz, H-2'); 5.12 (d, 1H, J$_{OH,3}$=4.8 Hz, OH-3'); 5.20 (dd, 1H, J$_{OH,5'a}$=6.3 Hz, J$_{OH,5'b}$=5.0 Hz, OH-5'); 5.31 (d, 1H, J$_{OH,2}$=6.5 Hz, OH-2'); 5.82 (q, 1H, J$_{NH,CH3}$=4.7 Hz, NH); 6.08 (d, 1H, J$_{1',2}$=6.3 Hz, H-1'); 6.69 (dd, 1H, J$_{4,5}$=1.8 Hz, J$_{4,2}$=0.9 Hz, H-4-furyl); 7.47 (s, 1H, H-6); 7.81 (t, 1H, J$_{5,2}$=J$_{5,4}$=1.7 Hz, H-5-furyl); 7.83 (dd, 1H, J$_{2,5}$=1.6 Hz, J$_{2,4}$=0.9 Hz, H-2-furyl); 8.21 (s, 1H, H-2). $^{13}$C NMR (125.7 MHz, DMSO-d$_6$): 28.04 (CH$_3$NH); 61.90 (CH$_2$-5'); 70.81 (CH-3'); 73.97 (CH-2'); 85.28 (CH-4'); 87.16 (CH-1'); 101.43 (C-4a); 106.23 (C-5); 111.74 (CH-4-furyl); 118.79 (C-3-furyl); 120.94 (CH-6); 139.79 (CH-2-furyl); 144.30 (CH-5-furyl); 150.11 (C-7a); 151.83 (CH-2); 157.14 (C-4). IR (ATR): v 3128, 2931, 2862, 1600, 1566, 1212, 1073, 1028, 874 cm$^{-1}$. MS (ESI) m/z 347

(M+H), 369 (M+Na). HRMS (ESI) for $C_{16}H_{19}N_4O_5$ [M+H] calcd: 347.13554. found: 347.13493.

EXAMPLE 19

4-Methylamino-7-(β-D-ribofuranosyl)-5-(thiophen-2-yl)-7H-pyrrolo[2,3-d]pyrimidine (3c)

Compound 3c was prepared as described for 3a in Example 17 from 3h (150 mg, 0.37 mmol) and thiophene-2-boronic acid as a white solid (126 mg, 94%), which was crystallized from water/MeOH. Mp 183-185° C. $[\alpha]^{20}_D$ −52.1 (c 0.296, DMSO). $^1$H NMR (500 MHz, DMSO-$d_6$): 2.95 (d, 3H, $J_{CH3,NH}$=4.8 Hz, $CH_3$); 3.53 (ddd, 1H, $J_{gem}$=11.9 Hz, $J_{5'a,OH}$=5.9 Hz, $J_{5'a,4'}$=3.6 Hz, H-5'a); 3.63 (bdt, 1H, $J_{gem}$=11.9 Hz, $J_{5'b,OH}$=$J_{5'b,4'}$=4.2 Hz, H-5'b); 3.91 (bq, 1H, $J_{4',5'a}$=$J_{4',5'b}$=$J_{4',3'}$=3.5 Hz, H-4'); 4.09 (td, 1H, $J_{3',2'}$=$J_{3',OH}$=4.9 Hz, $J_{3',4'}$=3.2 Hz, H-3'); 4.43 (td, 1H, $J_{2',1'}$=$J_{2',OH}$=6.4 Hz, $J_{2',3'}$=5.2 Hz, H-2'); 5.14 (d, 1H, $J_{OH,3'}$=4.7 Hz, OH-3'); 5.21 (bt, 1H, $J_{OH,5'a}$=$J_{OH,5'b}$=5.5 Hz, OH-5'); 5.34 (d, 1H, $J_{OH,2'}$=6.5 Hz, OH-2'); 5.83 (q, 1H, $J_{NH,CH3}$=4.8 Hz, NH); 6.10 (d, 1H, $J_{1',2'}$=6.3 Hz, H-1'); 7.14 (dd, 1H, $J_{3,4}$=3.5 Hz, $J_{3,5}$=1.2 Hz, H-3-thienyl); 7.18 (dd, 1H, $J_{4,5}$=5.2 Hz, $J_{4,3}$=3.5 Hz, H-4-thienyl); 7.56 (dd, 1H, $J_{5,4}$=5.2 Hz, $J_{5,3}$=1.2 Hz, H-5-thienyl); 7.59 (s, 1H, H-6); 8.24 (s, 1H, H-2). $^{13}$C NMR (125.7 MHz, DMSO-$d_6$): 28.02 ($CH_3$NH); 61.79 ($CH_2$-5'); 70.78 (CH-3'); 74.09 (CH-2'); 85.40 (CH-4'); 87.19 (CH-1'); 101.08 (C-4a); 108.54 (C-5); 122.00 (CH-6); 125.93 (CH-5-thienyl); 126.50 (CH-3-thienyl); 128.61 (CH-4-thienyl); 135.77 (C-2-thienyl); 150.08 (C-7a); 152.09 (CH-2); 156.96 (C-4). IR (ATR): ν 3152, 2929, 2863, 1610, 1992, 1303, 1061, 1023, 641 cm$^{-1}$. MS (ESI) m/z 363 (M+H), 385 (M+Na). HRMS (ESI) for $C_{16}H_{19}N_4O_4S$ [M+H] calcd: 363.11270. found: 363.11204.

EXAMPLE 20

4-Methylamino-7-(β-D-ribofuranosyl)-5-(thiophen-3-yl)-7H-pyrrolo[2,3-d]pyrimidine (3d)

Compound 3d was prepared as described for 3a in Example 17 from 3h (300 mg, 0.74 mmol) and thiophene-3-boronic acid as a white solid (263 mg, 98%), which was crystallized from water/MeOH. Mp 135-138° C. $[\alpha]^{20}_D$ −52.5 (c 0.402, DMSO). $^1$H NMR (500 MHz, DMSO-$d_6$): 2.94 (d, 3H, $J_{CH3,NH}$=4.8 Hz, $CH_3$); 3.53 (dm, 1H, $J_{gem}$=11.9 Hz, H-5'a); 3.63 (dm, 1H, $J_{gem}$=11.9 Hz, H-5'b); 3.90 (q, 1H, $J_{4',5'a}$=$J_{4',5'b}$=$J_{4',3'}$=3.5 Hz, H-4'); 4.10 (m, 1H, H-3'); 4.43 (btd, 1H, $J_{2',1'}$=$J_{2',OH}$=6.4 Hz, $J_{2',3'}$=5.4 Hz, H-2'); 5.13 (d, 1H, $J_{OH,3'}$=4.7 Hz, OH-3'); 5.21 (bs, 1H, OH-5'); 5.32 (d, 1H, $J_{OH,2'}$=6.5 Hz, OH-2'); 5.70 (q, 1H, $J_{NH,CH3}$=4.8 Hz, NH); 6.10 (d, 1H, $J_{1',2'}$=6.3 Hz, H-1'); 7.27 (dd, 1H, $J_{4,5}$=4.9 Hz, $J_{4,2}$=1.4 Hz, H-4-thienyl); 7.51 (dd, 1H, $J_{2,5}$=2.9 Hz, $J_{2,4}$=1.4 Hz, H-2-thienyl); 7.52 (s, 1H, H-6); 7.71 (dd, 1H, $J_{5,4}$=4.9 Hz, $J_{5,2}$=2.9 Hz, H-5-thienyl); 8.23 (s, 1H, H-2). $^{13}$C NMR (125.7 MHz, DMSO-$d_6$): 28.06 ($CH_3$NH); 61.89 ($CH_2$-5'); 70.82 (CH-3'); 74.02 (CH-2'); 85.31 (CH-4'); 87.20 (CH-1'); 101.22 (C-4a); 111.04 (C-5); 121.09 (CH-6); 122.10 (CH-2-thienyl); 127.60 (CH-5-thienyl); 128.62 (CH-4-thienyl); 135.96 (C-3-thienyl); 150.02 (C-7a); 151.77 (CH-2); 157.10 (C-4). IR (ATR): ν 3152, 2933, 2863, 1608, 1390, 1303, 1061, 785 cm$^1$. MS (ESI) m/z 363 (M+H), 385 (M+Na). HRMS (ESI) for $C_{16}H_{19}N_4O_4S$ [M+H] calcd: 363.11270. found: 363.11204.

EXAMPLE 21

4-Methylamino-5-phenyl-7-(β-D-ribofuranosyl)-7H-pyrrolo[2,3-d]pyrimidine (3e)

Compound 3e was prepared as described for 3a in Example 17 from 3h (300 mg, 0.74 mmol) and phenylboronic acid as a white solid (250 mg, 95%), which was crystallized from water/MeOH. Mp 149-153° C. $[\alpha]^{20}_D$ −53.3 (c 0.304, DMSO). $^1$H NMR (500 MHz, DMSO-$d_6$): 2.92 (d, 3H, $J_{CH3,NH}$=4.8 Hz, $CH_3$); 3.54 (bdm, 1H, $J_{gem}$=11.9 Hz, H-5'a); 3.63 (bdd, 1H, $J_{gem}$=11.9 Hz, $J_{5'b,4'}$=3.6 Hz, H-5'b); 3.91 (q, 1H, $J_{4',5'a}$=$J_{4',5'b}$=$J_{4',3'}$=3.5 Hz, H-4'); 4.11 (m, 1H, H-3'); 4.46 (bq, 1H, $J_{2',1'}$=$J_{2',OH}$=$J_{2',3'}$=5.7 Hz, H-2'); 5.13 (d, 1H, $J_{OH,3'}$=4.7 Hz, OH-3'); 5.21 (m, 1H, OH-5'); 5.33 (d, 1H, $J_{OH,2'}$=6.5 Hz, OH-2'); 5.58 (q, 1H, $J_{NH,CH3}$=4.8 Hz, NH); 6.13 (d, 1H, $J_{1',2'}$=6.3 Hz, H-1'); 7.37 (m, 1H, H-p-Ph); 7.44-7.51 (m, 4H, H-o,m-Ph); 7.52 (s, 1H, H-6); 8.24 (s, 1H, H-2). $^{13}$C NMR (125.7 MHz, DMSO-$d_6$): 28.12 ($CH_3$NH); 61.88 ($CH_2$-5'); 70.83 (CH-3'); 74.03 (CH-2'); 85.32 (CH-4'); 87.26 (CH-1'); 100.91 (C-4a); 116.38 (C-5); 121.24 (CH-6); 127.05 (CH-p-Ph); 128.55 (CH-o-Ph); 129.27 (CH-m-Ph); 134.69 (C-i-Ph); 150.31 (C-7a); 151.72 (CH-2); 157.01 (C-4). IR (ATR): ν 3192, 2953, 1604, 1573, 1517, 1111, 1061, 648 cm$^1$. MS (ESI) m/z 357 (M+H), 379 (M+Na). HRMS (ESI) for $C_{18}H_{21}N_4O_4$ [M+H] calcd: 357.15628. found: 357.15565.

EXAMPLE 22

5-(Benzofuran-2-yl)-4-methylamino-7-(β-D-ribofuranosyl)-7H-pyrrolo[2,3-d]pyrimidine (3f)

Compound 3f was prepared as described for 3a in Example 17 from 3h (300 mg, 0.74 mmol) and benzofuran-2-boronic acid. After column chromatography, product was re-purified by crystallization from water/MeOH to obtain 3f (187 mg, 64%) as a brownish solid. Mp 203-206° C. $[\alpha]^{20}_D$ −65.2 (c 0.248, DMSO). $^1$H NMR (500 MHz, DMSO-$d_6$): 3.09 (d, 3H, $J_{CH3,NH}$=4.7 Hz, $CH_3$); 3.58 (bdm, 1H, $J_{gem}$=12.0 Hz, H-5'a); 3.68 (bdt, 1H, $J_{gem}$=12.0 Hz, $J_{5'b,OH}$=$J_{5'b,4'}$=4.5 Hz, H-5'b); 3.94 (m, 1H, H-4'); 4.14 (m, 1H, H-3'); 4.46 (m, 1H, H-2'); 5.18 (bd, 1H, $J_{OH,3'}$=4.9 Hz, OH-3'); 5.24 (bt, 1H, $J_{OH,5'a}$=$J_{OH,5'b}$=5.7 Hz, OH-5'); 5.41 (bd, 1H, $J_{OH,2'}$=6.4 Hz, OH-2'); 6.15 (bd, 1H, $J_{1',2'}$=6.1 Hz, H-1'); 6.99 (q, 1H, $J_{NH,CH3}$=4.7 Hz, NH); 7.12 (d, 1H, $J_{3,7}$=0.9 Hz, H-3-benzofuryl); 7.26-7.33 (m, 2H, H-5,6-benzofuryl); 7.65 (m, 1H, H-4-benzofuryl); 7.73 (m, 1H, H-7-benzofuryl); 8.09 (s, 1H, H-6); 8.28 (s, 1H, H-2). $^{13}$C NMR (125.7 MHz, DMSO-$d_6$): 28.22 ($CH_3$NH); 61.79 ($CH_2$-5 '); 70.70 (CH-3'); 74.15 (CH-2'); 85.45 (CH-4'); 87.36 (CH-1'); 100.05 (C-4a); 101.82 (CH-3-benzofuryl); 105.57 (C-5); 111.56 (CH-7-benzofuryl); 120.77 (CH-4-benzofuryl); 122.68 (CH-6); 123.63 (CH-5-benzofuryl); 123.96 (CH-6-benzofuryl); 129.05 (C-3a-benzofuryl); 150.54 (C-7a); 151.24 (C-2-benzofuryl); 152.41 (CH-2); 154.04 (C-7a-benzofuryl); 156.77 (C-4). IR (ATR): ν 3418, 2930, 1621, 1602, 1458, 1201, 1105 cm$^1$. MS (ESI) m/z 397 (M+H), 419 (M+Na). HRMS (ESI) for $C_{20}H_{21}N_4O_5$ [M+H] calcd: 397.15119. found: 397.15059. Anal. Calcd for $C_{20}H_{20}N_4O_5 \cdot 1.7H_2O$: C, 56.25; H, 5.52; N, 13.12. Found: C, 56.52; H, 5.16; N, 12.74.

EXAMPLE 23

5-Ethynyl-4-methylamino-7-(β-D-ribofuranosyl)-7H-pyrrolo[2,3-d]pyrimidine (3g)

An argon-purged mixture of 3h (406 mg, 1 mmol), $PdCl_2(PPh_3)_2$ (35 mg, 0.05 mmol), CuI (19 mg, 0.1 mmol), trimethylsilylacetylene (1.4 mL, 10 mmol) and triethylamine (0.4 mL) was stirred in DMF (1.6 mL) at rt for 12 h. The volatiles were removed in vacuo and the residue was several times co-evaporated with EtOH/toluene and loaded on silica by co-evaporation. Column chromatography ($SiO_2$, 0→3% MeOH in $CHCl_3$) afforded trimethylsilylethynyl derivative contaminated by triethylammonium iodide. This material was directly deprotected by treatment with $K_2CO_3$ (207 mg, 1.5 mmol) in MeOH (5 mL) at rt for 5 h, followed by the co-evaporation with silica and final column chromatography (3% MeOH in $CHCl_3$) afforded 3g (237 mg, 78% in two steps), which was recrystallized from MeOH/chloroform. Mp 193-195° C. $[\alpha]^{20}_D$ −83.4 (c 0.248, DMSO). $^1$H NMR (500 MHz, DMSO-$d_6$): 3.01 (d, 3H, $J_{CH3,NH}$=4.8 Hz, $CH_3$); 3.53 (ddd, 1H, $J_{gem}$=12.0 Hz, $J_{5'a,OH}$=5.6 Hz, $J_{5'a,4'}$=3.8 Hz, H-5'a); 3.63 (bdt, 1H, $J_{gem}$=12.0 Hz, $J_{5'b,OH}$=$J_{5'b,4'}$=4.1 Hz, H-5'b); 3.90 (q, 1H, $J_{4',5'a}$=$J_{4',5'b}$=$J_{4',3'}$=3.5 Hz, H-4'); 4.08 (bdd, 1H, $J_{3',2'}$=4.8 Hz, $J_{3',4'}$=3.5 Hz, H-3'); 4.27 (s, 1H, C≡CH); 4.37 (bt, 1H, $J_{2'1'}$=$J_{2',3'}$=5.5 Hz, H-2'); 5.14 (bs, 1H, OH-3'); 5.21 (bt, 1H, $J_{OH,5'a}$=$J_{OH,5'b}$=5.5 Hz, OH-5'); 5.35 (bs, 1H, OH-2'); 6.02 (d, 1H, $J_{1',2'}$=6.1 Hz, H-1'); 6.37 (q, 1H, $J_{NH,CH3}$=4.8 Hz, NH); 7.81 (s, 1H, H-6); 8.21 (s, 1H, H-2). $^{13}$C NMR (125.7 MHz, DMSO-$d_6$): 27.83 ($CH_3$NH); 61.70 ($CH_2$-5'); 70.69 (CH-3'); 74.20 (CH-2'); 77.36 (C≡CH); 83.50 (C≡CH); 85.47 (CH-4'); 87.42 (CH-1'); 93.84 (C-5); 102.91 (C-4a); 127.53 (CH-6); 148.92 (C-7a); 152.86 (CH-2); 157.04 (C-4). IR (ATR): v 3298, 3273, 2948, 1618, 1516, 1326, 1031, 681, 560 cm$^1$. MS (ESI) m/z 305 (M+H), 327 (M+Na). HRMS (ESI) for $C_{14}H_{17}N_4O_4$ [M+H] calcd: 305.12498. found: 364.12438. Anal. Calcd for $C_{14}H_{16}N_4O_4 \cdot ¼H_2O$: C, 54.45; H, 5.39; N, 18.14. Found: C, 54.67; H, 5.31; N, 17.95.

EXAMPLE 24

4-Dimethylamino-5-iodo-7-(β-D-ribofuranosyl)-7H-pyrrolo[2,3-d]pyrimidine (4h)

A mixture of 4-chloro-5-iodo-7-(2,3,5-tri-O-benzoyl-β-D-ribofuranosyl)-7H-pyrrolo[2,3-d]pyrimidine 6 (ref.: Seela, F.; Ming, X., *Tetrahedron* 2007, 63, 9850-9861)(5.79 g, 8 mmol), aq. dimethylamine (40% w/w, 10 mL) in dioxane (10 mL) was stirred in a steel bomb at 120° C. for 8 h. After cooling, the mixture was evaporated to dryness and the residue was co-evaporated several times with water. Crystallization from water afforded 16 (2.84 g, 84%) as white needles. Mp 195-197° C. $[\alpha]_D$ −39.0 (c 0.290, DMSO). $^1$H NMR (500 MHz, DMSO-$d_6$): 3.16 (s, 6H, $(CH_3)_2$N); 3.54 (ddd, 1H, $J_{gem}$=11.9 Hz, $J_{5'a,OH}$=5.8 Hz, $J_{5'a,4}$=3.8 Hz, H-5'a); 3.62 (ddd, 1H, $J_{gem}$=11.9 Hz, $J_{5'b,OH}$=5.2 Hz, $J_{5'b,4}$=3.9 Hz, H-5'b); 3.89 (bq, 1H, $J_{4',5'a}$=$J_{4',5'b}$=$J_{4',3'}$=3.5 Hz, H-4'); 4.07 (td, 1H, $J_{3',2'}$=$J_{3',OH}$=5.0 Hz, $J_{3',4'}$=3.2 Hz, H-3'); 4.36 (td, 1H, =$J_{2',OH}$=6.3 Hz, $J_{2',3}$=5.1 Hz, H-2'); 5.13 (t, 1H, $J_{OH,5'a}$=$J_{OH,5'b}$=5.5 Hz, OH-5'); 5.13 (d, 1H, $J_{OH,3'}$=4.7 Hz, OH-3'); 5.33 (d, 1H, $J_{OH,2'}$=6.4 Hz, OH-2'); 6.11 (d, 1H, $J_{1',2'}$=6.3 Hz, H-1'); 7.86 (s, 1H, H-6); 8.24 (s, 1H, H-2). $^{13}$C NMR (125.7 MHz, DMSO-$d_6$): 43.28 ($(CH_3)_2$N); 53.85 (C-5); 61.66 ($CH_2$-5'); 70.65 (CH-3'); 74.12 (CH-2'); 85.36 (CH-4'); 86.77 (CH-1'); 106.62 (C-4a); 129.62 (CH-6); 150.46 (CH-2); 152.13 (C-7a); 160.31 (C-4). IR (ATR): v 1580, 1536, 1422, 1222, 1127, 1060, 1013, 947, 760, 600 cm$^{-1}$. MS (ESI) m/z 421 (M+H), 443 (M+Na). HRMS (ESI) for $C_{13}H_{18}N_4O_4I$ [M+H] calcd: 421.03672. found: 421.03663. Anal. Calcd for $C_{13}H_{17}N_4O_4I$: C, 37.16; H, 4.08; N, 13.33. Found: C, 37.24; H, 4.04; N, 13.02.

EXAMPLE 25

4-Dimethylamino-5-(furan-2-yl)-7-(β-D-ribofuranosyl)-7H-pyrrolo[2,3-d]pyrimidine (4a)

An argon-purged mixture of iodide 4h (420 mg, 1 mmol), furan-2-boronic acid (168 mg, 1.5 mmol), $Na_2CO_3$ (318 mg, 3 mmol), Pd(OAc)$_2$ (11 mg, 49 µmol) and TPPTS (71 mg, 0.125 mmol) in water/MeCN (2:1, 5 mL) was stirred at 100° C. for 3 h. After cooling, the mixture was neutralized using aq HCl (1 M), concentrated to dryness in vacuo and the residue was purified by reverse phase HPFC (C-18, 0>100% MeOH in water). Re-purification by column chromatography ($SiO_2$, 2.5% MeOH in chloroform) furnished 4a (176 mg, 49%) as a beige foam. Reverse phase HPFC also provided a product of reductive dehalogenation 4-dimethylamino-7-(β-D-ribofuranosyl)-7H-pyrrolo[2,3-c]pyrimidine (73 mg, 25%). Mp 97-103° C. $[\alpha]^{20}_D$ −42.8 (c 0.358, DMSO). $^1$H NMR (500 MHz, DMSO-$d_6$): 2.84 (s, 6H, $(CH_3)_2$N); 3.54 (ddd, 1H, $J_{gem}$=11.9 Hz, $J_{5'a,OH}$=6.0 Hz, $J_{5'a,4'}$=3.8 Hz, H-5'a); 3.62 (ddd, 1H, $J_{gem}$=11.9 Hz, $J_{5'b,OH}$=5.1 Hz, $J_{5'b,4'}$=3.8 Hz, H-5'b); 3.90 (btd, 1H, $J_{4',5'a}$=$J_{4',5'b}$=3.8 Hz, $J_{4',3}$=3.2 Hz, H-4'); 4.10 (m, 1H, H-3'); 4.42 (td, 1H, $J_{2',1'}$=$J_{2',OH}$=6.4 Hz, $J_{2',3}$=5.1 Hz, H-2'); 5.14 (d, 1H, $J_{OH,3}$=4.8 Hz, OH-3'); 5.15 (dd, 1H, $J_{OH,5'a}$=5.9 Hz, $J_{OH,5'b}$=5.1 Hz, OH-5'); 5.35 (d, 1H, $J_{OH,2'}$=6.5 Hz, OH-2'); 6.17 (d, 1H, $J_{1',2}$=6.4 Hz, H-1'); 6.51 (dd, 1H, $J_{3,4}$=3.2 Hz, $J_{3,5}$=0.9 Hz, H-3-furyl); 6.58 (dd, 1H, $J_{4,3}$=3.2 Hz, $J_{4,5}$=1.9 Hz, H-4-furyl); 7.75 (dd, 1H, $J_{5,4}$=1.9 Hz, $J_{5,3}$=0.9 Hz, H-5-furyl); 7.75 (s, 1H, H-6); 8.25 (s, 1H, H-2). $^{13}$C NMR (125.7 MHz, DMSO-$d_6$): 39.44 ($(CH_3)_2$N); 61.73 ($CH_2$-5'); 70.74 (CH-3'); 74.10 (CH-2'); 85.35 (CH-4'); 86.98 (CH-1'); 102.05 (C-4a); 106.87 (C-5); 107.61 (CH-3-furyl); 111.74 (CH-4-furyl); 122.92 (CH-6); 142.56 (CH-5-furyl); 149.33 (C-2-furyl); 150.71 (CH-2); 152.01 (C-7a); 159.64 (C-4). IR (ATR): v 1574, 1515, 1450, 1420, 1410, 1203, 1120, 1077, 1058 cm$^{-1}$. MS (ESI) m/z 361 (M+H), 383 (M+Na). HRMS (ESI) for $C_{17}H_{21}N_4O_5$ [M+H] calcd: 361.15065. found: 361.15057.

EXAMPLE 26

4-Dimethylamino-5-(furan-3-yl)-7-(β-D-ribofuranosyl)-7H-pyrrolo[2,3-d]pyrimidine (4b)

Compound 4b was prepared as described for 4a in Example 25 from 4h (420 mg, 1 mmol) and furan-3-boronic acid as a yellowish foam (159 mg, 44%). Mp 94-97° C. $[\alpha]_D$ −29.9 (c 0.304, DMSO). $^1$H NMR (500 MHz, DMSO-$d_6$): 2.86 (s, 6H, $(CH_3)_2$N); 3.53 (dm, 1H, $J_{gem}$=11.9 Hz, H-5'a); 3.62 (dm, 1H, $J_{gem}$=11.9 Hz, H-5b); 3.90 (td, 1H, $J_{4',5'a}$=$J_{4',5'b}$=3.9 Hz, $J_{4',3}$=3.3 Hz, H-4'); 4.10 (m, 1H, H-3'); 4.42 (td, 1H, $J_{2',1'}$=$J_{2',OH}$=6.3 Hz, $J_{2',3}$=5.3 Hz, H-2'); 5.13 (m, 1H, OH-5'); 5.14 (d, 1H, $J_{OH,3'}$=4.8 Hz, OH-3'); 5.33 (d, 1H, $J_{OH,2'}$=6.4 Hz, OH-2'); 6.16 (d, 1H, $J_{1',2}$=6.3 Hz, H-1'); 6.66 (dd, 1H, $J_{4,5}$=1.8 Hz, $J_{4,2}$=0.9 Hz, H-4-furyl); 7.63 (s, 1H, H-6); 7.75 (t, 1H, $J_{5,2}$=$J_{5,4}$=1.7 Hz, H-5-furyl); 7.79 (dd, 1H, $J_{2,5}$=1.6 Hz, $J_{2,4}$=0.9 Hz, H-2-furyl); 8.27 (s, 1H, H-2). $^{13}$C NMR (125.7 MHz, DMSO-$d_6$): 41.11 ($(CH_3)_2$N); 61.86 ($CH_2$-5'); 70.78 (CH-3'); 73.96 (CH-2'); 85.27 (CH-4');

86.85 (CH-1'); 103.41 (C-4a); 107.26 (C-5); 111.99 (CH-4-furyl); 120.25 (C-3-furyl); 121.73 (CH-6); 139.50 (CH-2-furyl); 143.75 (C-5-furyl); 150.33 (CH-2); 152.27 (C-7a); 160.61 (C-4). IR (ATR): v 1572, 1420, 1118, 1077, 1060, 1018, 873, 791, 599 cm$^{-1}$. MS (ESI) m/z 361 (M+H), 383 (M+Na). HRMS (ESI) for $C_{17}H_{21}N_4O_5$ [M+H] calcd: 361.15065. found: 361.15058.

EXAMPLE 27

4-Dimethylamino-7-(β-D-ribofuranosyl)-5-(thiophen-2-yl)-7H-pyrrolo[2,3-d]pyrimidine (4c)

Compound 4c was prepared as described for 4a in Example 25 from 4h (420 mg, 1 mmol) and thiophene-2-boronic acid as a brownish foam (183 mg, 49%). Reverse phase HPFC also provided a product of reductive dehalogenation 4-dimethylamino-7-(β-D-ribofuranosyl)-7H-pyrrolo[2,3-c]pyrimidine (72 mg, 24%). Mp 92-99° C. $[\alpha]_D$ −36.8 (c 0.231, DMSO). $^1$H NMR (500 MHz, DMSO-d$_6$): 2.79 (s, 6H, (CH$_3$)$_2$N); 3.54 (ddd, 1H, $J_{gem}$=11.9 Hz, $J_{5'a,OH}$=5.9 Hz, $J_{5'a,4'}$=3.7 Hz, H-5'a); 3.62 (ddd, 1H, $J_{gem}$=11.9 Hz, $J_{5'b,OH}$=5.1 Hz, $J_{5'b,4}$=3.8 Hz, H-5'b); 3.90 (bq, 1H, $J_{4'5'a}$=$J_{4'5'b}$=$J_{4',3}$=3.5 Hz, H-4'); 4.09 (td, 1H, $J_{3',2'}$=$J_{3',OH}$=4.9 Hz, $J_{3',4'}$=3.1 Hz, H-3'); 4.43 (td, 1H, $J_{2',1'}$=$J_{2',OH}$=6.4 Hz, $J_{2',3}$=5.1 Hz, H-2'); 5.14 (t, 1H, $J_{OH,3'}$=4.7 Hz); 5.15 (bt, 1H, $J_{OH,5'a}$=$J_{OH,5'b}$=5.5 Hz, OH-5'); 5.35 (d, 1H, $J_{OH,2'}$=6.5 Hz, OH-2'); 6.17 (d, 1H, $J_{1',2'}$=6.4 Hz, H-1'); 7.07 (dd, 1H, $J_{3,4}$=3.5 Hz, $J_{3,5}$=1.2 Hz, H-3-thienyl); 7.12 (dd, 1H, $J_{4,5}$=5.1 Hz, $J_{4,3}$=3.5 Hz, H-4-thienyl); 7.53 (dd, 1H, $J_{5,4}$=5.1 Hz, $J_{5,3}$=1.2 Hz, H-5-thienyl); 7.70 (s, 1H, H-6); 8.27 (s, 1H, H-2). $^{13}$C NMR (125.7 MHz, DMSO-d$_6$): 40.61 ((CH$_3$)$_2$N); 61.74 (CH$_2$-5'); 70.76 (CH-3'); 74.07 (CH-2'); 85.37 (CH-4'); 86.92 (CH-1'); 102.86 (C-4a); 109.55 (C-5); 122.55 (CH-6); 125.74 (CH-5-thienyl); 126.54 (CH-3-thienyl); 127.90 (CH-4-thienyl); 137.24 (C-2-thienyl); 150.58 (CH-2); 152.12 (C-7a); 160.10 (C-4). IR (ATR): v 1571, 1544, 1420, 1410, 1120, 1079, 1044, 794, 694 cm$^{-1}$. MS (ESI) m/z 377 (M+H), 399 (M+Na). HRMS (ESI) for $C_{17}H_{21}N_4O_4S$ [M+H] calcd: 377.12780. found: 377.12776.

EXAMPLE 28

4-Dimethylamino-7-(β-D-ribofuranosyl)-5-(thiophen-3-yl)-7H-pyrrolo[2,3-d]pyrimidine (4d)

Compound 4d was prepared as described for 4a in Example 25 from 4h (420 mg, 1 mmol) and thiophene-3-boronic acid as a white foam (206 mg, 55%). Reverse phase HPFC also provided a product of reductive dehalogenation 4-dimethylamino-7-(β-D-ribofuranosyl)-7H-pyrrolo[2,3-d]pyrimidine (36 mg, 12%). Mp 99-103° C. $[\alpha]_D$ −28.8 (c 0.184, DMSO). $^1$H NMR (500 MHz, DMSO-d$_6$): 2.78 (s, 6H, (CH$_3$)$_2$N); 3.53 (ddd, 1H, $J_{gem}$=11.9 Hz, $J_{5'a,OH}$=6.0 Hz, $J_{5'a,4}$=4.0 Hz, H-5'a); 3.62 (ddd, 1H, $J_{gem}$=11.9 Hz, $J_{5'b,OH}$=5.2 Hz, $J_{5'b,4}$=3.8 Hz, H-5'b); 3.90 (td, 1H, $J_{4',5'a}$=$J_{4',5'b}$=3.9 Hz, $J_{4',3}$=3.2 Hz, H-4'); 4.10 (td, 1H, $J_{3',2'}$=$J_{3',OH}$=5.0 Hz, $J_{3',4}$=3.2 Hz, H-3'); 4.44 (td, 1H, $J_{2',1'}$=$J_{2',OH}$=6.4 Hz, $J_{2',3}$=5.2 Hz, H-2'); 5.14 (d, 1H, $J_{OH,3}$=4.8 Hz, OH-3'); 5.14 (dd, 1H, $J_{OH,5'a}$=6.0 Hz, $J_{OH,5'}$=5.2 Hz, OH-5'); 5.33 (d, 1H, $J_{OH,2'}$=6.5 Hz, OH-2'); 6.17 (d, 1H, $J_{1',2'}$=6.4 Hz, H-1'); 7.23 (dd, 1H, $J_{4,5}$=4.9 Hz, $J_{4,2}$=1.3 Hz, H-4-thienyl); 7.47 (dd, 1H, $J_{2,5}$=3.0 Hz, $J_{2,4}$=1.3 Hz, H-2-thienyl); 7.62 (dd, 1H, $J_{5,4}$=4.9 Hz, $J_{5,2}$=3.0 Hz, H-5-thienyl); 7.66 (s, 1H, H-6); 8.27 (s, 1H, H-2). $^{13}$C NMR (125.7 MHz, DMSO-d$_6$): 40.77 ((CH$_3$)$_2$N); 61.85 (CH$_2$-5'); 70.79 (CH-3'); 73.96 (CH-2'); 85.29 (CH-4'); 86.89 (CH-1'); 102.95 (C-4a); 112.02 (C-5); 121.43 (CH-2-thienyl); 121.73 (CH-6); 126.41 (CH-5-thienyl); 128.82 (CH-4-thienyl); 136.19 (C-3-thienyl); 150.35 (CH-2); 152.13 (C-7a); 160.41 (C-4). IR (ATR): v 1571, 1546, 1458, 1406, 1120, 1080, 1047, 1027, 855, 780, 614 cm$^1$. MS (ESI) m/z 377 (M+H), 399 (M+Na). HRMS (ESI) for $C_{17}H_{21}N_4O_4S$ [M+H] calcd: 377.12780. found: 377.12770.

EXAMPLE 29

4-Dimethylamino-5-phenyl-7-(β-D-ribofuranosyl)-7H-pyrrolo[2,3-d]pyrimidine (4e)

Compound 4e was prepared as described for 4a in Example 25 from 4h (420 mg, 1 mmol) and phenylboronic acid as a colorless foam (156 mg, 42%). $[\alpha]_D$ −24.0 (c 0.337, DMSO). $^1$H NMR (500 MHz, DMSO-d$_6$): 2.74 (s, 6H, (CH$_3$)$_2$N); 3.54 (ddd, 1H, $J_{gem}$=11.9 Hz, $J_{5'a,OH}$=5.9 Hz, $J_{5'a,4'}$=3.9 Hz, H-5'a); 3.63 (ddd, 1H, $J_{gem}$=11.9 Hz, $J_{5'b,OH}$=5.1 Hz, $J_{5'b,4}$=3.8 Hz, H-5'b); 3.91 (td, 1H, $J_{4',5'a}$=$J_{4',5'b}$=3.8 Hz, $J_{4',3}$=3.3 Hz, H-4'); 4.11 (m, 1H, H-3'); 4.47 (bq, 1H, $J_{2',1}$=$J_{2',OH}$=$J_{2',3}$=5.6 Hz, H-2'); 5.15 (bt, 1H, $J_{OH,5'a}$=$J_{OH,5'b}$=5.5 Hz, OH-5'); 5.15 (m, 1H, OH-3'); 5.35 (bd, 1H, $J_{OH,2}$=6.2 Hz, OH-2'); 6.19 (d, 1H, $J_{1',2}$=6.3 Hz, H-1'); 7.32 (m, 1H, H-p-Ph); 7.40-7.48 (m, 2×2H, H-m-Ph); 7.66 (s, 1H, H-6); 8.28 (s, 1H, H-2). $^{13}$C NMR (125.7 MHz, DMSO-d$_6$): 40.84 ((CH$_3$)$_2$N); 61.83 (CH$_2$-5'); 70.80 (CH-3'); 74.00 (CH-2'); 85.31 (CH-4'); 87.00 (CH-1'); 102.29 (C-4a); 117.22 (C-5); 121.92 (CH-6); 126.59 (CH-p-Ph); 128.28 (CH-o-Ph); 128.72 (CH-m-Ph); 136.00 (C-i-Ph); 150.37 (CH-2); 152.47 (C-7a); 160.15 (C-4). IR (ATR): v 1566, 1420, 1410, 1122, 1081, 1060, 1035, 1014, 761, 700 cm$^1$. MS (ESI) m/z 371 (M+H), 393 (M+Na). HRMS (ESI) for $C_{19}H_{23}N_4O_4$ [M+H] calcd: 371.17138. found: 371.17012.

EXAMPLE 30

5-(Benzofuran-2-yl)-4-dimethylamino-7-(β-D-ribofuranosyl)-7H-pyrrolo[2,3-d]pyrimidine (4f)

Compound 4f was prepared as described for 4a in Example 25 from 4h (420 mg, 1 mmol) and benzofuran-2-boronic acid. Re-purification by column chromatography (SiO$_2$) after reverse phase HPFC was omitted (as not required) and 4f (283 mg, 69%) was obtained as a white solid, which was crystallized from MeOH. Mp 159-161° C. $[\alpha]_D$ −36.4 (c 0.261, DMSO). $^1$H NMR (500 MHz, DMSO-d$_6$): 2.89 (s, 6H, (CH$_3$)$_2$N); 3.56 (ddd, 1H, $J_{gem}$=12.0 Hz, $J_{5'a,OH}$=5.9 Hz, $J_{5'a,4'}$=3.7 Hz, H-5'a); 3.65 (ddd, 1H, $J_{gem}$=12.0 Hz, $J_{5'b,OH}$=5.2 Hz, $J_{5'b,4}$=3.8 Hz, H-5'b); 3.94 (q, 1H, $J_{4',5'a}$=$J_{4',5'b}$=$J_{4',3}$=3.5 Hz, H-4'); 4.13 (td, 1H, $J_{3',2'}$=$J_{3',OH}$=5.0 Hz, $J_{3',4}$=3.2 Hz, H-3'); 4.46 (td, 1H, $J_{2',1'}$=$J_{2',OH}$=6.3 Hz, $J_{2',3}$=5.1 Hz, H-2'); 5.17 (dd, 1H, $J_{OH,5'a}$=5.9 Hz, $J_{OH,5'b}$=5.2 Hz, OH-5'); 5.17 (d, 1H, $J_{OH,3}$=4.8 Hz, OH-3'); 5.40 (d, 1H, $J_{OH,2}$=6.4 Hz, OH-2'); 6.21 (d, 1H, $J_{1',2}$=6.2 Hz, H-1'); 7.00 (d, 1H, $J_{3,7}$=1.0 Hz, H-3-benzofuryl); 7.26 (td, 1H, $J_{5,6}$=$J_{5,4}$=7.3 Hz, $J_{5,7}$=1.3 Hz, H-5-benzofuryl); 7.30 (bddd, 1H, $J_{6,7}$=8.1 Hz, $J_{6,5}$=7.2 Hz, $J_{6,4}$=1.6 Hz, H-6-benzofuryl); 7.62 (m, 1H, H-7-benzofuryl); 7.66 (m, 1H, H-4-benzofuryl); 8.01 (s, 1H, H-6); 8.31 (s, 1H, H-2). $^{13}$C NMR (125.7 MHz, DMSO-d$_6$): 39.91 ((CH$_3$)$_2$N); 61.71 (CH$_2$-5'); 70.74 (CH-3'); 74.21 (CH-2'); 85.46 (CH-4'); 87.14 (CH-1'); 101.82 (C-4a); 103.72 (CH-3-benzofuryl); 106.46 (C-5); 111.15 (CH-7-benzofuryl); 121.01 (CH-4-benzofuryl); 123.28 (CH-5-benzofuryl);

124.13 (CH-6); 124.22 (CH-6-benzofuryl); 129.06 (C-3a-benzofuryl); 151.00 (C-2); 152.03 (C-2-benzofuryl); 152.38 (C-7a); 154.30 (C-7a-benzofuryl); 159.83 (C-4). IR (ATR): v 1571, 1557, 1387, 1089, 1074, 1021, 985, 977, 819, 754, 614, 554 cm$^{-1}$. MS (ESI) m/z 411 (M+H), 433 (M+Na). HRMS (ESI) for $C_{21}H_{23}N_4O_5$ [M+H] calcd: 411.16630. found: 411.16492. Anal. Calcd for $C_{21}H_{22}N_4O_5$: C, 61.45; H, 5.40; N, 13.65. Found: C, 61.30; H, 5.35; N, 13.44.

EXAMPLE 31

4-Dimethylamino-5-ethynyl-7-(β-D-ribofuranosyl)-7H-pyrrolo[2,3-d]pyrimidine (4g)

An argon-purged mixture of 4h (420 mg, 1 mmol), $PdCl_2(PPh_3)_2$ (35 mg, 0.05 mmol), CuI (19 mg, 0.1 mmol), trimethylsilylacetylene (1.4 mL, 10 mmol) and triethylamine (0.5 mL) was stirred in DMF (2 mL) at rt for 6 h. The volatiles were removed in vacuo and the residue was several times co-evaporated with EtOH/toluene and loaded on silica by co-evaporation. Column chromatography (SiO$_2$, 0→2.5% MeOH in CHCl$_3$) afforded trimethylsilylethynyl derivative contaminated by triethylammonium iodide. This material was directly deprotected by treatment with $K_2CO_3$ (207 mg, 1.5 mmol) in MeOH (20 mL) at rt for 5 h, followed by evaporation of solvent. Reverse phase HPFC (C-18, 0→100% MeOH in water) furnished 4g (257 mg, 81% in two steps), which was crystallized from water/MeOH. Mp 143-145° C. [α]$_D$ −75.5 (c 0.261, DMSO). $^1$H NMR (500 MHz, DMSO-d$_6$): 3.27 (s, 6H, (CH$_3$)$_2$N); 3.55 (ddd, 1H, $J_{gem}$=11.9 Hz, $J_{5'a,OH}$=5.8 Hz, $J_{5'a,4'}$=3.6 Hz, H-5'a); 3.64 (ddd, 1H, $J_{gem}$=11.9 Hz, $J_{5'b,OH}$=5.1 Hz, $J_{5'b,4'}$=3.7 Hz, H-5'b); 3.90 (q, 1H, $J_{4',5'a}$=$J_{4',5'b}$=$J_{4',3'}$=3.6 Hz, H-4'); 4.09 (td, 1H, $J_{3',2'}$=$J_{3',OH}$=5.0 Hz, $J_{3',4'}$=3.4 Hz, H-3'); 4.21 (s, 1H, C≡CH); 4.35 (td, 1H, $J_{2',1'}$=$J_{2',OH}$=6.1 Hz, $J_{2',3'}$=5.1 Hz, H-2'); 5.14 (d, 1H, $J_{OH,3'}$=4.9 Hz, OH-3'); 5.17 (t, 1H, $J_{OH,5'a}$=$J_{OH,5'b}$=5.5 Hz, OH-5'); 5.36 (d, 1H, $J_{OH,2'}$=6.3 Hz, OH-2'); 6.12 (d, 1H, $J_{1',2'}$=6.0 Hz, H-1'); 7.98 (s, 1H, H-6); 8.21 (s, 1H, H-2). $^{13}$C NMR (125.7 MHz, DMSO-d$_6$): 41.00 ((CH$_3$)$_2$N); 61.58 (CH$_2$-5'); 70.59 (CH-3'); 74.24 (CH-2'); 79.87 (C≡CH); 82.82 (C≡CH); 85.34 (CH-4'); 87.12 (CH-1'); 95.50 (C-5); 102.91 (C-4a); 129.68 (CH-6); 151.16 (CH-2); 151.31 (C-7a); 158.47 (C-4). IR (ATR): v 2111, 1575, 1556, 1507, 1425, 1068, 1054, 1028, 646, 620 cm$^{-1}$. MS (ESI) m/z 319 (M+H), 341 (M+Na). HRMS (ESI) for $C_{15}H_{19}N_4O_4$ [M+H] calcd: 319.14008. found: 319.13917. Anal. Calcd for $C_{15}H_{18}N_4O_4H_2O$: C, 53.57; H, 5.99; N, 16.66. Found: C, 53.76; H, 5.88; N, 16.53.

EXAMPLE 32

Preparation of 5-Iodo-4-methyl-7-((β-D-ribofuranosyl)-7H-pyrrolo[2,3-d]pyrimidine (5h)

INTERMEDIATE 1

4-Chloro-7-(2,3,5-tri-O-benzoyl-β-D-ribofuranosyl)-7H-pyrrolo[2,3-d]pyrimidine (7)

To a solution of 4-chloro-5-iodo-7-(2,3,5-tri-O-benzoyl-β-D-ribofuranosyl)-7H-pyrrolo[2,3-d]pyrimidine 6 (ref.: Seela, F.; Ming, X., *Tetrahedron* 2007, 63, 9850-9861) (18.1 g, 25 mmol) in dry THF (100 mL) was dropwise added iPrMgCl.LiCl (1.3 M in THF, 20 mL, 26 mmol) at −10° C. and the solution was stirred at this temperature yet for 30 min. Then the reaction mixture was poured on the mixture of ice (250 g) and saturated aq NH$_4$Cl (200 mL) and was extracted with chloroform (500 mL, then 3×50 mL). Combined organic phases were dried over MgSO$_4$ and evaporated to dryness in vacuo affording 7 as colorless foam (15.4 g, quant). The product was used in next step without further purification. $^1$H NMR (400 MHz, DMSO-d$_6$): 4.68 (dd, 1H, $J_{gem}$=12.1 Hz, $J_{5'a,4'}$=5.0 Hz, H-5'a); 4.80 (dd, 1H, $J_{gem}$=12.1 Hz, $J_{5'b,4'}$=3.8 Hz, H-5b); 4.87 (ddd, 1H, $J_{4',3'}$=5.4, $J_{4',5'a}$=5.0 Hz, $J_{4',5'b}$=3.8 Hz, H-4'); 6.17 (dd, 1H, $J_{3',2'}$=6.2 Hz, $J_{3',4'}$=5.4 Hz, H-3'); 6.40 (dd, 1H, $J_{2',3'}$=6.2 Hz, $J_{2',1'}$=5.2 Hz, H-2'); 6.72 (d, 1H, $J_{1',2'}$=5.2 Hz, H-1'); 6.79 (d, 1H, $J_{5,6}$=3.8 Hz, H-5); 7.40-7.55 and 7.60-7.70 (2×m, 9H, H-p,m-Bz); 7.85, 7.96 and 7.99 (3×m, 3×2H, H-o-Bz); 8.04 (d, 1H, $J_{6,5}$=3.8 Hz, H-6); 8.58 (s, 1H, H-2). $^{13}$C NMR (101 MHz, DMSO-d$_6$): δ3.39 (CH$_2$-5'); 70.74 (CH-3'); 73.19 (CH-2'); 79.12 (CH-4'); 86.80 (CH-1'); 100.28 (CH-5); 117.83 (C-4a); 128.18, 128.54 (C-i-Bz); 128.66; 128.67 and 128.69 (CH-m-Bz); 129.19; 129.25 and 129.32 (CH-o-Bz); 129.70 (CH-6); 133.47, 133.82 and 133.90 (CH-p-Bz); 150.67 (CH-2); 150.84, 151.14 (C-4 and C-7a); 164.40, 164.66 and 165.35 (CO). IR (ATR): v 1725, 1590, 1553, 1456, 1265, 1203, 1094, 1071, 1027, 707 cm$^{-1}$. MS (ESI) m/z 598 (M+H), 620 (M+Na). HRMS (ESI) for $C_{32}H_{25}N_3O_7Cl$ [M+H] calcd: 598.13755. found: 598.13797.

INTERMEDIATE 2

4-Methyl-7-(2,3,5-tri-O-benzoyl-β-D-ribofuranosyl)-7H-pyrrolo[2,3-d]pyrimidine (8)

To an argon-purged mixture of 4-chloro-7-(2,3,5-tri-O-benzoyl-β-D-ribofuranosyl)-7H-pyrrolo[2,3-d]pyrimidine 7 (15.37 g, approx. 25 mmol), Pd(PPh$_3$)$_4$ (723 mg, 0.625 mmol) in dry THF (100 mL) was dropwise treated with trimethylaluminum (2 M in toluene, 25 mL, 50 mmol) at rt and the mixture was then stirred at 100° C. for 4 h. After cooling the mixture was pre-cooled in an ice bath and saturated aq NH$_4$Cl (200 mL) was added slowly with stirring. Caution methan gas evolution, excessive foaming! The mixture was then triturated with chloroform (600 mL) and filtered through Celite (to remove Al$_2$O$_3$). The aqueous phase was re-extacted with chloroform (3×50 mL). The combined organic phases were dried (MgSO$_4$) and evaporated, and the residue was loaded on silica by co-evaporation. Column chromatography (SiO$_2$, hexane-EtOAc, 2:1) afforded 8 (13.3 g, 92%) as a white foam. $^1$H NMR (500 MHz, DMSO-d$_6$): 2.64 (s, 3H, CH$_3$); 4.67 (dd, 1H, $J_{gem}$=12.1 Hz, $J_{5'a,4'}$=4.9 Hz, H-5'a); 4.78 (dd, 1H, $J_{gem}$=12.1 Hz, $J_{5'b,4'}$=3.7 Hz, H-5 b); 4.85 (td, 1H, $J_{4',3'}$=$J_{4',5'a}$=5.0 Hz, $J_{4',5'b}$=3.7 Hz, H-4'); 6.17 (dd, 1H, $J_{3',2'}$=6.1 Hz, $J_{3',4'}$=5.2 Hz, H-3'); 6.43 (bt, 1H, $J_{2',3'}$=$J_{2',1'}$=5.8 Hz, H-2'); 6.69 (d, 1H, $J_{1',2'}$=5.4 Hz, H-1'); 6.80 (d, 1H, $J_{5,6}$=3.8 Hz, H-5); 7.39-7.55 and 7.59-7.70 (2×m, 9H, H-p,m-Bz); 7.82 (d, 1H, $J_{6,5}$=3.8 Hz, H-6); 7.84, 7.96 and 8.01 (3×m, 3×2H, H-o-Bz); 8.60 (s, 1H, H-2). $^{13}$C NMR (125.7 MHz, DMSO-d$_6$): 21.36 (CH$_3$); 63.74 (CH$_2$-5'); 71.04 (CH-3'); 73.25 (CH-2'); 79.09 (CH-4'); 86.49 (CH-1'); 101.12 (C-5); 118.48 (C-4a); 127.54 (CH-6), 128.42 and 128.81 (C-i-Bz); 128.97, 128.98 and 128.99 (CH-m-Bz); 129.45 (C-i-Bz); 129.50 and 129.58 (CH-o-Bz); 133.77, 134.10 and 134.19 (CH-p-Bz); 150.31 (C-7a); 151.23 (CH-2); 159.75 (C-4); 164.66, 164.94 and 165.64 (CO). IR (ATR): v 1724, 1589, 1471, 1261, 1161, 1118, 1094, 1071, 1027, 706 cm$^1$. MS (ESI) m/z 578 (M+H), 600 (M+Na). HRMS (ESI) for $C_{33}H_{28}N_3O_7$ [M+H] calcd: 578.19218. found: 578.19238.

INTERMEDIATE 3

4-Methyl-7-(β-D-ribofuranosyl)-7H-pyrrolo[2,3-d]pyrimidine (9)

To a solution of compound 8 (8 g, 13.85 mmol) in MeOH (120 mL) was added sodium methoxide (25% w/w in MeOH, 2 mL, 8.75 mmol) and the mixture was stirred at rt for 5 h. Dowex 50 (Fr) was added in sufficient amount to fully bind the product, and disappearance of the latter in the solution was monitored by TLC (chloroform/MeOH, 9:1, Rf of 8 is 0.35, red spot after p-anisaldehyde staining). The resin was filtered off, washed with MeOH to remove methylbenzoate and eluted with aq. ammonia (27% w/w)/MeOH (1:2) mixture. Evaporation of combined eluates afforded 8 (3.58 g, 97%) as a colorless solid. Alternatively the reaction mixture was purified by co-evaporation with silica and subsequent column chromatography ($SiO_2$, 5% MeOH in chloroform) and crystallization from water. Mp 179-181° C. (lit. 175-176° C. (ref.: Wu, R.; Smidansky, E. D.; Oh, H. S.; Takhampunya, R.; Padmanabhan, R.; Cameron, C. E.; Peterson, B. R. Synthesis of a 6-Methyl-7-deaza Analogue of Adenosine That Potently Inhibits Replication of Polio and Dengue Viruses. *J. Med. Chem.* 2010, 53, 7958-7966)). $[\alpha]_D$ −65.9 (c 0.390, DMSO). $^1$H NMR (400 MHz, DMSO-$d_6$): 2.65 (s, 3H, $CH_3$); 3.54 (ddd, 1H, $J_{gem}$=11.9 Hz, $J_{5'a,OH}$=5.5 Hz, $J_{5'a,4'}$=4.0 Hz, H-5'a); 3.63 (ddd, 1H, $J_{gem}$=11.9 Hz, $J_{5'b,OH}$=5.1 Hz, $J_{5'b,4'}$=4.1 Hz, H-5'b); 3.91 (bq, 1H, $J_{4',5'a}$=$J_{4',5'b}$=$J_{4',3'}$=3.9 Hz, H-4'); 4.11 (td, 1H, $J_{3',2'}$=$J_{3',OH}$=4.9 Hz, $J_{3',4'}$=3.9 Hz, H-3'); 4.42 (td, 1H, $J_{2',1'}$=$J_{2',OH}$=6.2 Hz, $J_{2',3'}$=5.1 Hz, H-2'); 5.09 (t, 1H, $J_{OH,5'a}$=$J_{OH,5'b}$=5.5 Hz, OH-5'); 5.16 (d, 1H, $J_{OH,3'}$=4.7 Hz, OH-3'); 5.34 (d, 1H, $J_{OH,2'}$=6.2 Hz, OH-2'); 6.17 (d, 1H, $J_{1',2'}$=6.2 Hz, H-1'); 6.76 (d, $J_{5,6}$=3.7 Hz, 1H, H-5); 7.78 (d, $J_{6,5}$=3.7 Hz, 1H, H-6), 8.65 (s, 1H, H-2). $^{13}$C NMR, IR and MS data are as described (ref.: Wu, R.; Smidansky, E. D.; Oh, H. S.; Takhampunya, R.; Padmanabhan, R.; Cameron, C. E.; Peterson, B. R. Synthesis of a 6-Methyl-7-deaza Analogue of Adenosine That Potently Inhibits Replication of Polio and Dengue Viruses. *J. Med. Chem.* 2010, 53, 7958-7966). Anal. Calcd for $C_{12}H_{15}O_4N_3$: C, 54.33; H, 5.70; N, 15.84. Found: C, 54.03; H, 5.49; N, 15.60.

5-Iodo-4-methyl-7-(β-D-ribofuranosyl)-7H-pyrrolo[2,3-d]pyrimidine (5h)

To a stirred solution of 9 (796 mg, 3 mmol) in DMF (7 mL) was added dropwise N-iodosuccinimide (709 mg, 3.15 mmol) in DMF (3 mL) within 3 min. The mixture was stirred at rt for 16 h followed by addition of solid $Na_2SO_3$ (50 mg) and dilution with water (50 mL). This solution was directly separated (in portions according to column capacity) using reverse phase HPFC (C-18, 0→100% MeOH in water) to afford 5h (685 mg, 58%) as a white solid after crystallization from water. HPFC also recovered starting 9 (145 mg, 18%). Mp 187-188° C. $[\alpha]_D$ −58.3 (c 0.365, DMSO). $^1$H NMR (500 MHz, DMSO-$d_6$): 2.88 (s, 3H, $CH_3$); 3.55 (ddd, 1H, $J_{gem}$=11.9 Hz, $J_{5'a,OH}$=5.6 Hz, $J_{5'a,4'}$=3.9 Hz, H-5'a); 3.64 (ddd, 1H, $J_{gem}$=11.9 Hz, $J_{5'b,OH}$=5.3 Hz, $J_{5'b,4'}$=4.0 Hz, H-5'b); 3.91 (btd, 1H, $J_{4',5'a}$=$J_{4',5'b}$=3.9 Hz, $J_{4',3'}$=3.2 Hz, H-4'); 4.09 (td, 1H, $J_{3',2'}$=$J_{3',OH}$=5.0 Hz, $J_{3',4'}$=3.2 Hz, H-3'); 4.38 (td, 1H, $J_{2',1'}$=$J_{2',OH}$=6.3 Hz, $J_{2',3'}$=5.1 Hz, H-2'); 5.10 (t, 1H, $J_{OH,5'a}$=$J_{OH,5'b}$=5.5 Hz, OH-5'); 5.18 (d, 1H, $J_{OH,3'}$=4.8 Hz, OH-3'); 5.38 (d, 1H, $J_{OH,2'}$=6.4 Hz, OH-2'); 6.18 (d, 1H, $J_{1',2'}$=6.2 Hz, H-1'); 8.06 (s, 1H, H-6); 8.66 (s, 1H, H-2). $^{13}$C NMR (125.7 MHz, DMSO-$d_6$): 20.74 ($CH_3$); 54.05 (C-5); 61.61 ($CH_2$-5'); 70.67 (CH-3'); 74.30 (CH-2'); 85.52 (CH-4'); 86.66 (CH-1'); 118.04 (C-4a); 131.65 (CH-6); 150.27 (C-7a); 151.17 (CH-2); 159.76 (C-4). IR (ATR): ν 1584, 1562, 1347, 1335, 1207, 1122, 1078, 1059, 1031, 1000, 893 cm$^{-1}$. MS (ESI) m/z 392 (M+H), 414 (M+Na). HRMS (ESI) for $C_{12}H_{15}N_3O_4I$ [M+H] calcd: 392.01018. found: 392.01014. Anal. Calcd for $C_{12}H_{14}N_3O_4I$: C, 36.85; H, 3.61; N, 10.74. Found: C, 36.92; H, 3.58; N, 10.55.

EXAMPLE 33

5-Bromo-4-methyl-7-(β-D-ribofuranosyl)-7H-pyrrolo[2,3-d]pyrimidine (5i)

To a stirred solution of 9 (Intermediate 3 from Example 32) (1061 mg, 4 mmol) in DMF (10 mL) was added dropwise N-bromosuccinimide (748 mg, 4.2 mmol) in DMF (4 mL) within 3 min. The mixture was stirred at rt for 40 min followed by addition of solid $Na_2SO_3$ (50 mg) and dilution with water (66 mL). This solution was separated (in portions according to column capacity) using reverse-phase HPFC (C-18, 0→100% MeOH in water) to obtain a crude product, which after crystallization from iPrOH afforded 5i (913 mg, 66%) as white solid. Mp 188-189° C. $[\alpha]_D$ −61.1 (c 0.229, DMSO). $^1$H NMR (500 MHz, DMSO-$d_6$): 2.85 (s, 3H, $CH_3$); 3.55 (ddd, 1H, $J_{gem}$=11.9 Hz, $J_{5'a,OH}$=5.5 Hz, $J_{5'a,4'}$=4.0 Hz, H-5'a); 3.64 (ddd, 1H, $J_{gem}$=11.9 Hz, $J_{5'b,OH}$=5.2 Hz, $J_{5'b,4'}$=4.1 Hz, H-5 b); 3.91 (bq, 1H, $J_{4',5'a}$=$J_{4',5'b}$=$J_{4',3'}$=3.6 Hz, H-4'); 4.10 (td, 1H, $J_{3',2'}$=$J_{3',OH}$=4.9 Hz, $J_{3',4'}$=3.3 Hz, H-3'); 4.38 (td, 1H, $J_{2',1'}$=$J_{2',OH}$=6.2 Hz, $J_{2',3'}$=5.1 Hz, H-2'); 5.10 (t, 1H, $J_{OH,5'a}$=$J_{OH,5'b}$=5.4 Hz, OH-5'); 5.19 (d, 1H, $J_{OH,3'}$=4.8 Hz, OH-3'); 5.40 (d, 1H, $J_{OH,2'}$=6.3 Hz, OH-2'); 6.21 (d, 1H, $J_{1',2'}$=6.2 Hz, H-1'); 8.06 (s, 1H, H-6); 8.70 (s, 1H, H-2). $^{13}$C NMR (125.7 MHz, DMSO-$d_6$): 21.14 ($CH_3$); 61.58 ($CH_2$-5'); 70.64 (CH-3'); 74.33 (CH-2'); 85.54 (CH-4'); 86.66 (CH-1'); 88.18 (C-5); 115.68 (C-4a); 126.38 (CH-6); 149.75 (C-7a); 151.65 (CH-2); 159.54 (C-4). IR (ATR): ν 1593, 1563, 1345, 1211, 1119, 1092, 1058, 1032, 968, 921, 787 cm$^{-1}$. MS (ESI) m/z 344 (M+H), 366 (M+Na). HRMS (ESI) for $C_{12}H_{15}N_3O_4Br$ [M+H] calcd: 344.02405. found: 344.02407. Anal. Calcd for $C_{12}H_{14}N_3O_4Br$: C, 41.88; H, 4.10; N, 12.21. Found: C, 41.71; H, 4.08; N, 11.98.

EXAMPLE 34

5-(Furan-2-yl)-4-methyl-7-(β-D-ribofuranosyl)-7H-pyrrolo[2,3-d]pyrimidine (5a)

An argon-purged mixture of 5i (258 mg, 0.75 mmol), furan-2-boronic acid (126 mg, 1.125 mmol), $Na_2CO_3$ (239 mg, 2.25 mmol), Pd(OAc)$_2$ (8 mg, 35.6 μmol) and TPPTS (53 mg, 93 μmol) in water/MeCN (2:1, 5 mL) was stirred at 100° C. for 1 h. After cooling, the mixture was neutralized using aq. HCl (1 M), concentrated to dryness in vacuo and the residue was purified by reverse phase HPFC (C-18, 0→100% MeOH in water) to furnish 5a (207 mg, 83%) as an orange foam. $[\alpha]_D$ −75.3 (c 0.219, DMSO). $^1$H NMR (500 MHz, DMSO-$d_6$): 2.65 (s, 3H, $CH_3$); 3.57 (bdt, 1H, $J_{gem}$=11.9 Hz, $J_{5'a,OH}$=$J_{5'a,4'}$=4.5 Hz, H-5'a); 3.66 (bdt, 1H, $J_{gem}$=11.9 Hz, $J_{5'b,OH}$=$J_{5'b,4'}$=4.4 Hz, H-5'b); 3.94 (bq, 1H, $J_{4',5'a}$=$J_{4',5'b}$=$J_{4',3'}$=3.6 Hz, H-4'); 4.13 (m, 1H, H-3'); 4.45 (btd, 1H, $J_{2',1'}$=$J_{2',OH}$=6.2 Hz, $J_{2',3'}$=5.3 Hz, H-2'); 5.10 (bt, 1H, $J_{OH,5'a}$=$J_{OH,5'b}$=5.4 Hz, OH-5'); 5.20 (d, 1H, $J_{OH,3'}$=4.8 Hz, OH-3'); 5.41 (d, 1H, $J_{OH,2'}$=6.4 Hz, OH-2'); 6.26 (d, 1H, $J_{1',2'}$=6.1 Hz, H-1'); 6.62 (dd, 1H, $J_{4,3}$=3.3 Hz, $J_{4,5}$=1.9 Hz, H-4-furyl); 6.66 (dd, 1H, $J_{3,4}$=3.3 Hz, $J_{3,5}$=0.9 Hz, H-3-furyl); 7.80 (dd, 1H, $J_{5,4}$=1.9 Hz, $J_{5,3}$=0.9 Hz, H-5-furyl); 8.07 (s, 1H, H-6); 8.71 (s, 1H, H-2). $^{13}$C NMR (125.7 MHz, DMSO-d$_6$): 23.03 (CH$_3$); 61.63 (CH$_2$-5'); 70.71 (CH-3'); 74.31 (CH-2'); 85.50 (CH-4'); 86.79 (CH-1'); 106.79 (C-5); 108.50 (CH-3-furyl); 111.75 (CH-4-furyl); 115.36 (C-4a); 125.82 (CH-6); 142.93 (CH-5-furyl); 147.62 (C-2-furyl); 150.82 (C-7a); 151.38 (CH-2); 159.71 (C-4). IR (ATR): ν 1571, 1438, 1348, 1201, 1120, 1080, 1031, 968, 892, 792, 736, 637 cm$^{-1}$. MS (ESI) m/z 332 (M+H), 354 (M+Na). HRMS (ESI) for C$_{16}$H$_{18}$N$_3$O$_5$ [M+H] calcd: 332.12410. found: 332.12406. Anal. Calcd for C$_{16}$H$_{17}$N$_3$O$_5$.¾H$_2$O: C, 55.73; H, 5.41; N, 12.19. Found: C, 55.75; H, 5.37; N, 12.05.

EXAMPLE 35

5-(Furan-3-yl)-4-methyl-7-(β-D-ribofuranosyl)-7H-pyrrolo[2,3-d]pyrimidine (5b)

Compound 5b was prepared as described for 5a in Example 34 from 5i (258 mg, 0.75 mmol) and furan-3-boronic acid as a beige foam (195 mg, 78%). [α]$_D$ −62.1 (c 0.214, DMSO). $^1$H NMR (500 MHz, DMSO-d$_6$): 2.60 (s, 3H, CH$_3$); 3.55 (ddd, 1H, J$_{gem}$=11.9 Hz, J$_{5'a,OH}$=5.7 Hz, J$_{5'a,4'}$=4.0 Hz, H-5'a); 3.64 (ddd, 1H, J$_{gem}$=11.9 Hz, J$_{5'b,OH}$=5.3 Hz, J$_{5'b,4'}$=4.0 Hz, H-5'b); 3.93 (btd, 1H, J$_{4',5'a}$=J$_{4',5'b}$=4.0 Hz, J$_{4',3'}$=3.3 Hz, H-4'); 4.12 (btd, 1H, J$_{3',2'}$=J$_{3',OH}$=5.0 Hz, J$_{3',4'}$=3.3 Hz, H-3'); 4.44 (td, 1H, J$_{2',1'}$=J$_{2',OH}$=6.3 Hz, J$_{2',3'}$=5.1 Hz, H-2'); 5.08 (t, 1H, J$_{OH,5'a}$=J$_{OH,5'b}$=5.5 Hz, OH-5'); 5.18 (d, 1H, J$_{OH,3'}$=4.9 Hz, OH-3'); 5.38 (d, 1H, J$_{OH,2'}$=6.4 Hz, OH-2'); 6.25 (d, 1H, J$_{1',2'}$=6.2 Hz, H-1'); 6.77 (dd, 1H, J$_{4,5}$=1.8 Hz, J$_{4,2}$=0.9 Hz, H-4-furyl); 7.80 (dd, 1H, J$_{5,4}$=J$_{5,2}$=1.7 Hz, H-5-furyl); 7.82 (s, 1H, H-6); 7.88 (dd, 1H, J$_{2,5}$=1.6 Hz, J$_{2,4}$=0.9 Hz, H-2-furyl); 8.67 (s, 1H, H-2). $^{13}$C NMR (125.7 MHz, DMSO-d$_6$): 22.79 (CH$_3$); 61.74 (CH$_2$-5'); 70.76 (CH-3'); 74.19 (CH-2'); 85.39 (CH-4'); 86.64 (CH-1'); 107.29 (C-5); 112.97 (CH-4-furyl); 116.30 (C-4a); 118.42 (C-3-furyl); 124.96 (CH-6); 140.74 (CH-2-furyl); 143.67 (CH-5-furyl); 150.91 (C-7a); 151.07 (CH-2); 159.58 (C-4). IR (ATR): ν 1572, 1447, 1205, 1120, 1080, 1042, 988, 897, 874, 789, 639, 600 cm$^{-1}$. MS (ESI) m/z 332 (M+H), 354 (M+Na). HRMS (ESI) for C$_{16}$H$_{18}$N$_3$O$_5$ [M+H] calcd: 332.12410. found: 332.12402. Anal. Calcd for C$_{16}$H$_{17}$N$_3$O$_5$.H$_2$O: C, 55.01; H, 5.48; N, 12.03. Found: C, 55.11; H, 5.35; N, 11.87.

EXAMPLE 36

4-Methyl-7-(β-D-ribofuranosyl)-5-(thiophen-2-yl)-7H-pyrrolo[2,3-d]pyrimidine (5c)

Compound 5c was prepared as described for 5a in Example 34 from 5i (258 mg, 0.75 mmol) and thiophene-2-boronic acid as a creamy solid (202 mg, 78%), which was crystallized from water. Mp 110-111° C. [α]$_D$ −68.8 (c 0.356, DMSO). $^1$H NMR (500 MHz, DMSO-d$_6$): 2.54 (s, 3H, CH$_3$); 3.56 (ddd, 1H, J$_{gem}$=11.9 Hz, J$_{5'a,OH}$=5.7 Hz, J$_{5'a,4'}$=3.8 Hz, H-5'a); 3.65 (ddd, 1H, J$_{gem}$=11.9 Hz, J$_{5'b,OH}$=5.2 Hz, J$_{5'b,4'}$=3.9 Hz, H-5'b); 3.94 (bq, 1H, J$_{4',5'a}$=J$_{4',5'b}$=J$_{4',3'}$=3.6 Hz, H-4'); 4.12 (td, 1H, J$_{3',2'}$=J$_{3',OH}$=5.0 Hz, J$_{3',4'}$=3.2 Hz, H-3'); 4.45 (td, 1H, J$_{2',1'}$=J$_{2',OH}$=6.3 Hz, J$_{2',3'}$=5.1 Hz, H-2'); 5.09 (t, 1H, J$_{OH,5'a}$=J$_{OH,5'b}$=5.4 Hz, OH-5'); 5.19 (d, 1H, J$_{OH,3'}$=4.8 Hz, OH-3'); 5.41 (d, 1H, J$_{OH,2'}$=6.4 Hz, OH-2'); 6.26 (d, 1H, J$_{1',2'}$=6.2 Hz, H-1'); 7.18 (dd, 1H, J$_{4,5}$=5.2 Hz, J$_{4,3}$=3.5 Hz, H-4-thienyl); 7.23 (dd, 1H, J$_{3,4}$=3.5 Hz, J$_{3,5}$=1.2 Hz, H-3-thienyl); 7.61 (dd, 1H, J$_{5,4}$=5.2 Hz, J$_{5,3}$=1.2 Hz, H-5-thienyl); 7.96 (s, 1H, H-6); 8.71 (s, 1H, H-2). $^{13}$C NMR (125.7 MHz, DMSO-d$_6$): 22.68 (CH$_3$); 61.64 (CH$_2$-5'); 70.73 (CH-3'); 74.28 (CH-2'); 85.50 (CH-4'); 86.72 (CH-1'); 109.13 (C-5); 116.26 (C-4a); 126.22 (CH-6); 126.38 (CH-5-thienyl); 127.86 (CH-4-thienyl); 128.36 (CH-3-thienyl); 134.86 (C-2-thienyl); 150.66 (C-7a); 151.29 (CH-2); 159.63 (C-4). IR (ATR): ν 1578, 1557, 1457, 1427, 1341, 1192, 1120, 1091, 1040, 899, 835, 694 cm$^{-1}$. MS (ESI) m/z 348 (M+H), 370 (M+Na). HRMS (ESI) for C$_{16}$H$_{17}$N$_3$O$_4$SNa [M+Na] calcd: 370.08320. found: 370.08319. Anal. Calcd for C$_{16}$H$_{17}$N$_3$O$_4$S.0.4H$_2$O: C, 54.20; H, 5.06; N, 11.85. Found: C, 54.30; H, 4.96; N, 11.72.

EXAMPLE 37

4-Methyl-7-(β-D-ribofuranosyl)-5-(thiophen-3-yl)-7H-pyrrolo[2,3-d]pyrimidine (5d)

Compound 5d was prepared as described for 5a in Example 34 from 5i (258 mg, 0.75 mmol) and thiophene-3-boronic acid as a beige foam (214 mg, 82%). [α]$_D$ −67.7 (c 0.217, DMSO). $^1$H NMR (500 MHz, DMSO-d$_6$): 2.52 (s, 3H, CH$_3$); 3.55 (bddd, 1H, J$_{gem}$=11.9 Hz, J$_{5'a,OH}$=5.5 Hz, J$_{5'a,4'}$=3.9 Hz, H-5'a); 3.64 (bddd, 1H, J$_{gem}$=11.9 Hz, J$_{5'b,OH}$=5.2 Hz, J$_{5'b,4'}$=3.9 Hz, H-5'b); 3.93 (td, 1H, J$_{4',5'a}$=J$_{4',5'b}$=3.9 Hz, J$_{4',3'}$=3.3 Hz, H-4'); 4.12 (btd, 1H, J$_{3',2'}$=J$_{3',OH}$=4.8 Hz, J$_{3',4'}$=3.3 Hz, H-3'); 4.45 (td, 1H, J$_{2',1'}$=J$_{2',OH}$=6.3 Hz, J$_{2',3'}$=5.1 Hz, H-2'); 5.07 (t, 1H, J$_{OH,5'a}$=J$_{OH,5'b}$=5.4 Hz, OH-5'); 5.18 (d, 1H, J$_{OH,3'}$=4.8 Hz, OH-3'); 5.38 (d, 1H, J$_{OH,2'}$=6.4 Hz, OH-2'); 6.26 (d, 1H, J$_{1',2'}$=6.2 Hz, H-1'); 7.31 (dd, 1H, J$_{4,5}$=4.9 Hz, J$_{4,2}$=1.3 Hz, H-4-thienyl); 7.59 (dd, 1H, J$_{2,5}$=3.0 Hz, J$_{2,4}$=1.3 Hz, H-2-thienyl); 7.67 (dd, 1H, J$_{5,4}$=4.9 Hz, J$_{5,2}$=3.0 Hz, H-5-thienyl); 7.85 (s, 1H, H-6); 8.68 (s, 1H, H-2). $^{13}$C NMR (125.7 MHz, DMSO-d$_6$): 22.84 (CH$_3$); 61.72 (CH$_2$-5'); 70.76 (CH-3'); 74.20 (CH-2'); 85.40 (CH-4'); 86.66 (CH-1'); 111.89 (C-5); 116.23 (C-4a); 123.76 (CH-2-thienyl); 124.99 (CH-6); 126.28 (CH-5-thienyl); 129.95 (CH-4-thienyl); 134.40 (C-3-thienyl); 150.70 C-7a); 151.00 (CH-2); 159.55 (C-4). IR (ATR): ν 1578, 1559, 1473, 1453, 1343, 1120, 1081, 1047, 983, 860, 785, 640 cm$^{-1}$. MS (ESI) m/z 348 (M+H), 370 (M+Na). HRMS (ESI) for C$_{16}$H$_{18}$N$_3$O$_4$S [M+H] calcd: 348.10125. found: 348.10122. Anal. Calcd for C$_{16}$H$_{17}$N$_3$O$_4$S. ¾H$_2$O: C, 53.25; H, 5.17; N, 11.64. Found: C, 53.34; H, 5.18; N, 11.29.

EXAMPLE 38

4-Methyl-5-phenyl-7-(β-D-ribofuranosyl)-7H-pyrrolo[2,3-d]pyrimidine (5e)

Compound 5e was prepared as described for 5a in Example 34 from 5i (258 mg, 0.75 mmol) and phenylboronic acid as a white foam (183 mg, 71%). [α]$_D$ −68.4 (c 0.209, DMSO). $^1$H NMR (500 MHz, DMSO-d$_6$): 2.46 (s, 3H, CH$_3$); 3.55 (ddd, 1H, J$_{gem}$=11.9 Hz, J$_{5'a,OH}$=5.8 Hz, J$_{5'a,4'}$=3.9 Hz, H-5'a); 3.64 (ddd, 1H, J$_{gem}$=11.9 Hz, J$_{5'b,OH}$=5.3 Hz, J$_{5'b,4'}$=3.9 Hz, H-5'b); 3.93 (td, 1H, J$_{4',5'a}$=J$_{4',5'b}$=3.9 Hz, J$_{4',3'}$=3.3 Hz, H-4'); 4.13 (td, 1H, J$_{3',2'}$=J$_{3',OH}$=5.0 Hz, J$_{3',4'}$=3.3 Hz, H-3'); 4.48 (td, 1H, J$_{2',1'}$=J$_{2',OH}$=6.3 Hz, J$_{2',3'}$=5.1 Hz, H-2'); 5.07 (t, 1H, J$_{OH,5'a}$=J$_{OH,5'b}$=5.5 Hz, OH-5'); 5.18 (d, 1H, J$_{OH,3'}$=4.9 Hz, OH-3'); 5.39 (d, 1H, J$_{OH,2'}$=6.4 Hz, OH-2'); 6.28 (d, 1H, J$_{1',2'}$=6.2 Hz, H-1'); 7.39 (m, 1H, H-p-Ph); 7.47 (m, 2H, H-m-Ph); 7.51 (m, 2H, H-o-Ph); 7.85 (s, 1H, H-6); 8.69 (s, 1H, H-2). $^{13}$C NMR (125.7 MHz, DMSO-d$_6$): 23.08 (CH$_3$); 61.71 (CH$_2$-5'); 70.77 (CH-3'); 74.20 (CH-2'); 85.40 (CH-4'); 86.73 (CH-1'); 116.04 (C-4a); 176.20 (C-5); 124.93 (CH-6); 127.35 (CH-p-Ph); 128.47 (CH-m-Ph); 130.03 (CH-o-Ph); 134.47 (C-i-Ph); 150.86 (C-7a); 150.99 (CH-2);

159.46 (C-4). IR (ATR): ν 1580, 1448, 1202, 1120, 1080, 1046, 1032, 764, 703, 654, 591 cm$^{-1}$. MS (ESI) m/z 342 (M+H), 364 (M+Na). HRMS (ESI) for C$_{18}$H$_{20}$N$_{3}$O$_{4}$ [M+H] calcd: 342.14483. found: 342.14376. Anal. Calcd for C$_{18}$H$_{19}$N$_{3}$O$_{4}$.0.7H$_{2}$O: C, 61.08; H, 5.81; N, 11.87. Found: C, 61.27; H, 5.86; N, 11.69.

EXAMPLE 39

5-(Benzofuran-2-yl)-4-methyl-7-(β-D-ribofuranosyl)-7H-pyrrolo[2,3-d]pyrimidine (5f)

An argon-purged mixture of 5i (258 mg, 0.75 mmol), benzofuran-2-boronic acid (182 mg, 1.125 mmol), Na$_{2}$CO$_{3}$ (239 mg, 2.25 mmol), Pd(OAc)$_{2}$ (8 mg, 0.036 mmol) and TPPTS (53 mg, 0.093 mmol) in water/MeCN (2:1, 5 mL) was stirred at 100° C. for 3 h. After cooling the solidified mixture was suspended by addition of water/MeOH (1:1, 25 mL) and shaking. The pH of the mixture was adjusted to 5 using aq HCl (1 M), the resulting fine precipitate was filtered off through Celite layer, washed with water and mother liquor was saved. After drying the precipitate (on Celite) was loaded on silica by co-evaporation from chloroform/MeOH solution and chromatographed (SiO$_{2}$, 3% MeOH in chloroform) to give 5f (178 mg, 62%) as a white solid. Mother liquor was concentrated to dryness and the residue was purified by reverse phase HPFC (C-18, 0→100% MeOH in water) to afford additional 5f (50 mg, 17%). Total yield of 5f was 79%. Combined product was crystallized from MeOH. Mp 185-187° C. [α]$_D$ −88.0 (c 0.259, DMSO). $^1$H NMR (500 MHz, DMSO-d$_6$): 2.78 (s, 3H, CH$_3$); 3.59 (ddd, 1H, J$_{gem}$=11.9 Hz, J$_{5'a,OH}$=5.7 Hz, J$_{5'a,4'}$=3.9 Hz, H-5'a); 3.69 (ddd, 1H, J$_{gem}$=11.9 Hz, J$_{5'b,OH}$=5.3 Hz, J$_{5'b,4'}$=3.9 Hz, H-5'b); 3.97 (q, 1H, J$_{4',5'a}$=J$_{4',5'b}$=J$_{4',3'}$=3.6 Hz, H-4'); 4.16 (td, 1H, J$_{3',2'}$=J$_{3',OH}$=5.0 Hz, J$_{3',4'}$=3.3 Hz, H-3'); 4.49 (td, 1H, J$_{2',1'}$=J$_{2',OH}$=6.2 Hz, J$_{2',3'}$=5.1 Hz, H-2'); 5.13 (t, 1H, J$_{OH,5'a}$=J$_{OH,5'b}$=5.5 Hz, OH-5'); 5.23 (d, 1H, J$_{OH,3'}$=4.9 Hz, OH-3'); 5.46 (d, 1H, J$_{OH,2'}$=6.3 Hz, OH-2'); 6.30 (d, 1H, J$_{1',2'}$=6.1 Hz, H-1'); 7.16 (d, 1H, J$_{3,7}$=1.0 Hz, H-3-benzofuryl); 7.28 (btd, 1H, J$_{5,6}$=J$_{5,4}$=7.4 Hz, J$_{5,7}$=1.1 Hz, H-5-benzofuryl); 7.32 (bddd, 1H, J$_{6,7}$=8.1 Hz, J$_{6,5}$=7.3 Hz, J$_{6,4}$=1.5 Hz, H-6-benzofuryl); 7.64 (bdq, 1H, J$_{7,6}$=8.1 Hz, J$_{7,5}$=J$_{7,4}$=J$_{7,3}$=1.0 Hz, H-7-benzofuryl); 7.68 (ddd, 1H, J$_{4,5}$=7.6 Hz, J$_{4,6}$=1.5 Hz, J$_{4,7}$=0.7 Hz, H-4-benzofuryl); 8.33 (s, 1H, H-6); 8.76 (s, 1H, H-2). $^{13}$C NMR (125.7 MHz, DMSO-d$_6$): 23.56 (CH$_3$); 61.60 (CH$_2$-5'); 70.67 (CH-3'); 74.39 (CH-2'); 85.57 (CH-4'); 86.94 (CH-1'); 104.46 (CH-3-benzofuryl); 106.30 (C-5); 111.15 (CH-7-benzofuryl); 115.21 (C-4a); 121.07 (CH-4-benzofuryl); 123.37 (CH-6-benzofuryl); 124.37 (CH-5-benzofuryl); 127.18 (CH-6); 128.93 (C-3a-benzofuryl); 150.49 (C-2-benzofuryl); 151.06 (C-7a); 151.61 (CH-2); 154.36 (C-7a-benzofuryl); 159.95 (C-4). IR (ATR): ν 1561, 1459, 1438, 1268, 1207, 1129, 1102, 1063, 1030, 970, 904, 788, 739, 614 cm$^{-1}$. MS (ESI) m/z 382 (M+H), 404 (M+Na). HRMS (ESI) for C$_{20}$H$_{20}$N$_{3}$O$_{5}$ [M+H] calcd: 382.13975. found: 382.13857. Anal. Calcd for C$_{20}$H$_{19}$N$_{3}$O$_{5}$: C, 62.99; H, 5.02; N, 11.02. Found: C, 63.09; H, 5.09; N, 10.72.

EXAMPLE 40

5-Ethynyl-4-methyl-7-(β-D-ribofuranosyl)-7H-pyrrolo[2,3-d]pyrimidine (5g)

An argon-purged mixture of 5h (391 mg, 1 mmol), PdCl$_2$(PPh$_3$)$_2$ (35 mg, 0.05 mmol), CuI (19 mg, 0.1 mmol), trimethylsilylacetylene (1.4 mL, 10 mmol) and triethylamine (0.5 mL) was stirred in DMF (2 mL) at rt for 10 h. The volatiles were removed in vacuo and the residue was several times co-evaporated with EtOH/toluene and loaded on silica by co-evaporation. Column chromatography (SiO$_2$, 0→2.5% MeOH in CHCl$_3$) afforded trimethylsilylethynyl derivative contaminated by triethylammonium iodide. This material was directly deprotected by treatment with K$_2$CO$_3$ (207 mg, 1.5 mmol) in MeOH (5 mL) at rt for 3 h, followed by evaporation. Reverse phase HPFC (C-18, 0→100% MeOH in water) furnished 5g (233 mg, 81% in two steps), which was crystallized from MeOH. Mp 96-106° C. [α]$_D$ −74.6 (c 0.339, DMSO). $^1$H NMR (500 MHz, DMSO-d$_6$): 2.83 (s, 3H, CH$_3$); 3.56 (ddd, 1H, J$_{gem}$=11.9 Hz, J$_{5'a,OH}$=5.6 Hz, J$_{5'a,4'}$=3.9 Hz, H-5'a); 3.65 (ddd, 1H, J$_{gem}$=11.9 Hz, J$_{5'b,OH}$=5.2 Hz, J$_{5'b,4'}$=3.9 Hz, H-5'b); 3.93 (btd, 1H, J$_{4',5'a}$=J$_{4',5'b}$=3.9 Hz, J$_{4',3'}$=3.5 Hz, H-4'); 4.11 (m, 1H, H-3'); 4.31 (s, 1H, C≡CH); 4.39 (bq, 1H, J$_{2',1'}$=J$_{2',OH}$=J$_{2',3'}$=5.1 Hz, H-2'); 5.12 (t, 1H, J$_{OH,5'a}$=J$_{OH,5'b}$=5.4 Hz, OH-5'); 5.20 (bd, 1H, J$_{OH,3'}$=4.5 Hz, OH-3'); 5.42 (bd, 1H, J$_{OH,2'}$=5.3 Hz, OH-2'); 6.18 (d, 1H, J$_{1',2'}$=6.0 Hz, H-1'); 8.20 (s, 1H, H-6); 8.70 (s, 1H, H-2). $^{13}$C NMR (125.7 MHz, DMSO-d$_6$): 20.86 (CH$_3$); 61.54 (CH$_2$-5'); 70.63 (CH-3'); 74.43 (CH-2'); 77.43 (C≡CH); 83.16 (C≡CH); 85.57 (CH-4'); 86.99 (CH-1'); 95.50 (C-5); 117.19 (C-4a); 131.76 (CH-6); 149.89 (C-7a); 152.00 (CH-2); 160.31 (C-4). IR (ATR): ν 1590, 1578, 1435, 1383, 1194, 1104, 1087, 1050, 1026, 984, 941, 702, 628, 617 cm$^{-1}$. MS (ESI) m/z 290 (M+H), 312 (M+Na). HRMS (ESI) for C$_{14}$H$_{16}$N$_{3}$O$_{4}$ [M+H] calcd: 290.11353. found: 290.11261. Anal. Calcd for C$_{14}$H$_{15}$N$_{3}$O$_{4}$.0.8H$_{2}$O.0.55CH$_{3}$OH: C, 54.39; H, 5.90; N, 13.08. Found: C, 54.49; H, 5.64; N, 12.83.

EXAMPLE 41

Cytostatic/Cytotoxic Testings
Cytostatic/Cytotoxic MTT Assay

Unless otherwise stated, all cells were purchased from the American Tissue Culture Collection (ATCC). The CCRF-CEM line is derived from T lymphoblastic leukemia, evincing high chemosenzitivity, K562 represent cells from a acute myeloid leukemia patient sample with bcr-abl translocation, HCT116 is colorectal tumor cell line and its p53 gene knock-down counterpart (HCT116p53−/−, Horizon Discovery, UK) is a model of human cancers with p53 inactivation frequently associated with poor prognosis, A549 cell line is lung adenocarcinoma. The daunorubicin resistant subline of CCRF-CEM cells (CEM-DNR bulk) and paclitaxel resistant subline K562-TAX were selected in our laboratory by cultivation of maternal cell lines in increasing concentrations of daunorubicine or paclitaxel, respectively. The CEM-DNR cells overexpress mrp-1 and mdr-1 genes, while K562-TAX cells overexpress mdr-1 only. Both proteins belong to the family of ABC transporters and are involved in the primary and/or acquired multidrug resistance phenomenon (ref.: Gottesman, M. M.; Fojo, T.; Bates, S. E. Multidrug resistance in cancer: role of ATP-dependent transporters. Nat. Rev. Cancer. 2002, 2, 48-58. (b) Noskova, V.; Dzubak, P.; Kuzmina, G.; Ludkova, A.; Stehlik, D.; Trojanec, R.; Janostakova, A.; Korinkova, G.; Mihal, V.; Hajduch, M. In vitro chemoresistance profile and expression/function of MDR associated proteins in resistant cell lines derived from CCRF-CEM, K562, A549 and MDA MB 231 parental cells. Neoplasma 2002, 49, 418-425). Non-malignant MRC-5 and BJ cells, derived from normal human fibroblasts, were used as controls. The cells were maintained in Nunc/Corning 80 cm$^2$ plastic tissue culture flasks and cultured in cell culture medium (DMEM/RPMI 1640 with 5 g/L glucose, 2 mM glutamine, 100 U/mL penicillin, 100 g/mL streptomycin, 10% fetal calf serum, and NaHCO$_3$). Cell suspensions were prepared and diluted according to the particular cell type and the expected target cell density (25,000-30,000 cells/well based on cell growth characteristics). Cells were added by pipette (80 L) into 96-well microtiter plates. Inoculates were allowed a pre-incubation period of 24 h at 37° C. and 5% CO$_2$ for stabilization. Four-fold dilutions, in 20-L aliquots, of the intended test concentration were added to the microtiter plate walls at time zero. All test compound concentrations were examined in duplicate. Incubation of the cells with the test compounds lasted for 72 h at 37° C., in a 5% CO$_2$ atmosphere at 100% humidity. At the end of the incubation period, the cells were assayed using MTT. Aliquots (10 L) of the MTT stock solution (5 mg/ml) were pipetted into each well and incubated for another 1-4 h. After this incubation period the formazan produced was dissolved by addition of 100 L/well of 10% aq SDS (pH 5.5), followed by a further incubation at 37° C. overnight. The optical density was measured at 540 nm. The IC$_{50}$ value, the drug concentration inhibiting the cell growth by 50%, was calculated from appropriate dose-response curves.

XTT Cytotoxicity Assay

HL-60, Hela S3 and HepG2 cell lines (ATCC) were grown in RPMI-1640 or DMEM medium supplemented with 10% fetal calf serum, 200 mg/mL of streptomycin, 200 U/mL of penicillin G and 4 mM glutamine in a humidified atmosphere containing 5% CO$_2$ at 37° C. Sensitivity of these cell lines to the synthesized compounds was assessed with the use of XTT cell proliferation kit II (Roche Diagnostics GmbH, Mannheim, Germany) according to the manufacturer's instructions. Briefly, cells were seeded in a 96-well plate at a density of 10,000 cells per well (90 µL). After 24 h, 10 µL of the tested compounds were added to the culture media at desired concentration range and incubated for 72 h. After that 50 µL of the XTT solution was added (1 mg/mL XTT+0.383 mg/mL N-methyl dibenzopyrazine methyl sulfate). The absorbance was recorded at 495 nm following a 2 h-incubation with the dye. IC$_{50}$ values were determined by non-linear regression method using GraphPad Prism version 5.00 for Windows (GraphPad Software, La Jolla, Calif., USA).

Flow Cytometric Analysis

Cell Cycle and Apoptosis Analysis.

Suspensions of CCRF-CEM cells (ATCC), seeded at a density of 1.10$^6$ cells/ml in 6-well panels, were cultivated with vehicle, the 1× or 5×IC$_{50}$ of tested compound in a humidified CO$_2$ incubator at 37° C. in RPMI 1640 cell culture medium containing 10% fetal calf serum, 2 mM glutamine, 100 U/mL penicillin, and 100 µg/mL streptomycin for 24 hours. After the incubation period, cells were then washed with cold 1×PBS and fixed in 70% ethanol added dropwise and stored overnight at −20° C. Afterwards, cells were washed in hypotonic citrate buffer, treated with RNase (50 µg/mL) and stained with propidium iodide. Flow cytometry using a 488 nm single-beam laser (Becton Dickinson) was used for measurement. The data were analyzed according to the program ModFitLT (Verity), and apoptosis was expressed as the percentage of cells with a propidium content lower than that in the G0/G1 population. Half of the sample was used for pH3$^{ser10}$ antibody (Sigma) labeling and subsequent flow cytometry analysis of mitotic cells.

BrdU Incorporation Analysis.

Cells were cultured as for cell cycle analysis. Before harvesting, they were pulse-labelled with 10 M 5-bromo-2'-deoxyuridine (BrdU) for 30 min. The cells were trypsinized, fixed with ice-cold 70% ethanol, incubated on ice for 30 min, washed with PBS, and resuspended in 2 M HCl for 30 min at room temperature to denature their DNA. Following neutralization with 0.1 M Na$_2$B$_4$O$_7$, the cells were washed with PBS containing 0.5% Tween-20 and 1% BSA. They were then stained with primary anti-BrdU antibody (Exbio) for 30 min at room temperature in the dark. Cells were than washed with PBS and stained with secondary anti-mouse-FITC antibody (Sigma). The cells were then washed with PBS, incubated with propidium iodide (0.1 mg/mL) and RNAse A (0.5 mg/mL) for 1 h at room temperature in the dark, and finally analyzed by flow cytometry using a 488 nm single-beam laser (FACSCalibur, Becton Dickinson).

BrU Incorporation Analysis.

Cells were cultured and treated as for cell cycle analysis. Before harvesting, they were pulse-labelled with 1 mM 5-bromouridine (BrU) for 30 min. The cells were fixed in 1% buffered paraformaldehyde with 0.05% of NP-40, incubated in room temperature for 15 min and than in the fridge overnight. They were then washed in 1% glycin in PBS, washed in PBS and stained with primary anti-BrdU antibody crossreacting to BrU (Exbio) for 30 min at room temperature in the dark. Cells were than washed with PBS and stained with secondary anti-mouse-FITC antibody (Sigma). Following the staining the cells are washed with PBS and fixed with 1% PBS buffered paraformaldehyde with 0.05% of NP-40. The cells were then washed with PBS, incubated with propidium iodide (0.1 mg/mL) and RNAse A (0.5 mg/mL) for 1 h at room temperature in the dark, and finally analyzed by flow cytometry using a 488 nm single-beam laser (FACSCalibur, Becton Dickinson).

Results of Biological Testings

For biological testings following reference compounds RC1-5 were used:

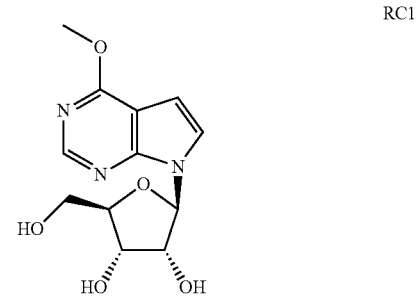

RC1

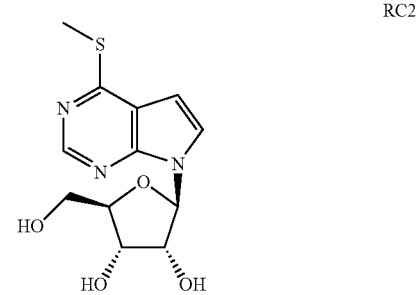

RC2

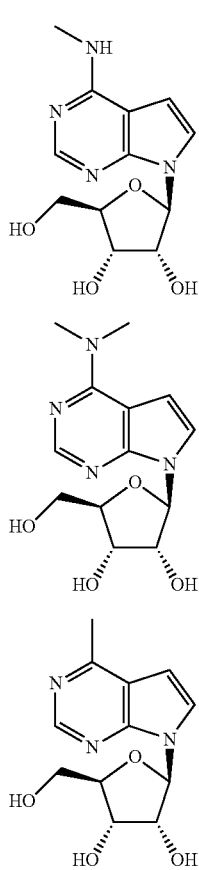

RC3

RC4

RC5

Compounds RC1-4 were reported (ref.: Gerster, J. F.; Carpenter, B.; Robins, R. K.; Townsend, L. B. Pyrrolopyrimidine Nucleosides. I. The Synthesis of 4-Substituted 7-(-β-D-Ribofuranosyl)pyrrolo[2,3-d]pyrimidines from Tubercidin. J. Med. Chem. 1967, 10, 326-331) and compound RC5 is also known (Wu, R.; Smidansky, E. D.; Oh, H. S.; Takhampunya, R.; Padmanabhan, R.; Cameron, C. E.; Peterson, B. R. Synthesis of a 6-Methyl-7-deaza Analogue of Adenosine That Potently Inhibits Replication of Polio and Dengue Viruses. J. Med. Chem. 2010, 53, 7958-7966) Compound 1h was described previously and in present testing was covered only as reference compound (ref.: Seela, F.; Ming, X. 7-Functionalized 7-deazapurine β-D and β-L-ribonucleosides related to tubercidin and 7-deazainosine: glycosylation of pyrrolo[2,3-d]pyrimidines with 1-O-acetyl-2,3,5-tri-O-benzoyl-β-D or β-L-ribofuranose. Tetrahedron 2007, 63, 9850-9861; Zhang, L.; Zhang, Y.; Li, X.; Zhang, L., Bioorg. Med. Chem. 2002, 10, 907-912).

Cytotoxic/Cytostatic Activity

In vitro cytotoxic/cytostatic activity final nucleosides 1-5 was initially evaluated against six cell lines derived from human solid tumors including lung (A549 cells) and colon (HCT116 and HCT116p53−/−) carcinomas, as well as leukemia cell lines (CCRF-CEM, CEM-DNR, K562 and K562-TAX) and, for comparison, non-malignant BJ and MRC-5 fibroblasts. Concentrations inhibiting the cell growth by 50% ($IC_{50}$) were determined using a quantitative metabolic staining with 3-(4,5-dimethylthiazol-2-yl)-2,5-diphenyltetrazolium bromide (MTT) (ref.: Denizot, F.; Lang, R. Rapid colorimetric assay for cell growth and survival: Modifications to the tetrazolium dye procedure giving improved sensitivity and reliability. J. Immunol. Meth. 1986, 89, 271-277) following a 3-day treatment.

In addition, the anti-proliferative effect was tested against a human T-lymphoblastic leukemia line CCRF-CEM, promyelocytic leukemia HL-60 and cervical carcinoma HeLa S3 growing in liquid suspension. Cell viability was determined following a 3-day incubation using 2,3-bis-(2-methoxy-4-nitro-5-sulfophenyl)-2H-tetrazolium-5-carboxanilide (XTT) assay (ref.: Scudiero, D. A.; Shoemaker, R. H.; Paull, K. D.; Monks, A.; Tierney, S.; Nofziger, T. H.; Currens, M. J.; Seniff, D.; Boyd M. R. Evaluation of a Soluble Tetrazolium/Formazan Assay for Cell Growth and Drug Sensitivity in Culture Using Human and Other Tumor Cell Lines. Cancer Res. 1988, 48, 4827-4833).

Table 1 summarizes the cytotoxic activities of 1-5. In the 6-substituted series, the 7-(2-furyl) derivatives 1a, 2a, 3a, and 5a were the most potent, showing low nanomolar cytostatic effects, whereas the $IC_{50}$ values of the bulkier 6-dimethylamino derivative 4a were in micromolar range. These derivatives, however, were also the most cytotoxic to fibroblasts suggesting a non-specific cytotoxic effect. On the other hand, analogous 7-(3-furyl)-, 7-(2-thienyl)- and 7-(3-thienyl)-derivatives 1-5b, 1-5c and 1-5d were less active or inactive. The 6-methoxy derivatives 1b-d still showed significant activities but with low toxicity to fibroblasts showing promising in vitro therapeutic index. The more bulky 7-phenyl 1-5e and 7-benzofuryl 1-5f derivatives were generally inactive. On the other hand, 6-substituted 7-deazapurine nucleosides bearing small ethynyl group at position 7 (1-5g) displayed considerable activity against several cell lines; in particular, the 6-methylsulfanyl derivative had a low nanomolar $IC_{50}$ values valued against most tumor cells but had little effect on fibroblasts. The 7-unsubstituted derivatives RC1-4 (analogous to tubercidin) did not show significant cytotoxic effect with the exception of 6-methyl derivative RC5 which was the most cytotoxic compound of the entire set to both cancer cells and fibroblasts. The unusual specific effect of 2-furyl and ethynyl substitution on cytostatic activity was the major difference from the 7-(het) aryl-7-deazaadenosines [compounds of formula A, see BACKGROUND OF INVENTION; (ref.: Bourderioux, A.; Nauš, P.; Hocek, M., U.S. 61/171,656 (2009), PCT/CZ2010/000050, WO2010121576 A2; Bourderioux, A.; Nauš, P.; Perlíková, P.; Pohl, R.; Pichová, I.; Votruba, I.; Džubák, P.; Konečný, P.; Hajdúch, M.; Stray, K. M.; Wang, T.; Ray, A. S.; Feng, J. Y.; Birkus, G.; Cihlar, T.; Hocek, M., J. Med. Chem. 2011, 54, 5498-5507)], where all compounds bearing five-membered heterocyclic substituents exerted similar low nanomolar effects. On the other hand, the SAR analysis of the entire panel of compounds shows that the H-bond-donating $NH_2$ group at the position 6 can be replaced by H-bond acceptor groups or even by an isosteric but non-polar methyl group, with some analogues retaining high cytotoxic activity.

Multidrug resistance is a major therapeutic problem in cancer chemotherapy. It is associated with overexpression of drug transporters, typically multidrug resistance protein 1 (mrp-1) and multidrug resistance gene 1 (mdr-1), which transport in ATP dependent manner drugs extracellularly (ref.: Gottesman, M. M.; Fojo, T.; Bates, S. E. Multidrug resistance in cancer: role of ATP-dependent transporters. Nat. Rev. Cancer. 2002, 2, 48-58). In order to assess efficacy of our compounds in multidrug resistant cancers, we have tested their cytotoxic potency in drug resistant sublines derived from chemosensitive CCRF-CEM T-lymphoblastic and K562 myeloid leukemia cells. CEM daunorubicine resistant (CEM-DNR-bulk) and K562 paclitaxel resistant (K562-TAX) lines, were originally prepared by increasing concentration of cytotoxic compounds and then characterized. While CEM-DNR-bulk cells stabile overexpress mrp-1, K562-TAX cells express only mdr-1 gene (ref.: Noskova, V.; Dzubak, P.; Kuzmina, G.; Ludkova, A.; Stehlik, D.; Trojanec, R.; Janostakova, A.; Korinkova, G.; Mihal, V.; Hajduch, M. In vitro chemoresistance profile and expression/function of MDR associated proteins in resistant cell lines derived from CCRF-CEM, K562, A549 and MDA MB 231 parental cells. *Neoplasma* 2002, 49, 418-425) Unfortunately, vast majority of cytotoxic compounds with submicromolar activity showed decreased potency in drug-resistant sublines overexpressing multidrug transporters. Similarly to the multidrug resistance phenomenon, functional inactivation of p53 tumor suppressor is associated with poor prognosis and therapeutic response in many cancers (Muller, P. A.; Vousden, K. H. p53 mutations in cancer. *Nat. Cell. Biol.* 2013, 15, 2-8). Therefore, we have evaluated in vitro therapeutic potency of nucleoside derivatives using isogenic colorectal cancer cells bearing wild type (HCT116) or deleted p53 gene (HCT116p53−/−). Interestingly, the compounds were equally toxic for tumor cells bearing wild-type or null alleles of p53 gene indicating potential therapeutic activity in p53 mutant tumors.

TABLE 1

Cytotoxic activity of compounds

| | MTT, $IC_{50}$ (μM) | | | | | | | | XTT, $IC_{50}$ (μM) | | |
|---|---|---|---|---|---|---|---|---|---|---|---|
| Comp. | CCRF-CEM | CEM-DNR-bulk | K562 | K562-TAX | A549 | HCT116 | HCT116 p53-/- | BJ | MRC-5 | HepG2 | HL60 | HeLa S3 |
| 1a | 0.02 | 0.16 | 0.06 | 0.38 | 0.03 | 0.04 | 0.04 | 0.43 | 1.70 | 0.30 | 0.10 | 1.02 |
| 1b | 0.11 | >20 | 0.19 | 2.82 | 1.16 | 0.11 | 0.13 | 28.8 | 29.4 | 0.29 | 0.15 | 1.79 |
| 1c | 0.09 | 12.1 | 0.07 | 6.20 | 4.85 | 0.08 | 0.44 | 62.8 | 43.2 | 13.9 | 0.08 | 1.76 |
| 1d | 2.57 | 7.64 | 0.09 | 3.45 | 5.17 | 0.12 | 0.14 | 64.3 | 75.3 | 0.43 | 0.13 | 3.35 |
| 1e | >20 | >20 | >20 | >20 | >20 | >20 | >20 | >100 | >100 | >20 | >20 | >20 |
| 1f | 5.37 | 10.8 | 20.9 | 13.1 | 17.7 | 13.8 | 14.5 | 22.4 | 65.6 | >20 | 4.47 | 9.24 |
| 1g | >20 | 3.49 | 0.30 | 0.38 | 8.16 | 4.06 | 5.14 | 98.4 | >100 | 12.7 | 0.19 | 1.73 |
| RC1 | >20 | >20 | >20 | >20 | >20 | >20 | >20 | >100 | >100 | >20 | >20 | >20 |
| 1h | 1.15 | >20 | >20 | 14.8 | >20 | >20 | >20 | 91.0 | 63.0 | >20 | 2.30 | 14.3 |
| 2a | 0.05 | 0.23 | 0.04 | 0.21 | 0.05 | 0.02 | 0.01 | 0.26 | 73.9 | 0.22 | 0.12 | 0.54 |
| 2b | 14.2 | >20 | 0.06 | 3.25 | 0.28 | 0.04 | 0.10 | 98.8 | >100 | >15 | 0.36 | 5.39 |
| 2c | >20 | >20 | 11.6 | >20 | >20 | >20 | >20 | 96.9 | >100 | >20 | 1.13 | 1.96 |
| 2d | >20 | >20 | 0.45 | >20 | >20 | >20 | >20 | 95.8 | >100 | >15 | 4.59 | >20 |
| 2e | >20 | >20 | >20 | >20 | >20 | >20 | >20 | >100 | >100 | >20 | >20 | >20 |
| 2f | >20 | >20 | 17.2 | >20 | >20 | >20 | >20 | 67.2 | 70.8 | >20 | 1.21 | 1.93 |
| 2g | >20 | 0.11 | 0.03 | 0.07 | 0.14 | 0.03 | 0.09 | 68.6 | >100 | >15 | 0.05 | 0.11 |
| RC2 | >20 | 3.61 | >20 | 0.10 | >20 | >20 | >20 | >100 | >100 | >20 | 7.19 | 11.9 |
| 2h | >20 | >20 | 10.5 | 7.73 | >20 | >20 | >20 | 86.1 | >100 | >20 | 0.05 | 0.25 |
| 3a | 0.18 | >20 | 0.22 | 15.1 | 2.57 | 0.23 | 0.44 | 5.04 | 90.8 | 0.85 | 0.62 | 5.00 |
| 3b | >20 | >20 | >20 | >20 | >20 | >20 | >20 | 96.3 | >100 | >20 | >15 | >20 |
| 3c | >20 | >20 | >20 | >20 | >20 | >20 | >20 | >100 | >100 | >20 | >20 | >20 |
| 3d | >20 | >20 | >20 | >20 | >20 | >20 | >20 | >100 | >100 | >20 | >20 | >20 |
| 3e | >20 | >20 | >20 | >20 | >20 | >20 | >100 | >100 | >100 | >20 | >20 | >20 |
| 3f | >20 | >20 | >20 | >20 | >20 | >20 | >20 | 75.6 | 75.3 | >20 | 8.95 | >20 |
| 3g | >20 | 18.5 | >20 | 1.38 | >20 | >20 | >20 | 86.0 | >100 | >15 | 9.06 | >20 |
| RC3 | >20 | 4.89 | >20 | 0.92 | >20 | >20 | >20 | 91.4 | 97.8 | >20 | 12.8 | >20 |
| 3h | >100 | >20 | >100 | >20 | >100 | >100 | >100 | >100 | >100 | >20 | >20 | >20 |
| 4a | 2.91 | 3.14 | 0.15 | 1.28 | 4.60 | 0.25 | 0.32 | >100 | >100 | >15 | 0.22 | 1.19 |
| 4b | 13.3 | >20 | 1.54 | 14.9 | >20 | >20 | >20 | 99.2 | >100 | 12.5 | 1.16 | 9.06 |
| 4c | >20 | >20 | >20 | >20 | >20 | >20 | >20 | >100 | >100 | >20 | 11.8 | >20 |
| 4d | 3.48 | >20 | 0.53 | >20 | >20 | >20 | >20 | >100 | >100 | >20 | 1.92 | >15 |
| 4e | >20 | >20 | >20 | >20 | >100 | >20 | >20 | >100 | >100 | >20 | >20 | >20 |
| 4f | >20 | >20 | >20 | >20 | >20 | >20 | >20 | >100 | >100 | >20 | >20 | >20 |
| 4g | 0.09 | 0.24 | 0.11 | 0.26 | 0.39 | 0.18 | 0.29 | 0.41 | 36.1 | 1.32 | 0.29 | 0.81 |
| RC4 | 0.63 | 2.60 | 5.28 | 0.89 | >20 | 18.4 | 5.09 | 5.30 | 58.2 | 1.81 | 0.87 | 10.6 |
| 4h | 1.59 | 0.10 | 0.07 | 0.05 | 0.34 | 0.09 | 0.12 | 45.7 | 91.7 | 13.9 | 0.05 | 0.19 |
| 5a | 0.04 | 0.07 | 0.04 | 0.11 | 0.11 | 0.04 | 0.04 | 0.07 | 0.61 | 0.30 | 0.21 | 1.33 |
| 5b | >20 | >20 | >20 | >20 | >20 | >20 | >20 | 89.2 | 98.3 | 5.32 | >15 | >20 |
| 5c | >20 | >20 | >20 | >20 | >20 | >20 | >20 | >100 | >100 | >15 | 5.73 | >15 |
| 5d | 11.2 | 8.56 | 0.32 | 5.55 | >20 | 0.46 | 1.43 | 96.9 | >100 | 4.72 | 0.35 | 14.3 |
| 5e | >20 | >20 | >20 | >20 | >20 | >100 | 95.3 | >100 | >100 | >20 | >20 | >20 |
| 5f | 17.3 | >203 | 19.5 | >20 | >20 | >20 | >20 | 93.9 | 84.4 | >20 | >20 | >20 |
| 5g | 5.60 | 0.16 | 6.92 | 0.11 | 19.2 | >20 | >20 | 0.05 | 1.44 | 0.29 | 1.11 | 14.7 |
| RC5 | 0.01 | 0.05 | 0.01 | 0.05 | 0.03 | 0.03 | 0.06 | 0.07 | 0.09 | 0.06 | 0.02 | 0.02 |
| 5h | 5.48 | 12.6 | 17.8 | >20 | 12.2 | 4.72 | 7.57 | >100 | 13.3 | 3.46 | 2.65 | 4.08 |
| 5i | 15.0 | >20 | >20 | 15.8 | >20 | 15.7 | 19.6 | >100 | 24.4 | 5.55 | 7.24 | 13.8 |

Cell Cycle Analysis

Cell cycle analysis of selected compounds with low-micromolar cytotoxicity in cancer cells (1a, 1b, 1c, 1d, 1h, 2a, 3a, 4a, 4d, 4g and 4h) was performed on CCRF-CEM lymphoblasts at the concentration corresponding to the $IC_{50}$ after 24 hours of incubation (Table 2). Some of the compounds induced major apoptosis (1d) as early as after 24 hours. However, the major mechanism of action was inhibition of RNA synthesis (BrU incorporation). DNA synthesis was barely inhibited by compounds 2a, 4d and 1h, and this most probably occurred via action at the level of cellular signaling and metabolic pathways. Cell cycle alterations (G1, S, G2/M) were not observed in treated cells under specified experimental conditions.

TABLE 2

Summary of cell cycle, apoptosis (sub-G1), mitosis (pH3+), RNA (BrU+), and DNA (BrdU+) synthesis analysis[a]

| | % of total cell populations | | | | | | |
|---|---|---|---|---|---|---|---|
| | sub-G1 | G1 | S | G2/M | pH3$^{Ser10+}$ | BrdU+ | BrU+ |
| Control | 9.6 | 41 | 44.8 | 14.2 | 1.4 | 50.1 | 43.3 |
| 1a | 6.8 | 42.8 | 44.3 | 12.9 | 1.4 | 45.3 | 13.8 |
| 1b | 8.5 | 43.5 | 44.2 | 12.3 | 1.6 | 44.2 | 0.7 |
| 1c | 7.5 | 41.5 | 48.7 | 9.8 | 1.1 | 38.6 | 0.1 |
| 1d | 75 | 40.8 | 46.5 | 12.7 | 2.9 | 44.4 | 0.5 |
| 2a | 7.9 | 43.5 | 45.3 | 11.3 | 0.7 | 29.5 | 5 |
| 3a | 10.6 | 42.2 | 45.8 | 12.1 | 1.4 | 47.2 | 1. |
| 4a | 10.2 | 31 | 53.6 | 15.4 | 1.5 | 50.6 | 0.4 |
| 4d | 6.8 | 41.4 | 47.4 | 11.2 | 0.7 | 36.1 | 0.7 |
| 4g | 8.9 | 38.5 | 46.8 | 14.7 | 1.3 | 43.4 | 8.6 |
| 1h | 6 | 37.9 | 49.2 | 12.9 | 0.9 | 38.9 | 0.2 |
| 4h | 9.4 | 39.8 | 46.7 | 13.5 | 1.3 | 48.7 | 4.8 |

[a] in CCRF-CEM cells treated with selected nucleosides at IC$_{50}$ for 24 hrs.

EXAMPLE 42

Antiviral Activity

For antiviral testings following reference compounds RC1-5 were used:

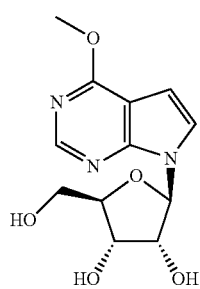

RC1

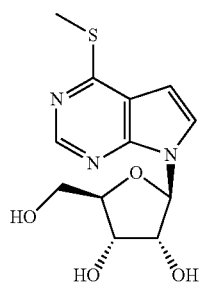

RC2

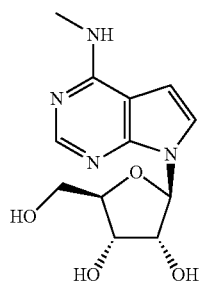

RC3

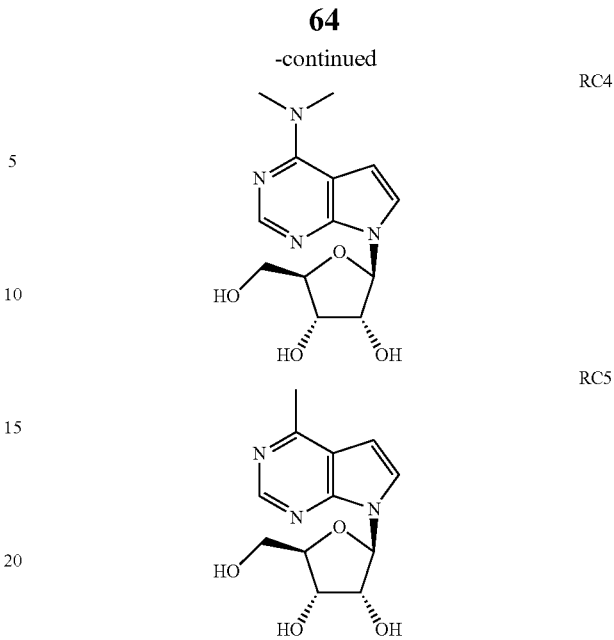

RC4

RC5

Compounds RC1-4 were reported (ref.: Gerster, J. F.; Carpenter, B.; Robins, R. K.; Townsend, L. B. Pyrrolopyrimidine Nucleosides. I. The Synthesis of 4-Substituted 7-(β-D-Ribofuranosyl)pyrrolo[2,3-d]pyrimidines from Tubercidin. *J. Med. Chem.* 1967, 10, 326-331) and compound RC5 is also known (Wu, R.; Smidansky, E. D.; Oh, H. S.; Takhampunya, R.; Padmanabhan, R.; Cameron, C. E.; Peterson, B. R. Synthesis of a 6-Methyl-7-deaza Analogue of Adenosine That Potently Inhibits Replication of Polio and Dengue Viruses. *J. Med. Chem.* 2010, 53, 7958-7966) Compound 1h was described previously and for present testing was covered only as reference compound for testing (ref.: Seela, F.; Ming, X. 7-Functionalized 7-deazapurine β-D and β-L-ribonucleosides related to tubercidin and 7-deazainosine: glycosylation of pyrrolo[2,3-d]pyrimidines with 1-O-acetyl-2,3,5-tri-O-benzoyl-β-D or β-L-ribofuranose. *Tetrahedron* 2007, 63, 9850-9861; Zhang, L.; Zhang, Y.; Li, X.; Zhang, L., *Bioorg. Med. Chem.* 2002, 10, 907-912).

Compounds were also tested in Huh-7 cells harboring sub-genomic reporter replicons derived from HCV subtypes 1B and 2A (ref.: Stuyver, L. J.; Whitaker, T.; McBrayer, T. R.; Hernandez-Santiago, B. I.; Lostia, S.; Tharnish, P. M.; Ramesh, M.; Chu, C. K.; Jordan, R.; Shi, J. X.; Rachakonda, S.; Watanabe, K. A.; Otto, M. J.; Schinazi, R. F. *Antimicrob. Agents Chemother.* 2003, 47, 244-254). Partial inhibition of the replicon reporter was observed with most of the compounds (Table 3). Activity correlated with cytotoxicity in most cases, suggesting that the activity detected by the replicon assay was a reflection of interference with host target(s).

TABLE 3

Anti-HCV activities of selected compounds[a]

| | Replicon 1B | | Replicon 2A | |
|---|---|---|---|---|
| | EC$_{50}$ (μM) | CC$_{50}$ (μM) | EC$_{50}$ (μM) | CC$_{50}$ (μM) |
| 1a | 0.02 | >44 | 0.03 | >44 |
| 1b | 0.33 | >44 | 8.28 | >44 |
| 1c | 1.08 | >44 | >44 | >44 |
| 1d | 0.55 | >44 | >44 | >44 |
| 1e | 20.98 | >44 | >44 | >44 |

TABLE 3-continued

Anti-HCV activities of selected compounds[a]

| | Replicon 1B | | Replicon 2A | |
|---|---|---|---|---|
| | $EC_{50}$ (μM) | $CC_{50}$ (μM) | $EC_{50}$ (μM) | $CC_{50}$ (μM) |
| 1f | 2.64 | >44 | 10.23 | >44 |
| 1g | 0.18 | >44 | >44 | >44 |
| 1h | >44 | >44 | >44 | >44 |
| RC1 | 43.23 | >44 | >44 | >44 |
| 2a | 0.07 | 38.58 | 0.05 | >44 |
| 2b | 4.72 | >44 | >44 | >44 |
| 2c | 5.42 | >44 | >44 | >44 |
| 2d | 10.93 | >44 | >44 | >44 |
| 2e | 23.27 | >44 | >44 | >44 |
| 2f | 8.03 | >44 | 29.64 | >44 |
| 2g | 0.21 | >44 | >44 | >44 |
| 2h | 19.21 | >44 | >44 | >44 |
| RC2 | 29.89 | >44 | >44 | >44 |
| 2h | 19.21 | >44 | >44 | >44 |
| 3a | 0.06 | >44 | 0.14 | >44 |
| 3b | 35.93 | >44 | >44 | >44 |
| 3c | >44 | >44 | >44 | >44 |
| 3d | >44 | >44 | >44 | >44 |
| 3e | >44 | >44 | >44 | >44 |
| 3f | 2.05 | >44 | 13.57 | >44 |
| 3g | 0.35 | >44 | >44 | >44 |
| RC3 | 0.82 | >44 | >44 | >44 |
| 4a | 1.49 | >44 | 1.35 | >44 |
| 4b | 7.88 | >44 | >44 | >44 |
| 4c | 16.76 | >44 | >44 | >44 |
| 4d | 38.41 | >44 | >44 | >44 |
| 4e | 26.88 | >44 | >44 | >44 |
| 4f | 19.20 | >44 | >44 | >44 |
| 4g | 0.07 | >44 | 0.10 | >44 |
| RC4 | 0.27 | >44 | 0.97 | >44 |
| 4h | 0.69 | >44 | >44 | >44 |
| 5a | 0.07 | 6.62 | 0.15 | 43.60 |
| 5b | 4.43 | >44 | >44 | >44 |
| 5c | 6.67 | >44 | >44 | >44 |
| 5d | 4.47 | >44 | >44 | >44 |
| 5e | 34.83 | >44 | >44 | >44 |
| 5f | 6.76 | >44 | 40.20 | >44 |
| 5g | 0.23 | >44 | 21.60 | >44 |
| RC5 | 0.02 | 0.23 | 0.02 | 0.12 |

What is claimed is:

1. A method of treating a disease, the disease being selected from cancer and a tumor disease, the method comprising administering a compound according to formula I, or a pharmaceutically acceptable salt thereof, to a subject in need thereof;
wherein said compound according to formula I is according to:

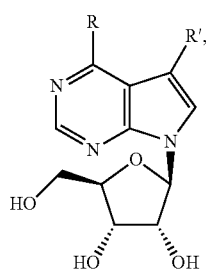

wherein,
R is methylsulfanyl, methoxy, methylamino, dimethylamino or methyl;
R' is furan-2-yl, furan-3-yl, thiophen-2-yl, thiophen-3-yl, phenyl, benzofuran-2-yl, ethynyl, or iodine;
a pharmaceutically acceptable salt thereof, an optical isomer thereof, or a mixture of optical isomers thereof;
with the proviso that if R' is iodine, R is not methoxy.

2. The method according to claim 1,
wherein the compound according to formula I is selected from the group consisting of
5-(Furan-2-yl)-4-methoxy-7-(β-D-ribofuranosyl)-7H-pyrrolo[2,3-d]pyrimidine,
5-(Furan-3-yl)-4-methoxy-7-(β-D-ribofuranosyl)-7H-pyrrolo[2,3-d]pyrimidine,
4-Methoxy-7-(β-D-ribofuranosyl)-5-(thiophen-2-yl)-7H-pyrrolo[2,3-d]pyrimidine,
4-Methoxy-7-(β-D-ribofuranosyl)-5-(thiophen-3-yl)-7H-pyrrolo[2,3-d]pyrimidine,
4-Methoxy-5-phenyl-7-(β-D-ribofuranosyl)-7H-pyrrolo[2,3-d]pyrimidine,
5-(Benzofuran-2-yl)-4-methoxy-7-(β-D-ribofuranosyl)-7H-pyrrolo[2,3-d]pyrimidine,
5-Ethynyl-4-methoxy-7-(β-D-ribofuranosyl)-7H-pyrrolo[2,3-d]pyrimidine,
5-Iodo-4-methylsulfanyl-7-(β-D-ribofuranosyl)-7H-pyrrolo[2,3-d]pyrimidine,
5-(Furan-2-yl)-4-methylsulfanyl-7-(β-D-ribofuranosyl)-7H-pyrrolo[2,3-d]pyrimidine,
5-(Furan-3-yl)-4-methylsulfanyl-7-(β-D-ribofuranosyl)-7H-pyrrolo[2,3-d]pyrimidine,
4-Methylsulfanyl-7-(β-D-ribofuranosyl)-5-(thiophen-2-yl)-7H-pyrrolo[2,3-d]pyrimidine,
4-Methylsulfanyl-7-(β-D-ribofuranosyl)-5-(thiophen-3-yl)-7H-pyrrolo[2,3-d]pyrimidine,
4-Methylsulfanyl-5-phenyl-7-(β-D-ribofuranosyl)-7H-pyrrolo[2,3-d]pyrimidine,
5-(Benzofuran-2-yl)-4-methylsulfanyl-7-(β-D-ribofuranosyl)-7H-pyrrolo[2,3-d]pyrimidine,
5-Ethynyl-4-methylsulfanyl-7-(β-D-ribofuranosyl)-7H-pyrrolo[2,3-d]pyrimidine,
5-Iodo-4-methylamino-7-(β-D-ribofuranosyl)-7H-pyrrolo[2,3-d]pyrimidine,
5-(Furan-2-yl)-4-methylamino-7-(β-D-ribofuranosyl)-7H-pyrrolo[2,3-d]pyrimidine,
5-(Furan-3-yl)-4-methylamino-7-(β-D-ribofuranosyl)-7H-pyrrolo[2,3-d]pyrimidine,
4-Methylamino-7-(β-D-ribofuranosyl)-5-(thiophen-2-yl)-7H-pyrrolo[2,3-d]pyrimidine,
4-Methylamino-7-(β-D-ribofuranosyl)-5-(thiophen-3-yl)-7H-pyrrolo[2,3-d]pyrimidine,
4-Methylamino-5-phenyl-7-(β-D-ribofuranosyl)-7H-pyrrolo[2,3-d]pyrimidine,
5-(Benzofuran-2-yl)-4-methylamino-(β-D-ribofuranosyl)-7H-pyrrolo[2,3-d]pyrimidine,
5-Ethynyl-4-methylamino-7-(β-D-ribofuranosyl)-7H-pyrrolo[2,3-d]pyrimidine,
4-Dimethylamino-5-iodo-7-(β-D-ribofuranosyl)-7H-pyrrolo[2,3-d]pyrimidine,
4-Dimethylamino-5-(furan-2-yl)-7-(β-D-ribofuranosyl)-7H-pyrrolo[2,3-d]pyrimidine,
4-Dimethylamino-5-(furan-3-yl)-7-(β-D-ribofuranosyl)-7H-pyrrolo[2,3-d]pyrimidine,
4-Dimethylamino-7-(β-D-ribofuranosyl)-5-(thiophen-2-yl)-7H-pyrrolo[2,3-d]pyrimidine,
4-Dimethylamino-7-(β-D-ribofuranosyl)-5-(thiophen-3-yl)-7H-pyrrolo[2,3-d]pyrimidine,
4-Dimethylamino-5-phenyl-(β-D-ribofuranosyl)-7H-pyrrolo[2,3-d]pyrimidine,
5-(Benzofuran-2-yl)-4-dimethylamino-7-(β-D-ribofuranosyl)-7H-pyrrolo[2,3-d]pyrimidine, 4-Dimethylamino-5-ethynyl-7-(β-DD-ribofuranosyl)-7H-pyrrolo[2,3-d]pyrimidine,
5-Iodo-4-methyl-(β-D-ribofuranosyl)-7H-pyrrolo[2,3-d]pyrimidine,
5-(Furan-2-yl)-4-methyl-7-(β-D-ribofuranosyl)-7H-pyrrolo[2,3-d]pyrimidine,
5-(Furan-3-yl)-4-methyl-7-(β-ribofuranosyl)-7H-pyrrolo[2,3-d]pyrimidine,
4-Methyl-7-(β-D-ribofuranosyl)-5-(thiophen-2-yl)-7H-pyrrolo[2,3-d]pyrimidine,
4-Methyl-7-(β-D-ribofuranosyl)-5-(thiophen-3-yl)-7H-pyrrolo[2,3-d]pyrimidine,
4-Methyl-5-phenyl-7-(β-D-ribofuranosyl)-7H-pyrrolo[2,3-d]pyrimidine,
5-(Benzofuran-2-yl)-4-methyl-7-(β-D-ribofuranosyl)-7H-pyrrolo[2,3-d]pyrimidine, and
5-Ethynyl-4-methyl-7-(β-D-ribofuranosyl)-7H-pyrrolo[2,3-d]pyrimidine.

3. The method of claim 1, wherein the treatment comprises inhibition of pathological cell proliferation of one at least one of tumor, non-tumor, and cancer origin.

4. The method claim 1, wherein the treatment is treatment of a disease associated with cell hyperproliferation.

5. The method claim 1, wherein the treatment is treatment of a neoplastic disease.

6. The method claim 1, wherein the treatment is treatment of a cellular proliferation disease.

7. The method of claim 1, wherein said compound of formula I, or said pharmaceutically acceptable salt thereof, is administered as a pharmaceutical composition comprising a therapeutically effective amount of the compound of formula I and one more pharmaceutically acceptable excipients.

8. A method of preparing a medicament for use in the method of claim 7, the method comprising combining a compound according to formula I, or a pharmaceutically acceptable salt thereof, with one or more pharmaceutically acceptable excipients.

9. A compound of formula I:

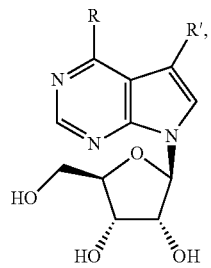

wherein,
R is methylsulfanyl, methoxy, methylamino, dimethylamino, or methyl;
R' is furan-2-yl, furan-3-yl, thiophen-2-yl, thiophen-3-yl, phenyl, benzofuran-2-yl, ethynyl, or iodine;
or a pharmaceutically acceptable salt thereof, an optical isomer thereof, or a mixture of optical isomers thereof;
with the proviso that if R' is iodine, R is not methoxy, methylsulfanyl, or methylamino.

10. A method of treating at least one disease selected from cancer and a tumor disease, the method comprising administering the compound according to claim 9 to a subject in need thereof.

11. A method of preparing a medicament for treatment of a disease, the method comprising combining the compound according to claim 9, or a pharmaceutically acceptable salt thereof, with one or more pharmaceutically acceptable excipients.

12. A method of inhibiting tumor/cancer growth or cell proliferation in tumor or cancer cells comprising administering the compound according to claim 9, or a pharmaceutically acceptable salt thereof, to a subject.

13. A medicament for administration to a subject for treatment of a disease, the medicament comprising a compound according to claim 9 and one or more pharmaceutically acceptable excipients.

14. The compound of claim 9,
wherein the compound is selected from the group consisting of:
5-(Furan-2-yl)-4-methoxy-7-(β-D-ribofuranosyl)-7H-pyrrolo[2,3-d]pyrimidine,
5-(Furan-3-yl)-4-methoxy-7-(β-D-ribofuranosyl)-7H-pyrrolo[2,3-d]pyrimidine,
4-Methoxy-7-(β-D-ribofuranosyl)-5-(thiophen-2-yl)-7H-pyrrolo[2,3-d]pyrimidine,
4-Methoxy-7-(β-D-ribofuranosyl)-5-(thiophen-3-yl)-7H-pyrrolo[2,3-d]pyrimidine,
4-Methoxy-5-phenyl-7-(β-D-ribofuranosyl)-7H-pyrrolo[2,3-d]pyrimidine,
5-(Benzofuran-2-yl)-4-methoxy-7-(β-D-ribofuranosyl)-7H-pyrrolo[2,3]-4pyrimidine,
5-Ethynyl-4-methoxy-(β-D-ribofuranosyl)-7H-pyrrolo[2,3-d]pyrimidine,
5-(Furan-2-yl)-4-methylsulfanyl-7-(β-D-ribofuranosyl)-7H-pyrrolo[2,3-d]pyrimidine,
5-(Furan-3-yl)-4-methylsulfanyl-7-(β-D-ribofuranosyl)-7H-pyrrolo[2,3-d]pyrimidine,
4-Methylsulfanyl-7-(β-D-ribofuranosyl)-5-(thiophen-2-yl)-7H-pyrrolo[2,3-d]pyrimidine,
4-Methylsulfanyl-7-(β-D-ribofuranosyl)-5-(thiophen-3-yl)-7H-pyrrolo[2,3-d]pyrimidine,
4-Methylsulfanyl-5-phenyl-7-(β-D-ribofuranosyl)-7H-pyrrolo[2,3-d]pyrimidine,
5-(Benzofuran-2-yl)-4-methylsulfanyl-7-(β-D-ribofuranosyl)-7H-pyrrolo[2,3-d]pyrimidine,
5-Ethynyl-4-methylsulfanyl-7-(β-D-ribofuranosyl)-7H-pyrrolo[2,3-d]pyrimidine,
5-(Furan-2-yl)-4-methylamino-7-(β-D-ribofuranosyl)-7H-pyrrolo[2,3-d]pyrimidine,
5-(Furan-3-yl)-4-methylamino-7-(β-D-ribofuranosyl)-7H-pyrrolo[2,3-d]pyrimidine,
4-Methylamino-7-(β-D-ribofuranosyl)-5-(thiophen-2-yl)-7H-pyrrolo[2,3-d]pyrimidine,
4-Methylamino-7-(β-D-ribofuranosyl)-5-(thiophen-3-yl)-7H-pyrrolo[2,3-d]pyrimidine,
4-Methylamino-5-phenyl-7-(β-D-ribofuranosyl)-7H-pyrrolo[2,3-d]pyrimidine,
5-(Benzofuran-2-yl)-4-methylamino-7-(β-D-ribofuranosyl)-7H-pyrrolo[2,3-d]pyrimidine,
5-Ethynyl-4-methylamino-7-(β-D-ribofuranosyl)-7H-pyrrolo[2,3-d]pyrimidine,
4-Dimethylamino-5-iodo-7-(β-D-ribofuranosyl)-7H-pyrrolo[2,3-d]pyrimidine,
4-Dimethylamino-5-(furan-2-yl)-7-(β-D-ribofuranosyl)-7H-pyrrolo[2,3-d]pyrimidine,
4-Dimethylamino-5-(furan-3-yl)-7-(β-D-ribofuranosyl)-7H-pyrrolo[2,3-d]pyrimidine,
4-Dimethylamino-7-(β-D-ribofuranosyl)-5-(thiophen-2-yl)-7H-pyrrolo[2,3-d]pyrimidine, 4-Dimethylamino-7-(β-D-ribofuranosyl)-5-(thiophen-3-yl)-7H-pyrrolo[2,3-d]pyrimidine,
4-Dimethylamino-5-phenyl-7-(β-D-ribofuranosyl)-7H-pyrrolo[2,3-d]pyrimidine,
5-(Benzofuran-2-yl)-4-dimethylamino-7-(β-D-ribofuranosyl)-7H-pyrrolo[2,3-d]pyrimidine,
4-Dimethylamino-5-ethynyl-7-(β-D-ribofuranosyl)-7H-pyrrolo[2,3-d]pyrimidine,
5-Iodo-4-methyl-(β-D-ribofuranosyl)-7H-pyrrolo[2,3-d]pyrimidine, 5-(Furan-2-yl)-4-methyl-(β-D-ribofuranosyl)-7H-pyrrolo[2,3-d]pyrimidine,
5-(Furan-3-yl)-4-methyl-(β-D-ribofuranosyl)-7H-pyrrolo[2,3-d]pyrimidine,
4-Methyl-7-(β-D-ribofuranosyl)-5-(thiophen-2-yl)-7H-pyrrolo[2,3-d]pyrimidine,
4-Methyl-7-(β-D-ribofuranosyl)-5-(thiophen-3-yl)-7H-pyrrolo[2,3-d]pyrimidine,
4-Methyl-5-phenyl-7-(β-D-ribofuranosyl)-7H-pyrrolo[2,3-d]pyrimidine,
5-(Benzofuran-2-yl)-4-methyl-7-(β-D-ribofuranosyl)-7H-pyrrolo[2,3-d]pyrimidine, and
5-Ethynyl-4-methyl-7-(β-D-ribofuranosyl)-7H-pyrrolo[2,3-d]pyrimidine.

15. A method of at least one of inhibiting tumor growth, inhibiting cancer growth, inhibiting tumor cell proliferation, and inhibiting cancer cell proliferation, the method comprising administering a compound according to formula I, or a pharmaceutically acceptable salt thereof, to a subject in need thereof;

wherein said compound according to formula I is according to:

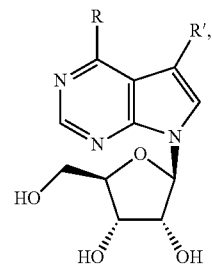

(I)

wherein,

R is methylsulfanyl, methoxy, methylamino, dimethylamino or methyl;

R' is furan-2-yl, furan-3-yl, thiophen-2-yl, thiophen-3-yl, phenyl, benzofuran-2-yl, ethynyl, or iodine;

a pharmaceutically acceptable salt thereof, an optical isomer thereof, or a mixture of optical isomers thereof;

with the proviso that if R' is iodine, R is not methoxy.

* * * * *